(12) United States Patent
Pavcnik et al.

(10) Patent No.: US 7,604,661 B2
(45) Date of Patent: Oct. 20, 2009

(54) IMPLANTABLE VASCULAR DEVICE

(75) Inventors: Dusan Pavcnik, Portland, OR (US);
Thomas A. Osborne, Bloomington, IN (US); Brian C. Case, Lake Villa, IL (US); Jacob A. Flagle, Indianapolis, IN (US); Michael L. Garrison, Indianapolis, IN (US); Ram H. Paul, Jr., Bloomington, IN (US); Andrew K. Hoffa, Bloomington, IN (US); Raymond B. Leonard, II, Bloomington, IN (US); Darin G. Schaeffer, Bloomington, IN (US); Richard B. Sisken, West Lafayette, IN (US)

(73) Assignees: Cook Incorporated, Bloomington, IN (US); William Cook Europe ApS, Bjaeverskov (DK); MED Institute, West Lafayette, IN (US); Oregon Health Sciences University, Portland, IN (US)

( * ) Notice: Subject to any disclaimer, the term of this patent is extended or adjusted under 35 U.S.C. 154(b) by 0 days.

(21) Appl. No.: 11/931,182

(22) Filed: Oct. 31, 2007

(65) Prior Publication Data

US 2008/0097586 A1 Apr. 24, 2008

Related U.S. Application Data

(63) Continuation of application No. 10/642,372, filed on Aug. 15, 2003, and a continuation-in-part of application No. 09/777,091, filed on Feb. 5, 2001, now Pat. No. 7,452,371.

(60) Provisional application No. 60/403,783, filed on Aug. 15, 2002.

(51) Int. Cl.
*A61F 2/06* (2006.01)
*A61F 2/24* (2006.01)
(52) U.S. Cl. .................. 623/1.24; 623/2.14; 623/2.17
(58) Field of Classification Search ............ 623/1.24, 623/1.26, 2.12–2.42, 900
See application file for complete search history.

(56) References Cited

U.S. PATENT DOCUMENTS

| 5,855,601 | A * | 1/1999 | Bessler et al. ............. 623/2.38 |
| 6,287,334 | B1 * | 9/2001 | Moll et al. ................ 623/1.24 |
| 2002/0138135 | A1 * | 9/2002 | Duerig et al. ............. 623/1.24 |

* cited by examiner

*Primary Examiner*—David H Willse
*Assistant Examiner*—Javier G Blanco
(74) *Attorney, Agent, or Firm*—Buchanan Intellectual Property Office LLC

(57) ABSTRACT

An valve prosthesis, such as an artificial venous valve, having a support frame and leaf structure comprising one or more leaflets in which the outer edge of each leaflet engages the inner circumference of the bodily passageway along a serpentine path urged against the passageway by an expandable frame, while the inner edges move in response to fluid to restrict retrograde flow. Optionally, one or more elements can extend from the support frame/leaf structure to provide centering support and/or protection from the leaflet adhering to the vessel wall. In one embodiment, the centering support structure comprises a second or third expandable frames attached to and extending from the proximal and/or distal ends of main valve structure and support frame. In another embodiment, one or more support elements extend outward from the valve support frame to engage the vessel wall to provide greater longitudinal stability.

7 Claims, 31 Drawing Sheets

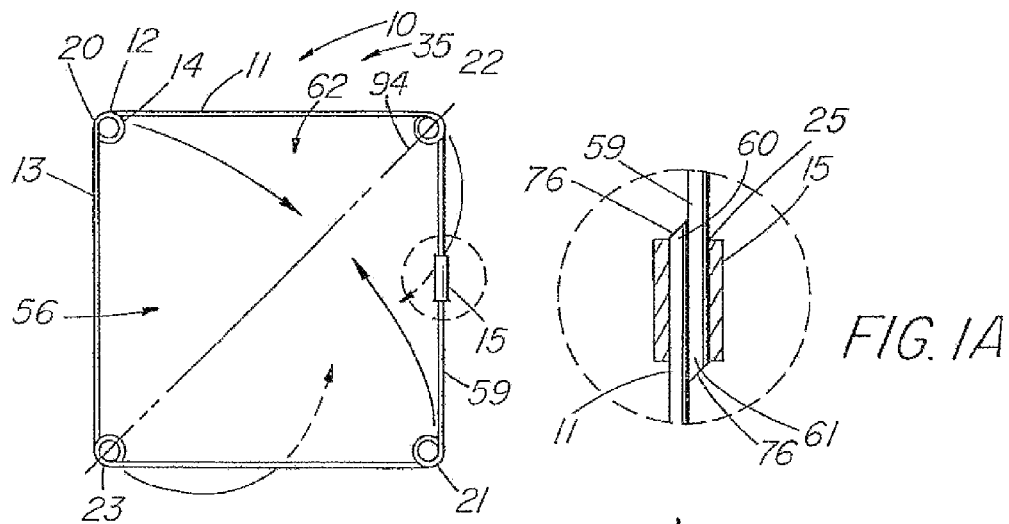
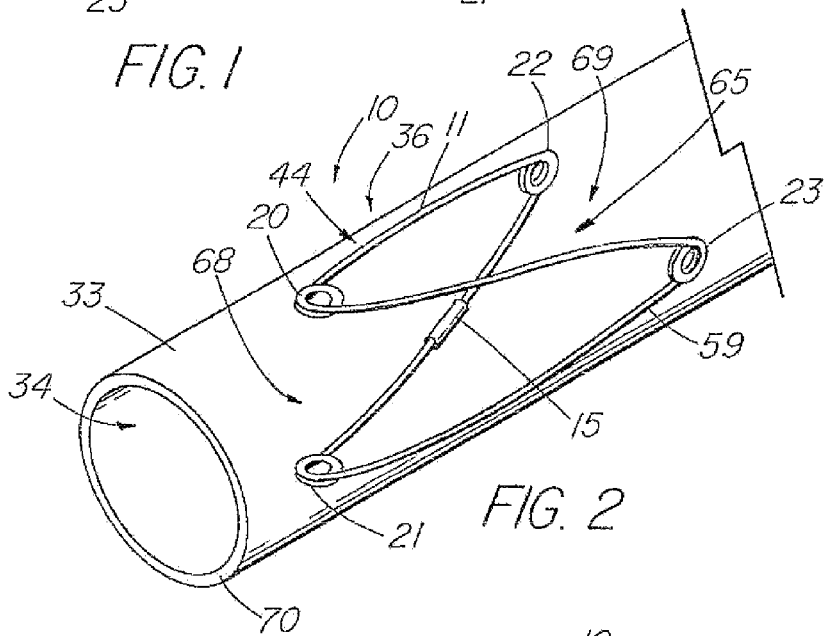
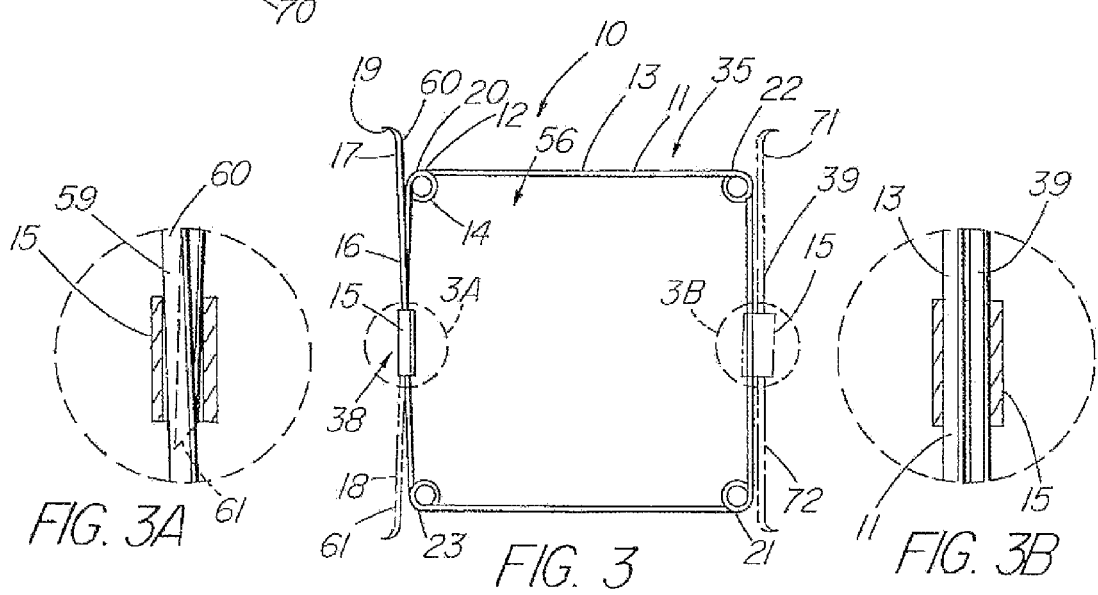

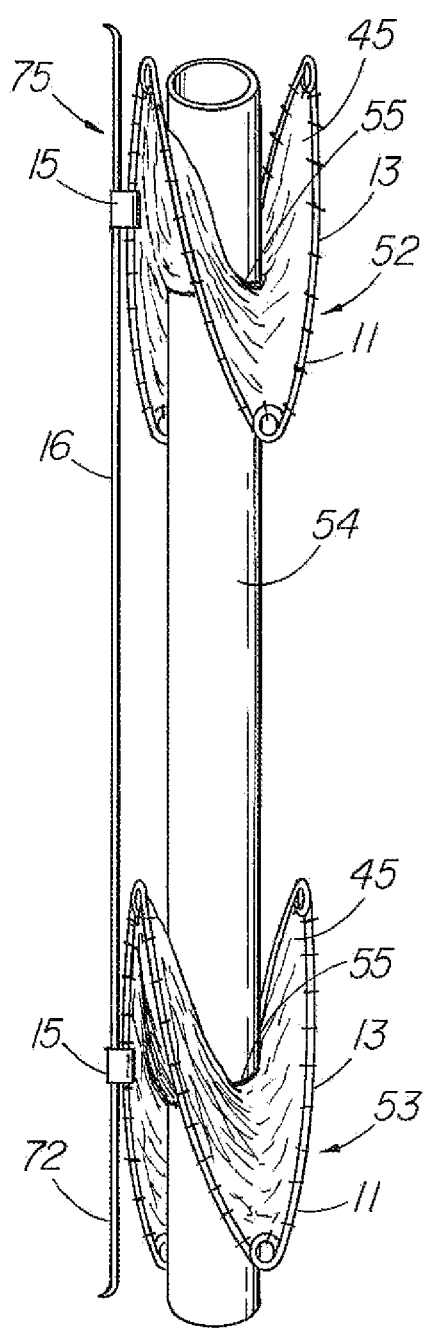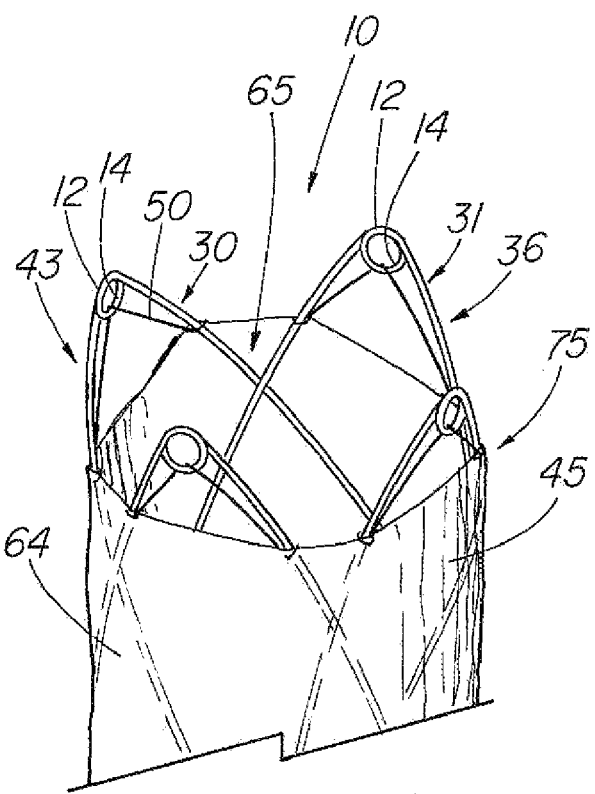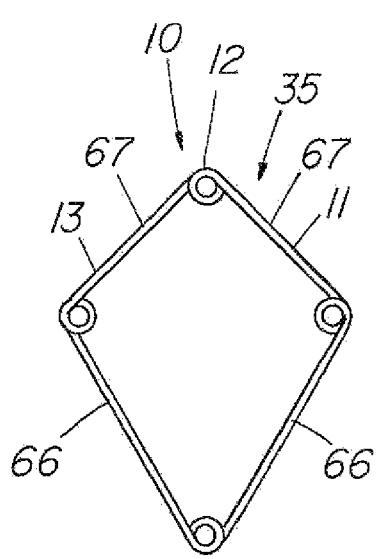
FIG. 17
FIG. 18
FIG. 19

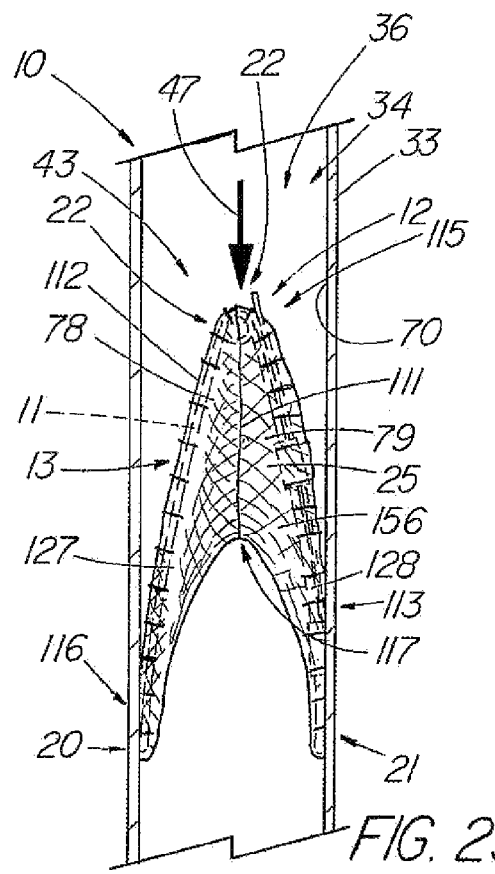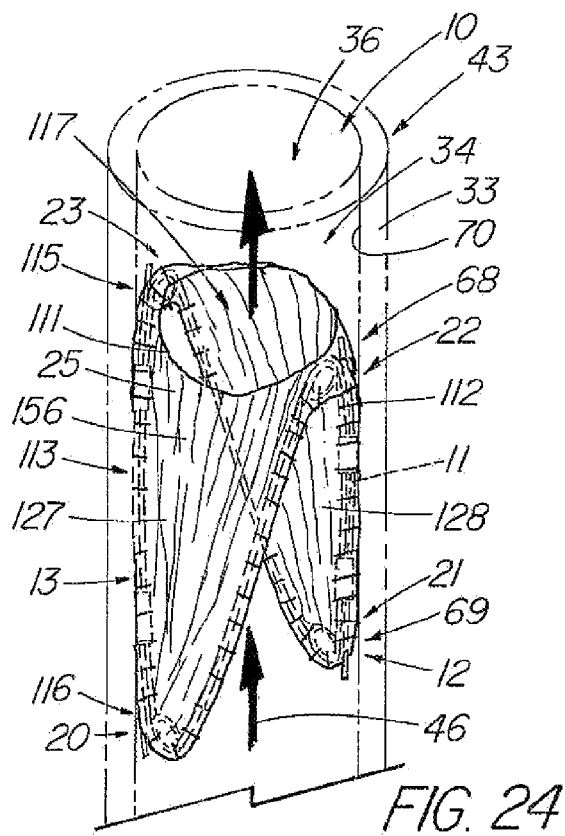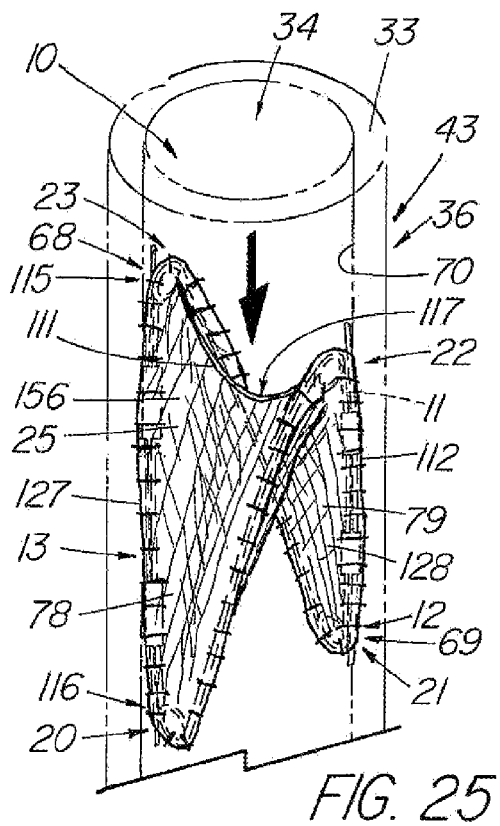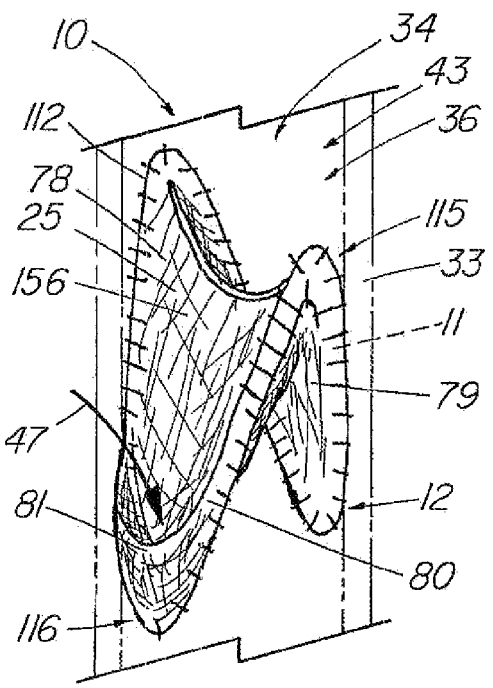

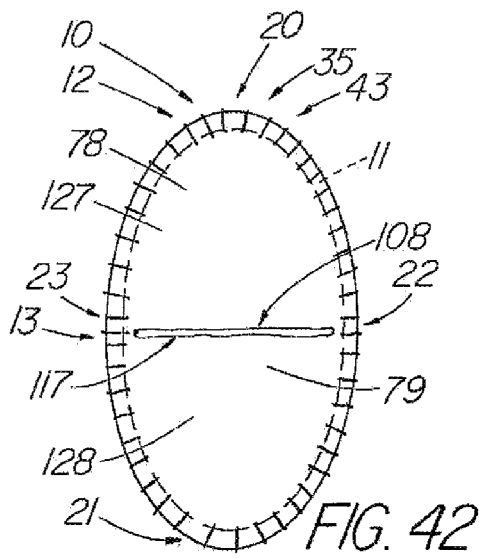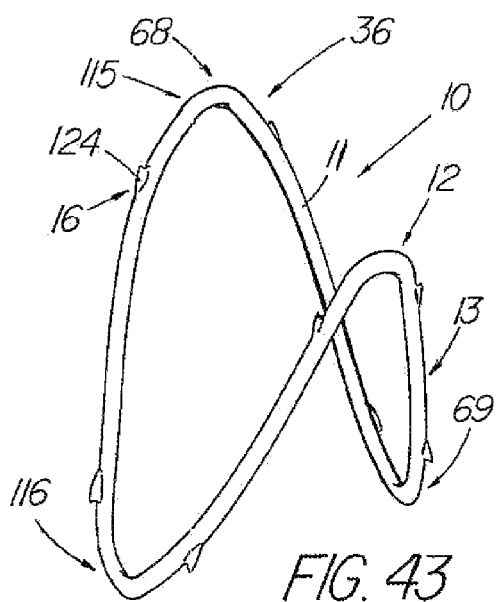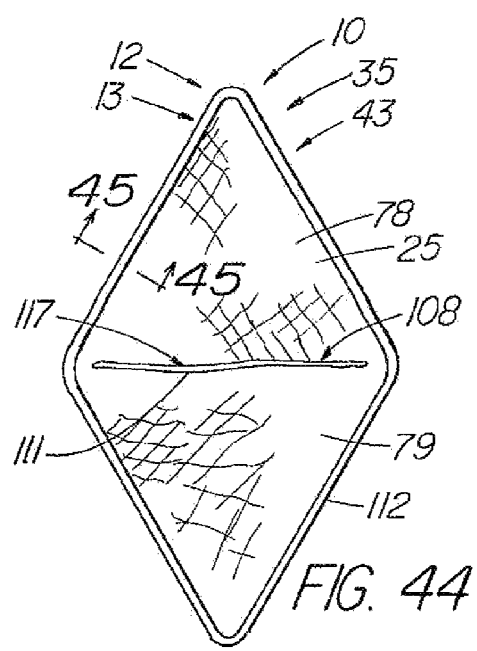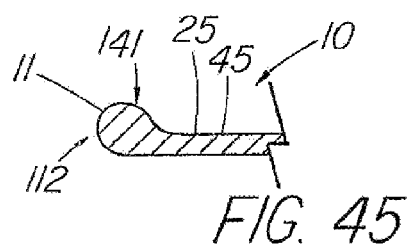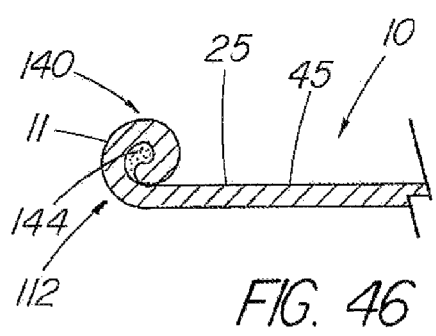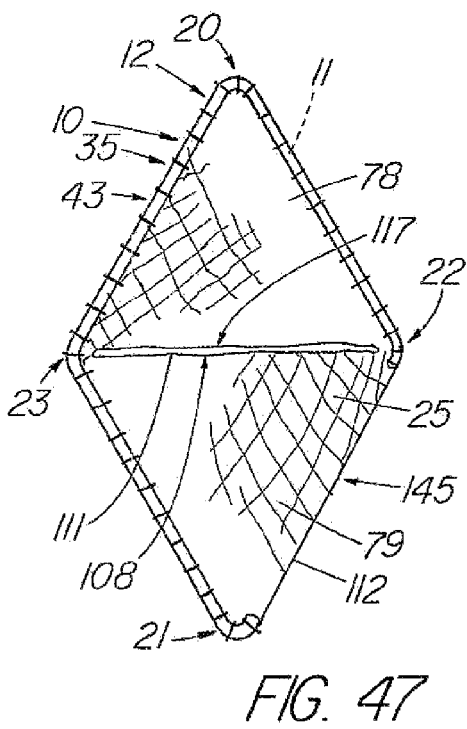

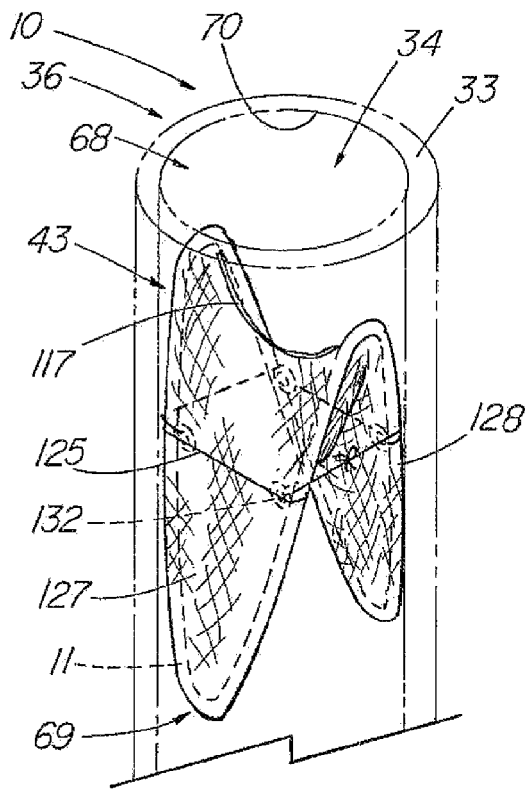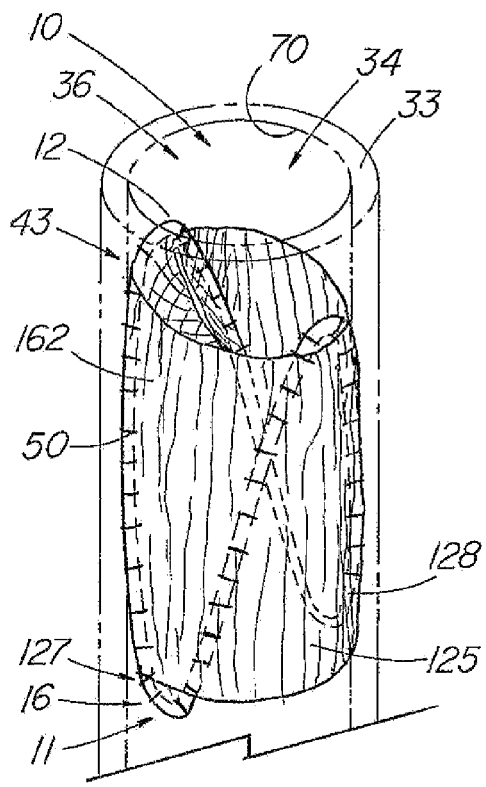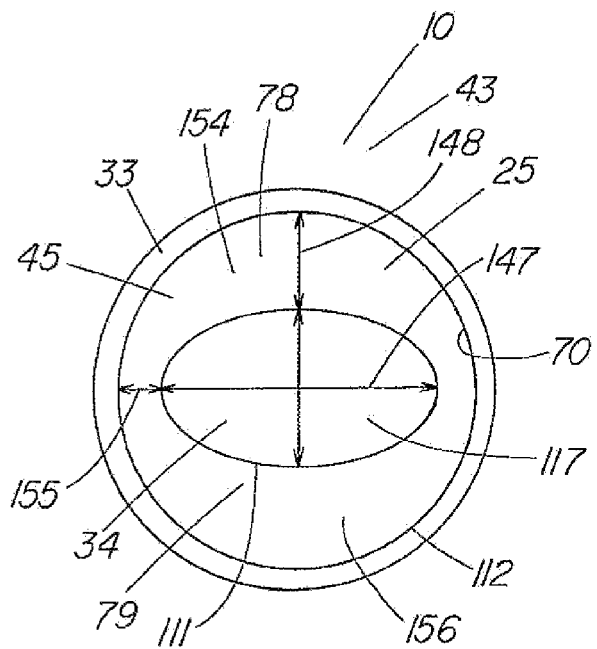

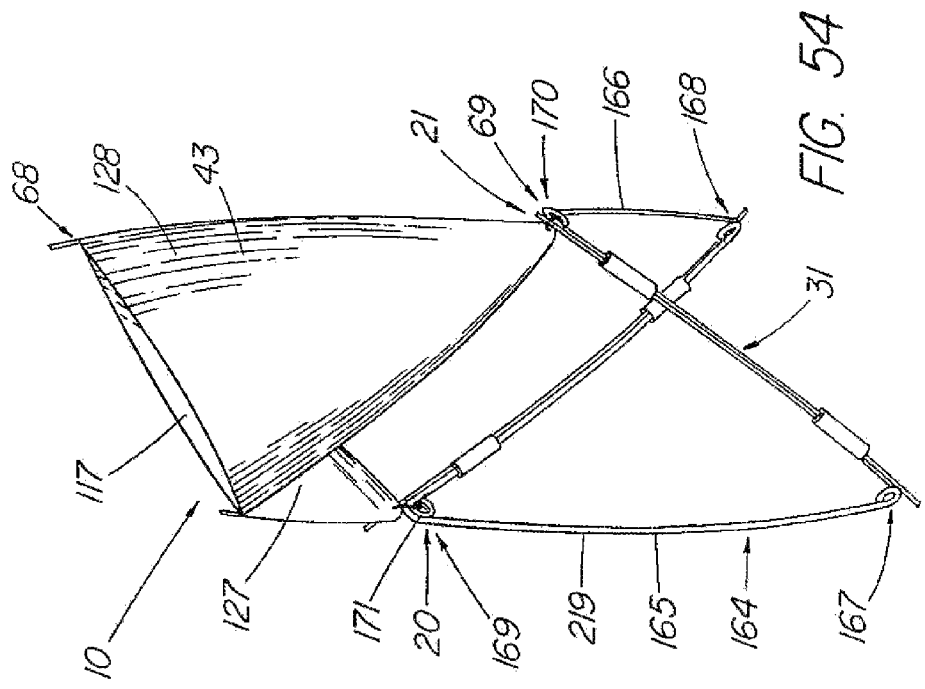
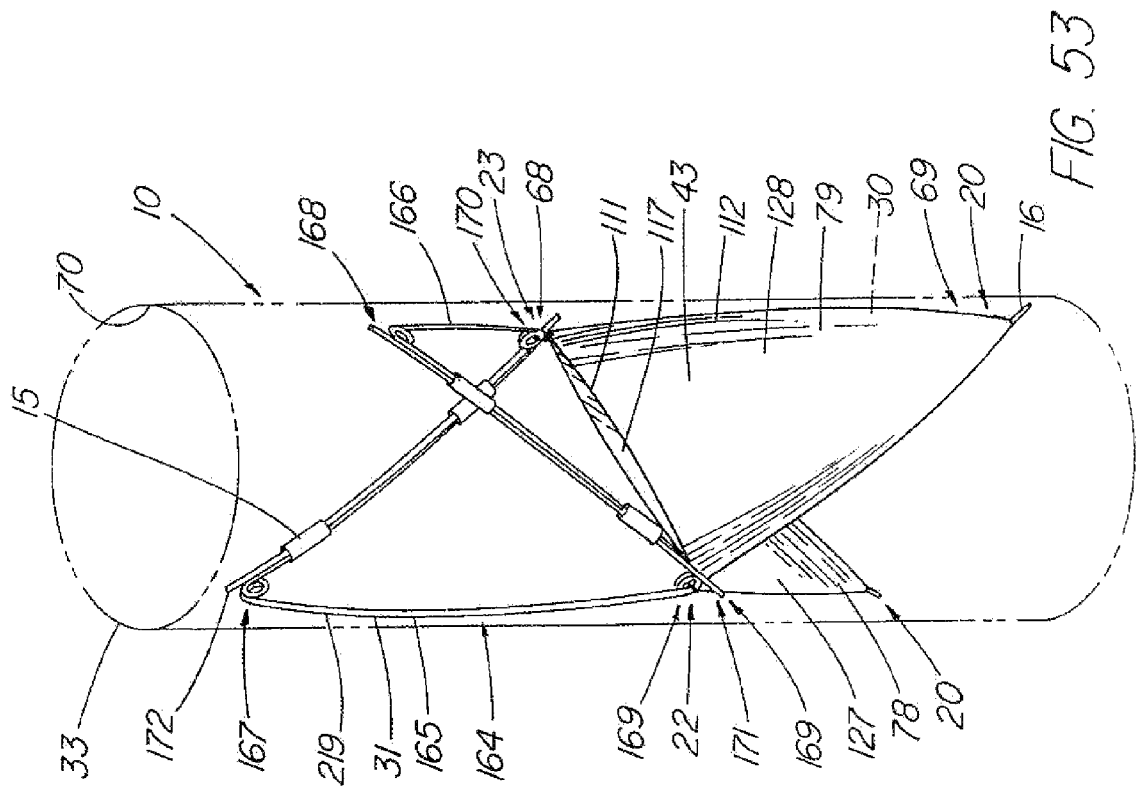

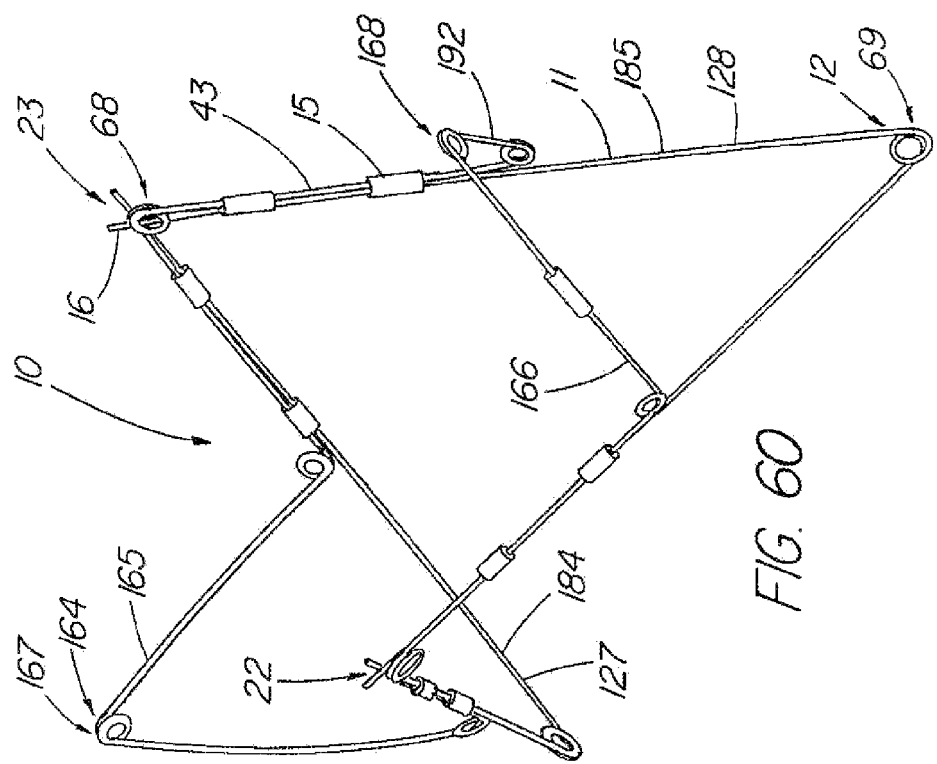
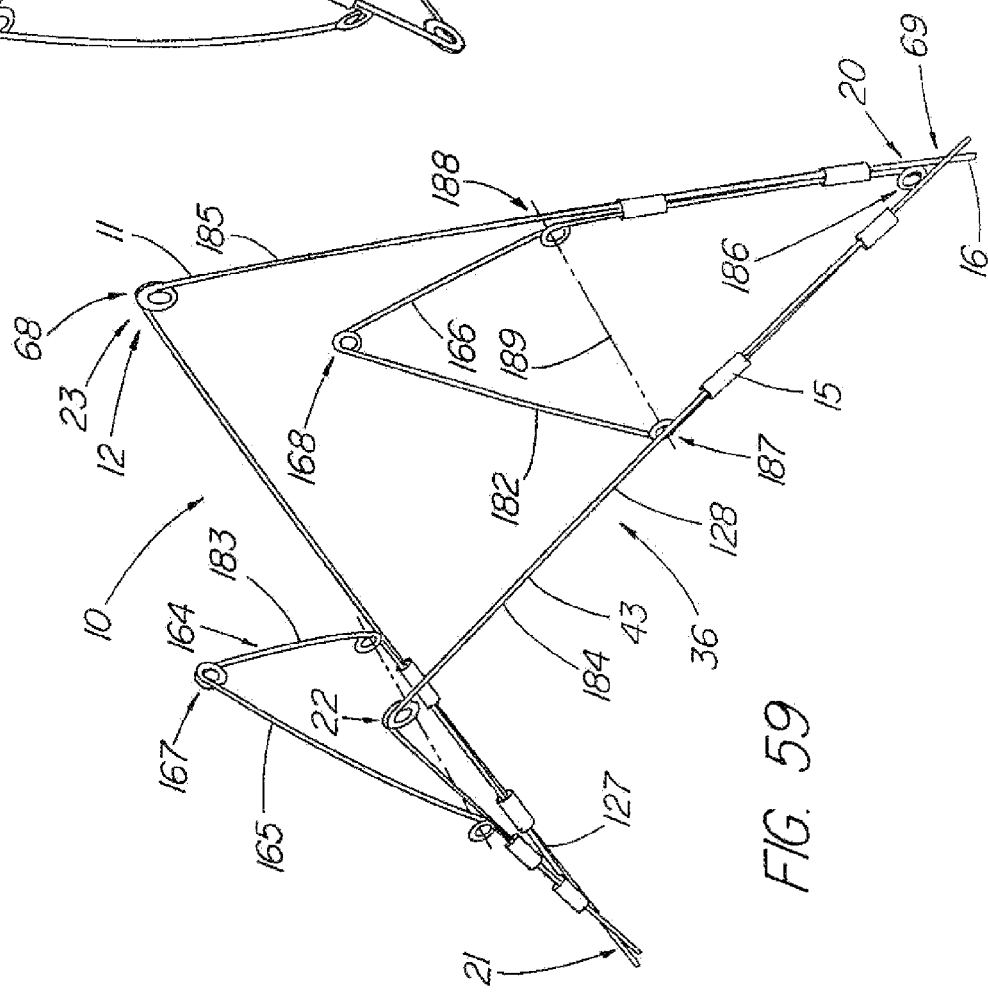

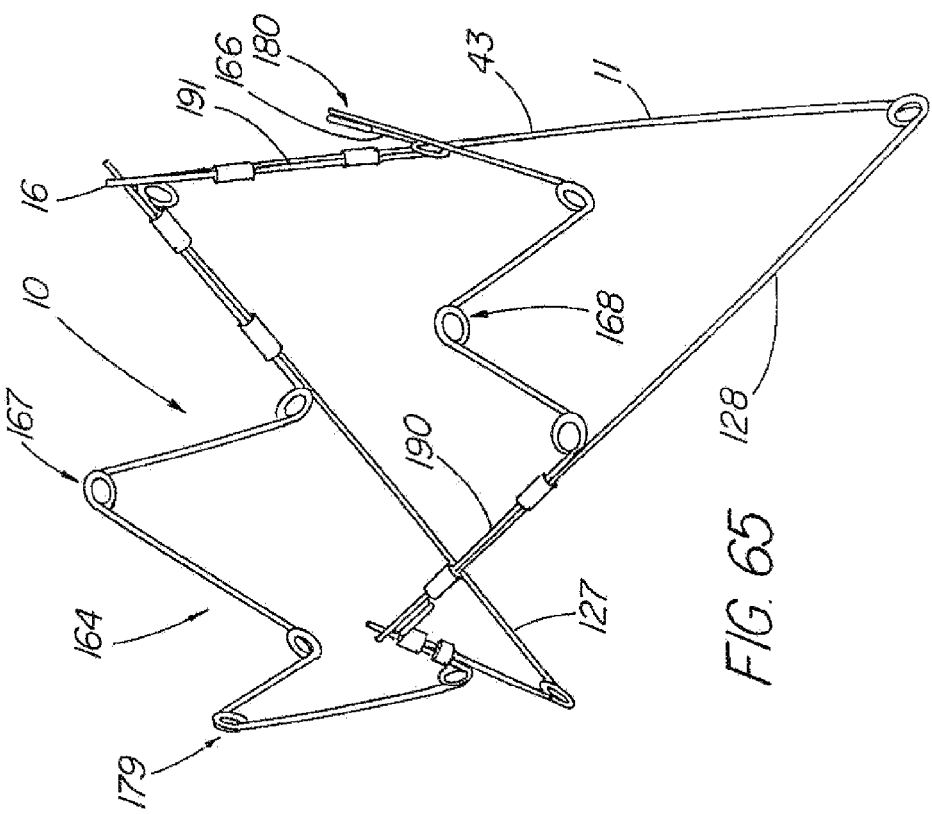
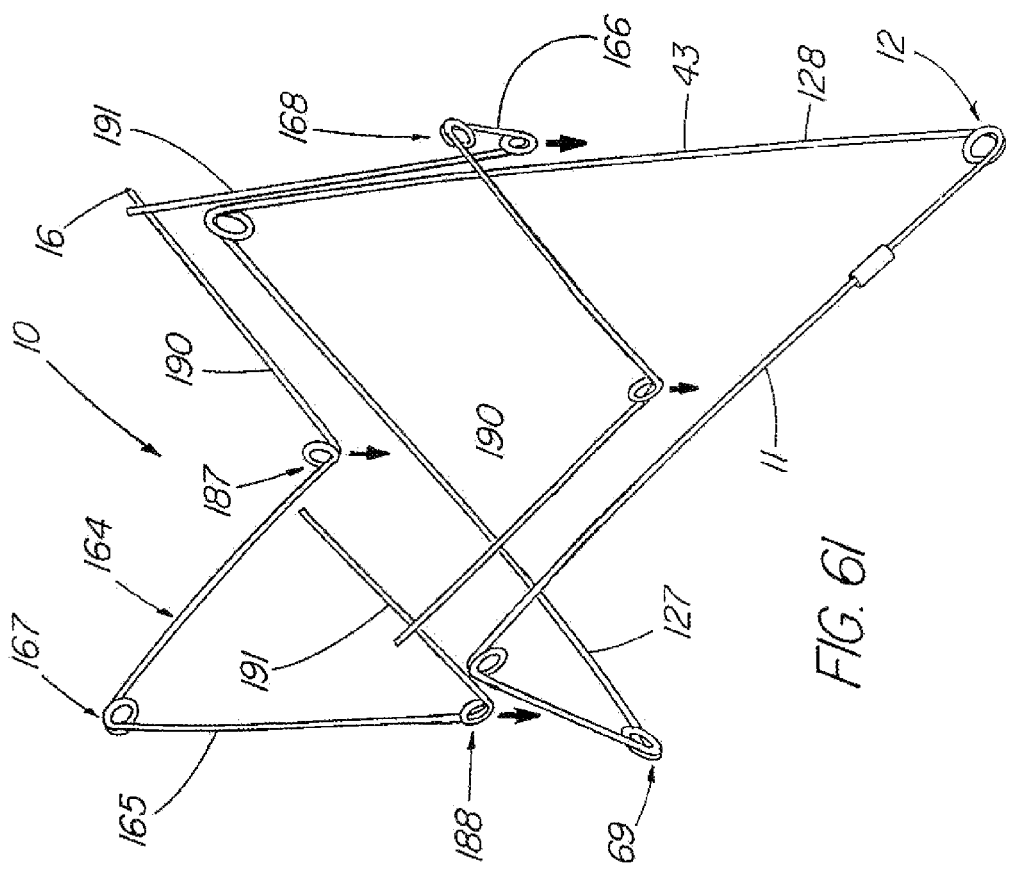

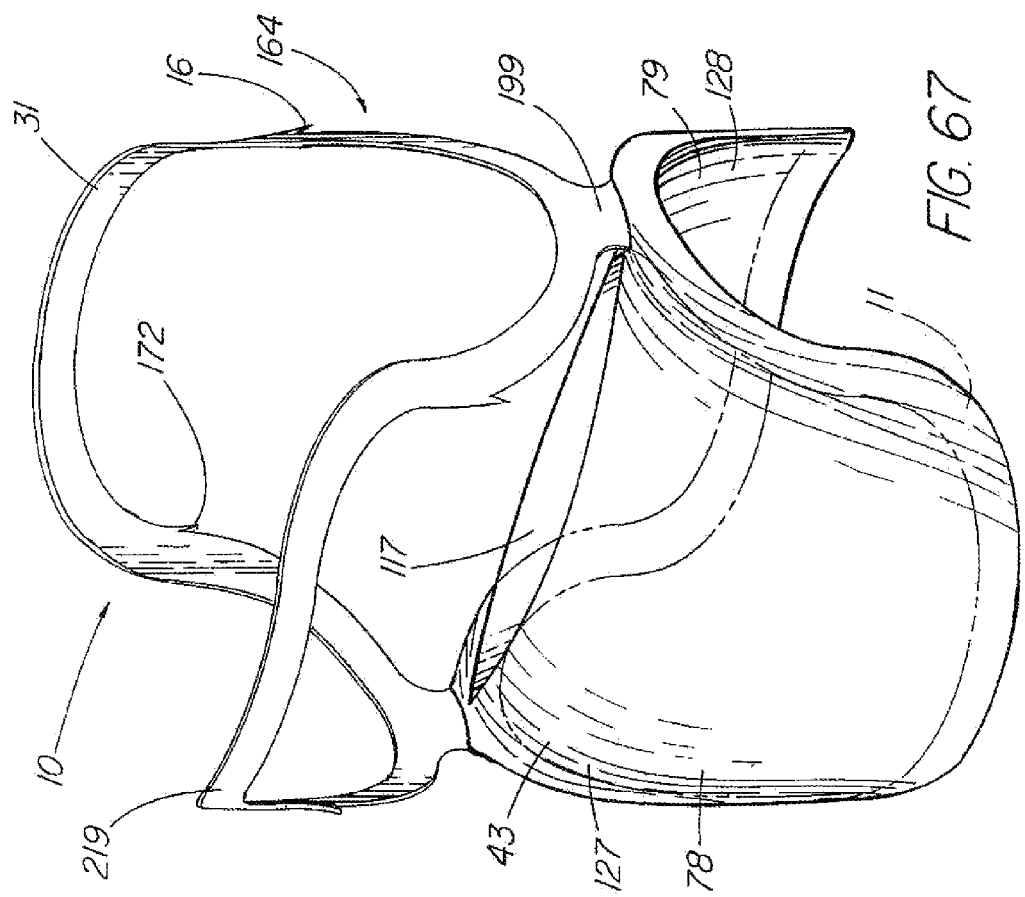
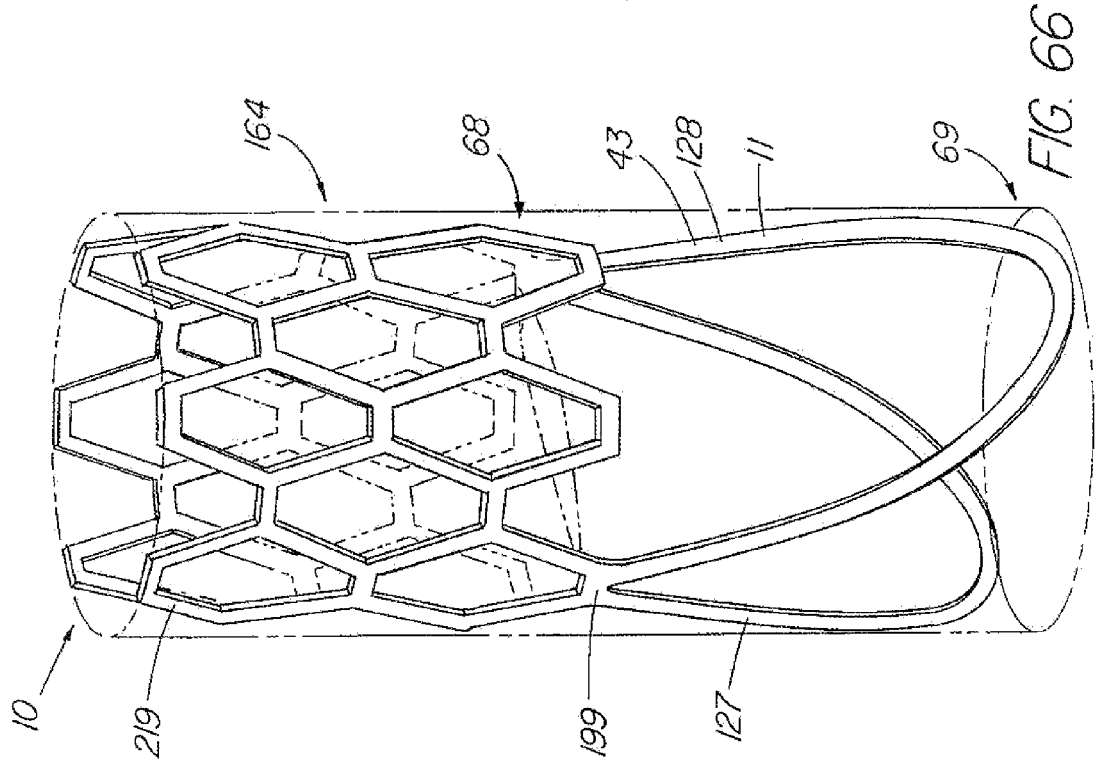

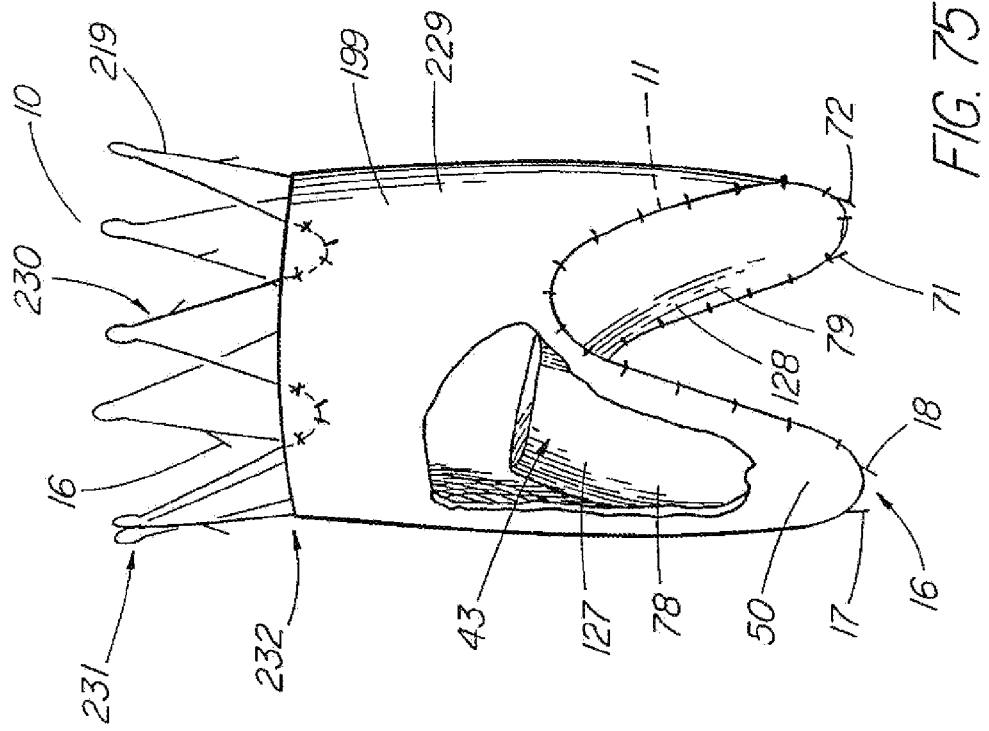
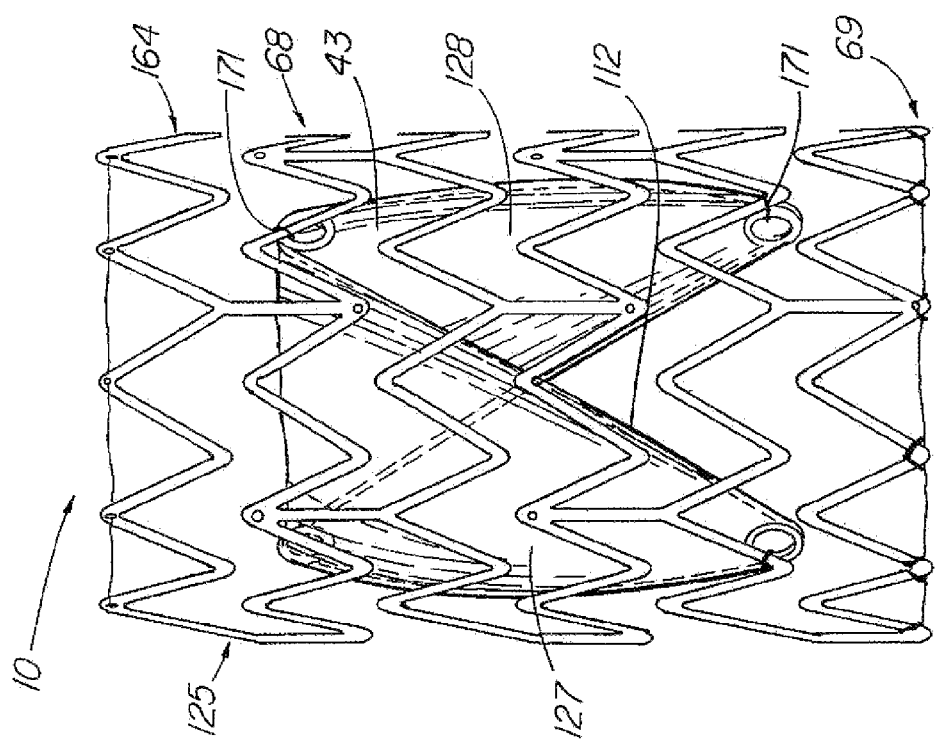

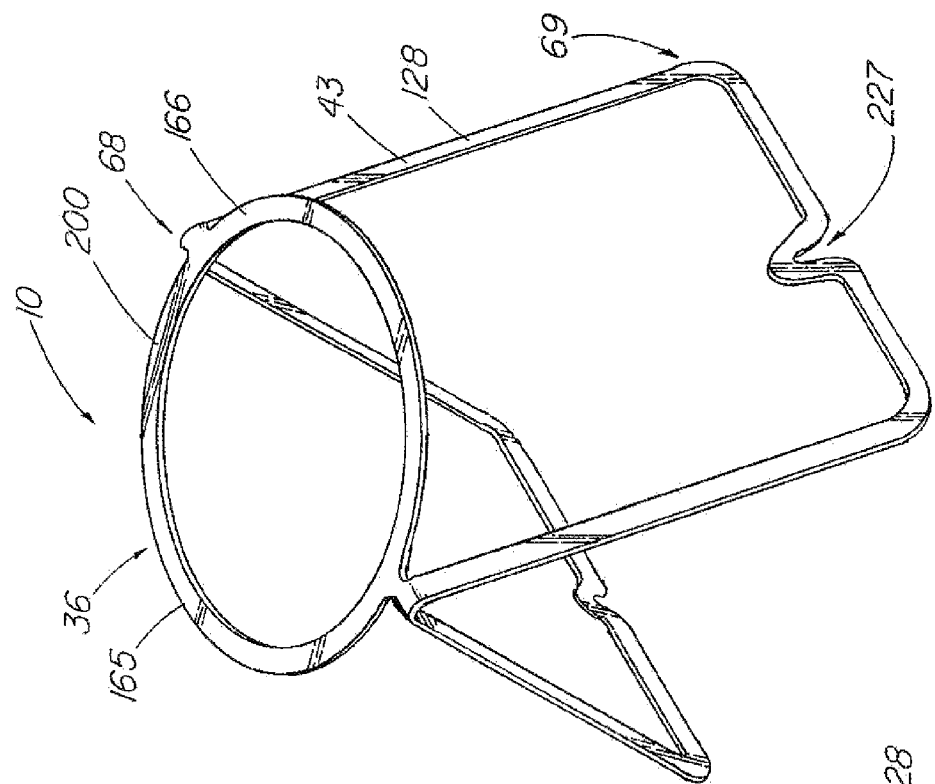
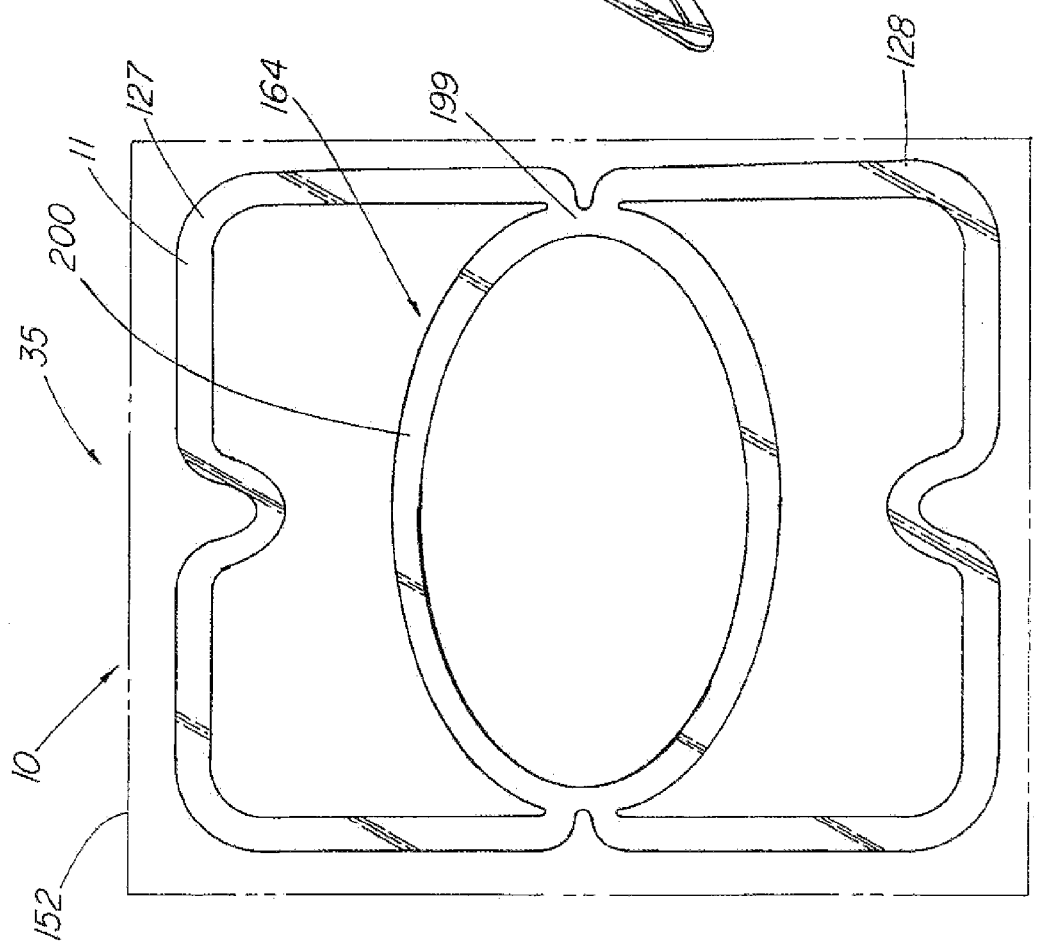

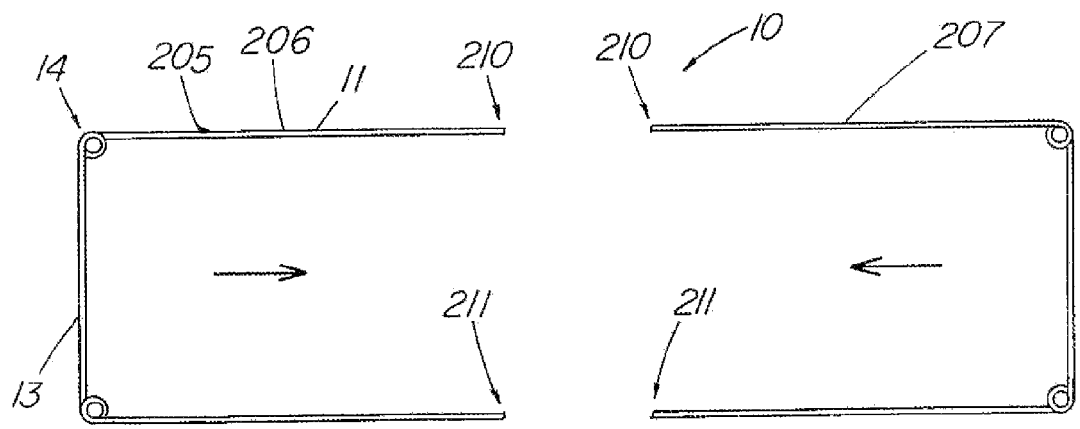
FIG. 76
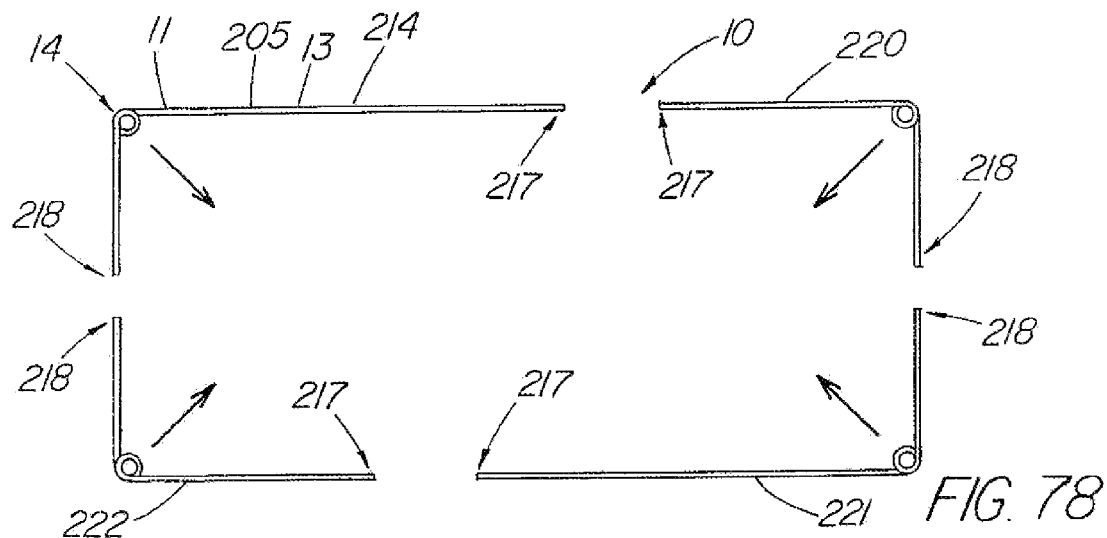
FIG. 78
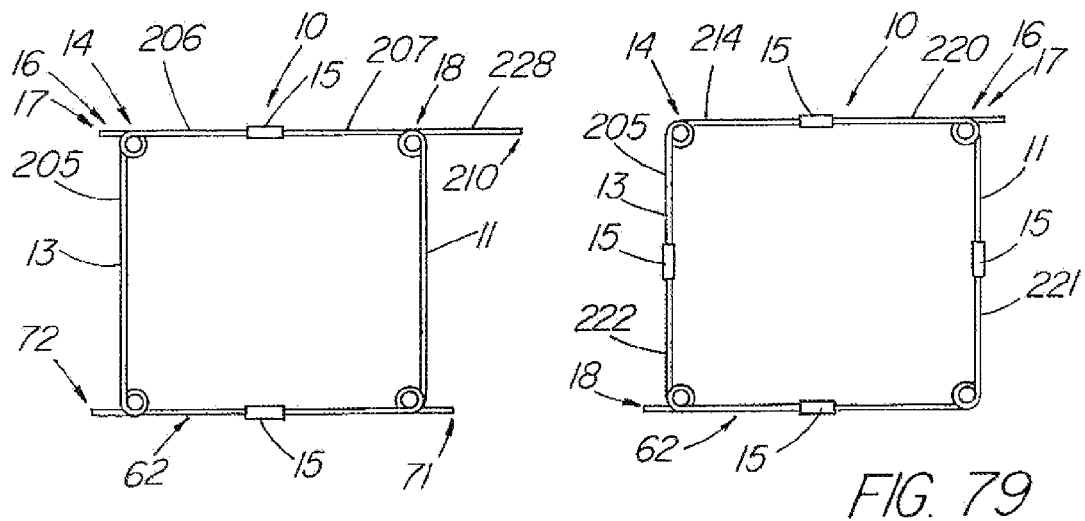
FIG. 77
FIG. 79

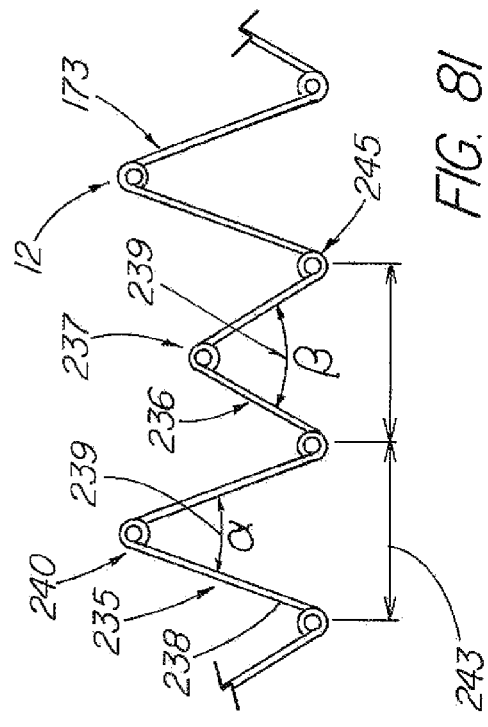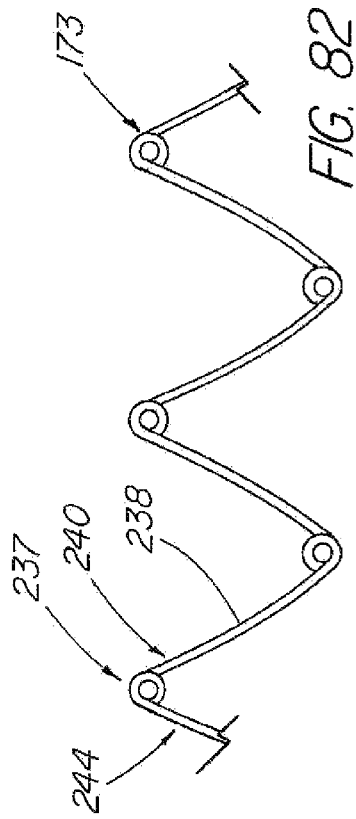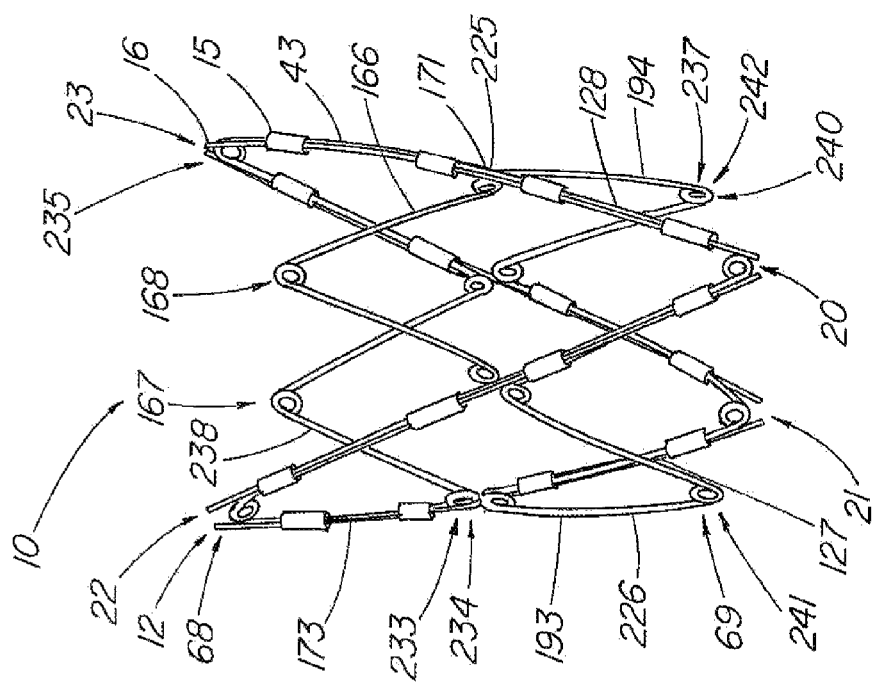

IMPLANTABLE VASCULAR DEVICE

RELATED APPLICATIONS

This application is a continuation of U. S. Application Ser. No. 10/642,372, filed on Aug. 15, 2003, which claims priority to provisional application Ser. No. 60/403,783, filed Aug. 15, 2002, and is a continuation-in-part of application Ser. No. 09/777,091, filed Feb. 5, 2001.

TECHNICAL FIELD

This invention relates to medical devices, more particularly, to intraluminal devices.

BACKGROUND OF THE INVENTION

As minimally invasive techniques and instruments for placement of intraluminal devices have developed over recent years, the number and types of treatment devices have proliferated as well. Stents, stent grafts, occlusion devices, artificial valves, shunts, etc., have provided successful treatment for a number of conditions that heretofore required surgery or lacked an adequate solution altogether. Minimally invasive intravascular devices especially have become popular with the introduction of coronary stents to the U.S. market in the early 1990s. Coronary and peripheral stents have been proven to provide a superior means of maintaining vessel patency. In addition, they have subsequently been used as filter, occluders, or in conjunction with grafts as a repair for abdominal aortic aneurysm, with fibers or other materials as occlusion devices, and as an intraluminal support for artificial valves, among other uses.

Some of the chief goals in designing stents and related devices include providing sufficient radial strength to supply sufficient force to the vessel and prevent device migration. An additional concern in peripheral use, is having a stent that is resistant to external compression. Self-expanding stents are superior in this regard to balloon expandable stents which are more popular for coronary use. The challenge is designing a device that can be delivered intraluminally to the target, while still being capable of adequate expansion. Self-expanding stents usually require larger struts than balloon expandable stents, thus increasing their profile. When used with fabric or other coverings that require being folded for placement into a delivery catheter, the problem is compounded.

There exists a need to have a basic stent, including a fabric or biomaterial covering, that is capable of being delivered with a low profile, while still having a sufficient expansion ratio to permit implantation in larger vessels, if desired, while being stable, self-centering, and capable of conforming to the shape of the vessel. There is a further need to have a intraluminal valve that can be deployed in vessels to replace or augment incompetent native valves, such as in the lower extremity venous system to treat patients with venous valve insufficiency. Such a valve should closely simulate the normal functioning valve and be capable of permanent implantation with excellent biocompatibility.

SUMMARY OF THE INVENTION

The foregoing problems are solved and a technical advance is achieved in an illustrative implantable valve that is deployed within a bodily passage, such as a blood vessel or the heart, to regulate or augment the normal flow of blood or other bodily fluids. The valve includes a covering having oppositely facing curvilinear-shaped surfaces (upper and lower) against which fluid traveling in a first or second direction within the bodily passage exerts force to at least partially open or close the valve. At least one outer edge of the covering resiliently engages and exerts force against the wall of the vessel and has arcuate shape that provides at least a partial seal against the wall.

In one aspect of the invention, the covering comprises a plurality of leaflets, each leaflet having a body extending from a wall-engaging outer edge to a free edge which is cooperable with one or more opposing leaflets to prevent flow in one direction, such as retrograde flow, while at least a portion of the leaflets having sufficient flexibility, when in situ to move apart, thereby creating a valve orifice that permits flow in the opposite direction, such as normal blood flow. The outer edge of each leaflet is adapted to engage and resilient exert force against a wall of the bodily passage such that it extends in both a longitudinal and circumferential directions along the vessel wall to at least partially seal a portion of the vessel lumen, while the free edge of each leaflet traverses the passageway across the diameter of the vessel.

In another aspect of the invention, the valve includes a frame that is covered by a piece of biocompatible material, preferably an Extracellular Collagen Matrix (ECM) such as small intestinal submucosa (SIS) or another type of submucosal-derived tissue. Other potential biomaterials include allographs such as harvested native valve tissue. The material is slit or otherwise provided with an opening along one axis to form two triangular valve leaflets over a four-sided frame. In the deployed configuration, the leaflets are forced open by normal blood flow and subsequently close together in the presence of backflow to help eliminate reflux. Other configurations include a two-leaflet valve having an oval or elliptically shaped frame, and valves having three or more legs and associated leaflets, which provide a better distribution of the load exerted by the column of fluid acting on the leaflets.

In still another aspect of the invention, the valve portion of the device, which preferably, but not essentially, includes a saddle-shaped, two-leaflet valve having a serpentine-shaped frame with the resilient outer edges of the leaflets that are sealable about entire circumference of the vessel (as depicted in FIG. 25), further includes additional centering support structure to help align the device within the vessel to prevent tilting that can compromise the performance of the valve. The centering support structure can be separate components attached to the valve portion frame, or be integrally formed with the valve portion frame (e.g., cut from the same piece of cannula).

A first series of embodiments include centering support structure that extends from the proximal end, distal end, or both ends of the valve portion. This includes, a second (or third) frame, an expandable stent, helical coil, an elongate projection or strut, an inflatable member, extended portion cut from the same cannula used to form the valve portion, or other structure that can be deployed ahead of the valve portion to provide longitudinal support, or remain within the delivery system during deployment of the valve portion, wherein the centering support structure is then also deployed. As with any of the embodiments, the prosthesis support frame, including centering support structure, can be formed from since piece of metal cannula (e.g., nitinol) or some other suitable biocompatible material by laser cutting, etching, or some other well-known method.

A second series of embodiments include centering support structure, such as a plurality of lateral elements or arms and/or supplemental legs, that extends laterally from the valve portion to provide additional contact points along the circumference of the vessel for longitudinal support, contact points being generally defined as the bends which typically supply concentrated radial force against the vessel wall (as opposed to the struts that although in contact the vessel wall, typically supply less radial force). Additionally, the lateral elements, which are preferably positioned behind the leaflets and interposed between the leaflet and vessel wall, can offer protection to the leaflets so that they are at least partially blocked and generally unable to adhere to the vessel wall, which can collapse onto the leaflets due to how the valve radially expands and conforms to the vessel. The lateral elements or arms can comprise separate components attached to the basic valve portion frame, or the frame itself can comprise multiple elements or subassemblies that can be assembled to form a closed valve portion frame with two laterally extending arms. Each lateral arm can include one contact point or additional contact points for added stability.

In another embodiment, the centering support structure comprises two lateral arms, which protect the two leaflets and provide longitudinal support, and two supplemental legs about the distal end of the valve portion for further stabilization to prevent tilting. One method of forming the frame includes attaching two zig-zag or serpentine-shaped stents end to end, with struts, sutures, or another well-known mechanism. Each zig-zag stent comprises a four or more serpentine sections with at least two opposite sections comprising either lateral arms (proximal stent) or supplemental legs (distal stent), with the other two serpentine sections on each stent comprising a half of one of the valve section legs. Strut lengths, wire diameters, eye diameters, and angles and widths of serpentine sections can be varied to produce optimum radial pressure that the device exerts on the vessel wall, depending on the size of the valve and vessel diameter. The optimal radial pressure is one at which the valve conforms to the vessel and prevents reflux without causing erosion or damage to the vessel wall that could lead to rupture.

In the double serpentine stent embodiment, the covering comprising the leaflets is attached to the frame so that each leaflet spans the two stents or serpentine row section with a lateral arm extending outward so that it is external to the leaflet and frame. In an embodiment in which the serpentine stents are attached using a long strut that also adds rigidity to the valve legs which helps prevent partial collapse due to the weight of the blood column, the ends of the struts extend beyond the bends of the valve portion frame to serve as barbs. To help prevent entanglement with the barbs during loading of the device with the delivery system, and modifying radial pressure, the adjacent lateral arms and supplemental legs can be made shorter or longer than the adjacent serpentine sections that comprise the valve legs, so that their respective contact points are offset relative to the ends of the barbs. Additionally, the struts of the serpentine sections can be curved to produce a more rounded configuration for improved conformity with the vessel. The frame can also be laser cut or otherwise formed from nitinol tubing, or some other material, to create multiple serpentine row sections (e.g., at least 2-4) interconnected by struts with the leaflets spanning multiple rows.

In another embodiment of the present invention, the valve portion is attached inside an expandable stent, or a sleeve of material, such as SIS, that is configured to provide longitudinal stability and prevent tilting. The sleeve can further include an anchoring stent about one end that is deployed ahead of, or after, the valve portion to prevent tilting of the valve.

In still another aspect of the present invention, the frame of the device is modified by placing one or more of the bends under tension which results in the frame assuming a second shape that has superior characteristics of placement within the vessel. One method of adjusting the shape includes forming the bends in the wire at an initial angle, e.g., 150°, that is larger than the desired final angle, e.g., 90° for a four-sided valve, so when the frame is constrained into the final configuration, the sides are arcuate and bow outward slightly. The curvature of the sides allows the sides to better conform to the rounded contours of the vessel wall when the valve is deployed. In devices having a full or partial covering of material over the frame, a second method of modifying the shape is to use the material to constrain the frame in one axis. One such embodiment includes a four-sided valve with two triangular-shaped halves of material, such as SIS, where the material constrains the frame in a diamond shape. This puts the bend of the frame under stress or tension which permits better positioning within the vessel. It also allows the diagonal axis of the frame with the slit or orifice to be adjusted to the optimal length to properly size the frame for the vessel such that the leaflets open to allow sufficient flow, but do not open to such a degree that they contact the vessel wall. The potential benefits of both adding tension to the bends to bow the sides and constraining the frame into a diamond shape using the covering, can be combined in a single embodiment or employed separately.

In still another aspect of the present invention, the device includes a frame that in one embodiment, is formed from a single piece of wire or other material having a plurality of sides and bends each interconnecting adjacent sides. The bends can be coils, fillets, or other configurations to reduce stress and improve fatigue properties. The single piece of wire is preferably joined by an attachment mechanism, such as a piece of cannula and solder, to form a closed circumference frame. The device has a first configuration wherein the sides and bends generally lie within a single, flat plane. In an embodiment having four equal sides, the frame is folded into a second configuration where opposite bends are brought in closer proximity to one another toward one end of the device, while the other opposite ends are folded in closer proximity together toward the opposite end of the device. In the second configuration, the device becomes a self-expanding stent. In a third configuration, the device is compressed into a delivery device, such as a catheter, such that the sides are generally beside one another. While the preferred embodiment is four-sided, other polygonal shapes can be used as well. The frame can either be formed into a generally flat configuration, or into the serpentine configuration for deployment from a single or multiple sections of wire or other material. Besides rounded wire, the frame can comprise wires of other cross-sectional shapes (e.g., oval, delta, D-shape), or flat wire. Additionally, the frame can be molded from a polymer or composite material, or formed from a bioabsorbable material such as polyglycolic acid and materials with similar properties. Another method is to laser cut the frame out of a metal tube, such as stainless steel or nitinol. Still yet another method is to spot weld together, or otherwise attach, a series of separate struts that become the sides of a closed frame. In further alternative embodiments, the frame can be left with one or more open gaps that are bridged by the material stretched over the remainder of the frame. The frame can also be formed integrally with the covering, typically as a thickened or strengthened edge portion that gives the device sufficient rigidity to allow it to assume the deployed configuration in the vessel. To prevent the frame from radially expanding within the vessel beyond the point which would be considered safe or desirable, the device can be formed into the serpentine configuration and a circumferentially constraining mechanism (or circumferential member), such as a tether, strut, sleeve, etc., placed around the device, or built into the frame, to expand or unfold during deployment of the device to limit its expansion to a given diameter, such as that which is slightly larger than the vessel into which it is placed to allow anchoring, but not permit the device to exert to great a force on the vessel wall.

In another aspect of the present invention, one or more barbs can be attached to the frame for anchoring the device in the lumen of a vessel. The barbs can be extensions of the single piece of wire or other material comprising the frame, or they can represent a second piece of material that is separately attached to the frame by a separate attachment mechanism. An elongated barb can be used to connect additional devices with the second and subsequent frames attached to the barb in a similar manner. Additional barbs can be secured to the device from cannulae placed over the frame. In embodiments in which the frame is formed as a single piece, such as when cut from a sheet of material or injection molded, the barbs can be formed as integral extensions of the frame.

In still another aspect of the present invention, a covering, which can be a flexible synthetic material such as DACRON, or expanded polytetrafluoroethylene (ePTFE), or a natural or collagen-based material, such as an allographic tissue (such as valvular material) or a xenographic implant (such as SIS), can be attached to the device with sutures or other means to partially, completely, or selectively restrict fluid flow. When the covering extends over the entire aperture of the frame, the frame formed into the second configuration functions as an vascular occlusion device that once deployed, is capable of almost immediately occluding an artery. An artificial valve, such as that used in the lower legs and feet to correct incompetent veins, can be made by covering half of the frame aperture with a triangular piece of material. The artificial valve traps retrograde blood flow and seals the lumen, while normal blood flow is permitted to travel through the device. In related embodiments, the device can be used to form a stent graft for repairing damaged or diseased vessels. In a first stent graft embodiment, a pair of covered frames or stent adaptors are used to secure a tubular graft prosthesis at either end and seal the vessel. Each stent adaptor has an opening through which the graft prosthesis is placed and an elongated barb is attached to both frames. In another stent graft embodiment, one or more frames in the second configuration are used inside a sleeve to secure the device to a vessel wall.

BRIEF DESCRIPTION OF THE DRAWINGS

FIG. 1 depicts a top view of one exemplary embodiment of the present invention;

FIG. 2 depicts a pictorial view of the embodiment of FIG. 1;

FIG. 3 depicts a top view and enlarged, partial cross-sectional views of a second exemplary embodiment of the present invention;

FIG. 17 depicts a side view of a sixth embodiment of the present invention;

FIG. 18 depicts an enlarged pictorial view of a seventh embodiment of the present invention;

FIG. 19 depicts a top view of an eighth embodiment of the present invention;

FIG. 23 depicts a side view of the embodiment of FIG. 21 when deployed in a vessel;

FIG. 24 depicts a pictorial view of the embodiment of FIG. 21 when deployed in a vessel;

FIG. 25 depicts a pictorial view of the embodiment of FIG. 21 when deployed in a vessel;

FIG. 27 depicts a pictorial view of the basic valve of FIG. 21 upon deployment with an alternative leaflet embodiment;

FIG. 42 depicts a top view of a third embodiment of an intraluminal valve;

FIG. 43 depicts a pictorial view a frame embodiment formed into a deployed configuration;

FIG. 44 depicts a top view of an embodiment of implantable valve having an integrally formed frame and covering;

FIG. 45 depicts a cross-sectional view taken along line 45-45 of FIG. 44;

FIG. 46 depicts a cross-sectional view of a second embodiment of valve having an integrally formed frame and covering;

FIG. 47 depicts a top view of an intraluminal valve embodiment having an open frame;

FIG. 48 depicts a pictorial view of an intraluminal valve embodiment that includes a circumferentially constraining mechanism;

FIG. 49 depicts a pictorial view of an intraluminal valve embodiment that includes a circumferentially constraining mechanism;

FIG. 50 depicts a top view of the embodiment of FIG. 22;

FIG. 53 depicts a pictorial view of an embodiment of the present invention that includes centering support structure comprising one or more adjoining frames or stents;

FIG. 54 depicts a pictorial view of an embodiment of the present invention that includes centering support structure comprising one or more adjoining frames or stents;

FIG. 59 depicts a pictorial view of a different frame embodiment of the basic embodiment of FIG. 58;

FIG. 60 depicts a pictorial view of a different frame embodiment of the basic embodiment of FIG. 58;

FIG. 61 depicts a pictorial view of a different frame embodiment of the basic embodiment of FIG. 58;

FIG. 65 depict a pictorial view of an embodiment of the present invention having two lateral support arms originating from each leg;

FIG. 66 depicts a pictorial view of an embodiment of the present invention wherein the valve and centering support structure are formed from a cannula;

FIG. 67 depicts a pictorial view of an embodiment of the present invention wherein the valve and centering support structure are formed from a cannula;

FIG. 68 depicts a side view of an embodiment of the present invention wherein the centering support structure comprises an expandable stent external to the valve portion;

FIG. 69 depicts a top view of an embodiment of the present invention wherein the valve and centering support structure are formed from a flat sheet of material;

FIG. 70 depicts a pictorial view of the embodiment of FIG. 69;

FIG. 75 depicts a side view of an embodiment of the present invention wherein the valve and adjoining stent are interconnected by a sleeve of material;

FIG. 76 depicts a top view of an embodiment of the present invention wherein the flat square frame is formed from multiple components;

FIG. 77 depicts a top view of an embodiment of the present invention wherein the flat square frame is formed from multiple components;

FIG. 78 depicts a top view of an embodiment of the present invention wherein the flat square frame is formed from multiple components;

FIG. 79 depicts a top view of an embodiment of the present invention wherein the flat square frame is formed from multiple components;

FIG. 80 depicts a side view of an alternative frame embodiment of the basic valve of FIGS. 62-62A;

FIG. 81 depicts a flattened, view of a stent component of the embodiment of FIG. 80;

FIG. 82 depicts an alternate embodiment of the stent component of FIG. 81;

DETAILED DESCRIPTION

Figure 11:
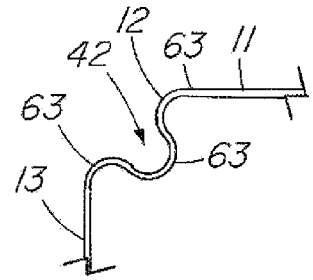
FIG. 11 depicts an enlarged partial view of another embodiment of the present invention.
Figure 12:
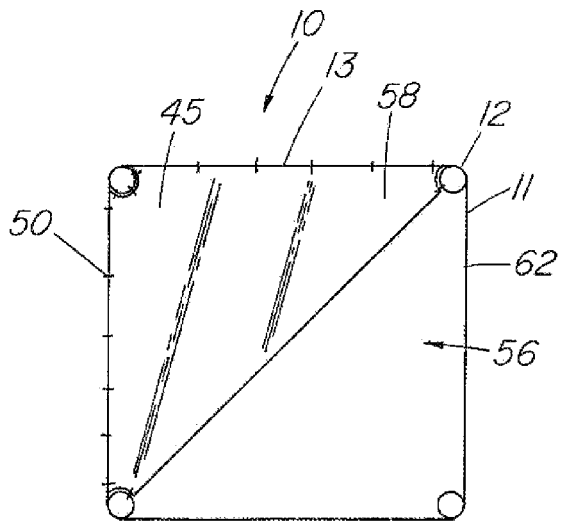
FIG. 12 depicts a top view of a fourth embodiment of the present invention.
Figure 15:
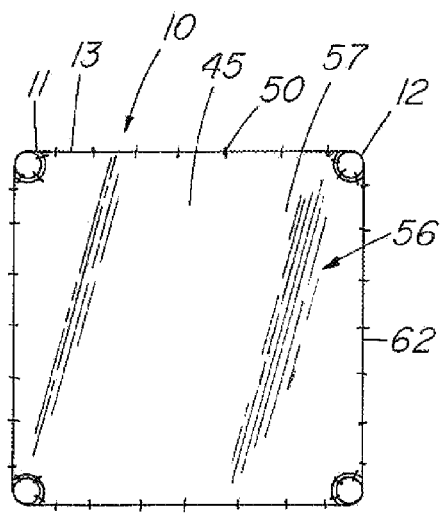
FIG. 15 depicts a top view of a fifth embodiment of the present invention.
Figure 13:
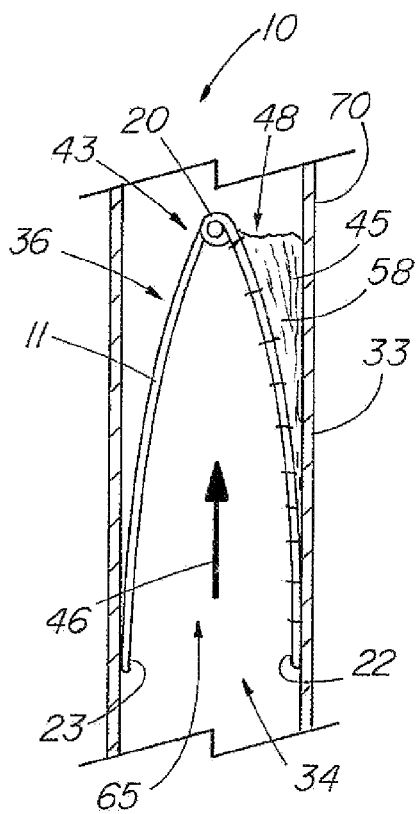
FIG. 13 depicts a side view of the embodiment of FIG. 12.
Figure 14:
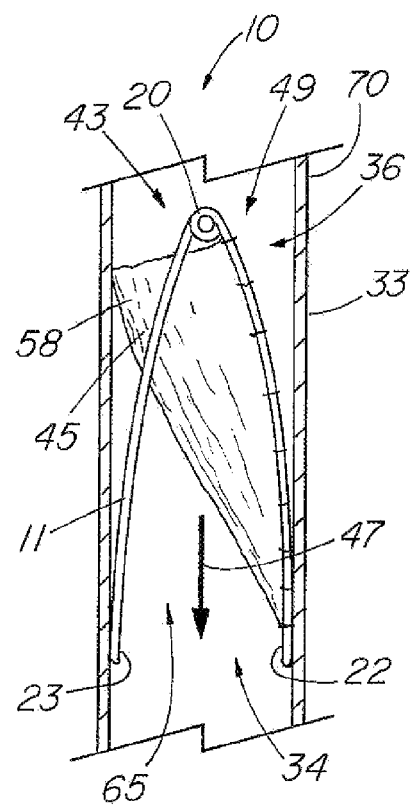
FIG. 14 depicts a side view of the embodiment of FIG. 12.
Figure 16:
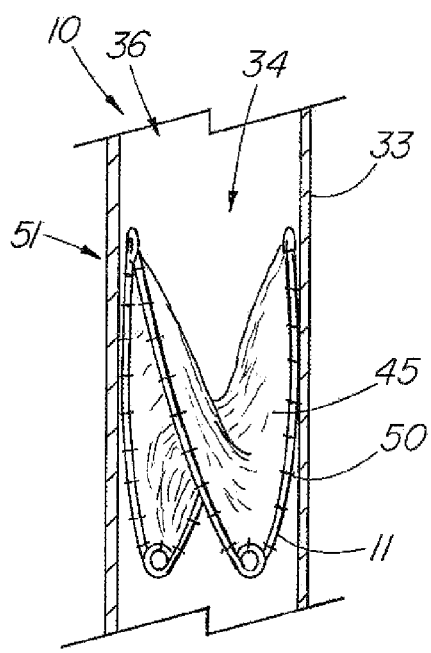
FIG. 16 depicts a side view of the embodiment of FIG. 15.

The invention is further illustrated by the following (preceding) pictorial embodiments, which in no way should be construed as further limiting. The present invention specifically contemplates other embodiments not illustrated but intended to be included in the appended claims. FIGS. 1-11, 18-19 are directed to a basic stent frame; FIGS. 12-14 are directed to a single-leaflet valve; FIGS. 15-16 are directed to an occluder (or filter); FIGS. 17 and 32 are directed to a stent adaptor for a stent graft, FIG. 20-27, 35-40, 42-50 are directed to a multi-leaf valve; and FIG. 28-31 are directed to a constrained frame which can be used to form any of the other embodiments.

Figure 9:
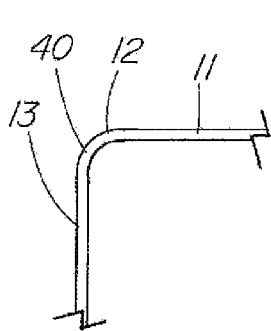
FIG. 9 depicts an enlarged partial view of another embodiment of the present invention.
Figure 10:
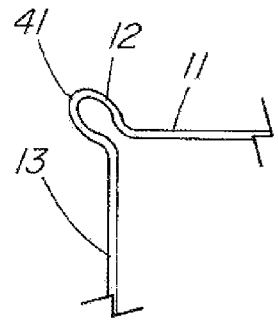
FIG. 10 depicts an enlarged partial view of another embodiment of the present invention.

FIG. 1 depicts a top view of one embodiment of the medical device 10 of the present invention comprising a frame 11 of resilient material, preferably metal wire made of stainless steel or a superelastic alloy (e.g., nitinol). While round wire is depicted in each of the embodiments shown herein, other types, e.g., flat, square, triangular, D-shaped, delta-shaped, etc. may be used to form the frame. In the illustrative embodiment, the frame comprises a closed circumference 62 of a single piece 59 of material that is formed into a device 10 having a plurality of sides 13 interconnected by a series of bends 12. The depicted embodiment includes four sides 13 of approximately equal length. Alternative embodiments include forming a frame into any polygonal shape, for example a pentagon, hexagon, octagon, etc. One alternative embodiment is shown in FIG. 19 that includes a four-sided frame 11 having the general shape of a kite with two adjacent longer sides 66 and two adjacent shorter sides 67. In the embodiment of FIG. 1, the bends 12 interconnecting the sides 13 comprise a coil 14 of approximately one and a quarter turns. The coil bend produces superior bending fatigue characteristics than that of a simple bend 40, as shown in FIG. 9, when the frame is formed from stainless steel and most other standard materials. The embodiment of FIG. 9 may be more appropriate, however, if the frame is formed from nitinol (NiTi) or other superelastic alloys, as forming certain type of bends, such as coil 14, may actually decrease fatigue life of a device of superelastic materials. Therefore, the bend 12 should be of a structure that minimizes bending fatigue. Alternative bend 12 embodiments include an outward-projecting fillet 41 as shown in FIG. 10, and an inward-projecting fillet 42 comprising a series of curves 63, as shown in FIG. 11. Fillets are well known in the stent art as a means to reduce stresses in bends. By having the fillet extend inward as depicted in FIG. 11, there is less potential trauma to the vessel wall.

When using stainless steel wire, the size of the wire which should be selected depends on the size of device and the application. An occlusion device, for example, preferably uses 0.010" wire for a 10 mm square frame, while 0.014" and 0.016" wire would be used for 20 mm and 30 mm frames, respectively. Wire that is too stiff can damage the vessel, not conform well to the vessel wall, and increase the profile of the device when loaded in the delivery system prior to deployment.

Returning to FIG. 1, the single piece 59 of material comprising the frame 11 is formed into the closed circumference 62 by securing the first and second ends 60,61 with an attachment mechanism 15 such as a piece of metal cannula. The ends 60,61 of the single piece 59 are then inserted into the cannula 15 and secured with solder 25, a weld, adhesive, or crimping to form the closed frame 11. The ends 60,61 of the single piece 59 can be joined directly without addition of a cannula 15, such as by soldering, welding, or other methods to join ends 61 and 62. Besides joining the wire, the frame could be fabricated as a single piece of material 59, by stamping or cutting the frame 11 from another sheet (e.g., with a laser), fabricating from a mold, or some similar method of producing a unitary frame.

A alternate method of forming the frame 11 of the present invention is depicted in FIGS. 76-79, whereby rather than one continuous length of wire being used, the frame 11 comprises a two or more sub-portions 205 that include an attachment 15 such as a weld, solder, glue, crimping with the illustrative cannula 15, or another means, or combination thereof, to form a closed circumference 62. In the embodiment depicted in FIG. 76-77, a first and a second C-shaped sub-portion 206, 207 are overlaid such that first ends 210 of the C-shaped sub-portion 206,207 extend beyond the adjoining sub-portion to form a barb 16 for anchoring the device 10 within the vessel. As shown in FIG. 77, the assembled frame 11 includes four barbs that either represent the ends 210,211 of the sub-portions 206,207, or are formed by cutting away excess material 228 from the ends, depending on how the sides 13 of the C-shaped portions are sized.

FIGS. 78-79 depict an alternative embodiment using sub-portions 205 to assemble a closed frame, whereby there are four L-shaped sub-portions 214,220,221,222 with attachments at each of the four sides 13 that make up the closed circumference 62. In the illustrative embodiments only two of the ends 217 are used to form barbs 17,18; however, additional barbs can be formed by lengthening any leg of the L-shaped sub-portion 214,220,221,222 such that it extends beyond the closed circumference 62. Other configurations are possible in addition to those depicted, for example, having three sub-portions 205 or even more than four if making a frame having more than four sides.

Figure 34:
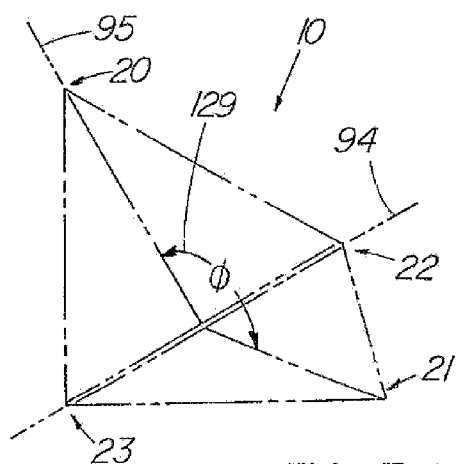
FIG. 34 depicts a pictorial view of the present invention having returned to the first configuration following formation into the second configuration.

The device 10 depicted in FIG. 1 is shown in its first configuration 35 whereby all four bends 20,21,22,23 and each of the sides 13 generally lie within a single flat plane. To resiliently reshape the device 10 into a second configuration 36, shown in FIG. 2, the frame 11 of FIG. 1 is folded twice, first along one diagonal axis 94 with opposite bends 20 and 21 being brought into closer proximity, followed by opposite bends 22 and 23 being folded together and brought into closer proximity in the opposite direction. The second configuration 36, depicted in FIG. 2, has two opposite bends 20,21 oriented at the first end 68 of the device 10, while the other opposite bends 22,23 are oriented at the second end 69 of the device 10 and rotated approximately 90° with respect to bends 20 and 21 when viewed in cross-section. The medical device in the second configuration 36 can be used as a stent 44 to maintain an open lumen 34 in a vessel 33, such as a vein, artery, or duct. The bending stresses introduced to the frame 11 by the first and second folds required to form the device 10 into the second configuration 36, apply force radially outward against the vessel wall 70 to hold the device 10 in place and prevent vessel closure. Absent any significant plastic deformation occurring during folding and deployment, the device in the second configuration 36, when not with the vessel or other constraining means, will at least partially return to the first configuration 25, although some deformation can occur as depicted in FIG. 34, depending on the material used. It is possible to plastically form the stent into this configuration which represents an intermediate condition between the first configuration (which it also can obtain) and the second configuration. It is also possible to plastically deform the device 10 into the second configuration 36, such that it does not unfold when restraint is removed. This might be particularly desired if the device is made from nitinol or a superelastic alloy.

Figure 6:
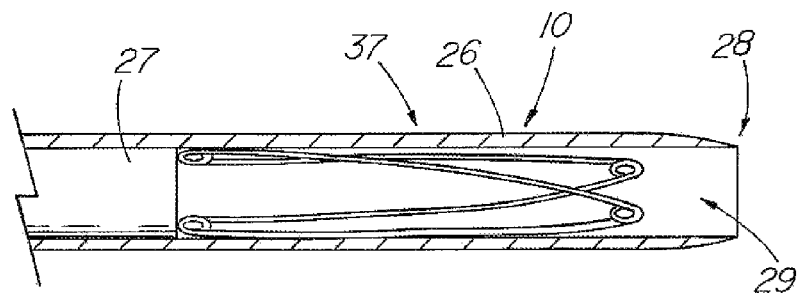
FIG. 6 depicts a partially-sectioned side view of the embodiment of FIG. 1 inside a delivery system.

The standard method of deploying the medical device 10 in a vessel 33, depicted in FIG. 6, involves resiliently forming the frame 11 into a third configuration 37 to load into a delivery device 26, such as a catheter. In the third configuration 37 the adjacent sides 13 are generally beside each other in close proximity extending generally along the same axis. To advance and deploy the device from the distal end 28 of the delivery catheter 26, a pusher 27 is placed into the catheter lumen 29. When the device 10 is fully deployed, it assumes the second configuration 36 within the vessel as depicted in FIG. 2. The sides 13 of the frame, being made of resilient material, conform to the shape of the vessel wall 70 such that when viewed on end, the device 10 has a circular appearance when deployed in a round vessel. As a result, sides 13 are arcuate or slightly bowed out to better conform to the vessel wall.

A second embodiment of the present invention is depicted in FIG. 3 wherein one or more barbs 16 are included to anchor the device 10 following deployment. As understood, a barb can be a wire, hook, or any structure attached to the frame and so configured as to be able to anchor the device 10 within a lumen. The illustrative embodiment includes a first barb 16 with up to three other barbs 17,71,72, indicated in dashed lines, representing alternative embodiments. As depicted in detail view A of FIG. 3, the barb combination 38 that comprises barbs 17 and 18, each barb is an extension of the single piece 59 of material of the frame 11 beyond the closed circumference 59. The attachment cannula 15 secures and closes the single piece 59 of material into the frame 11 as previously described, while the first and second ends 60,61 thereof, extend from the cannula 15, running generally parallel with the side 13 of the frame 11 from which they extend, each preferably terminating around or slightly beyond respective bends 20,23. To facilitate anchoring, the distal end 19 of the barb 16 in the illustrative embodiment contains a bend or hook.

Figure 4:
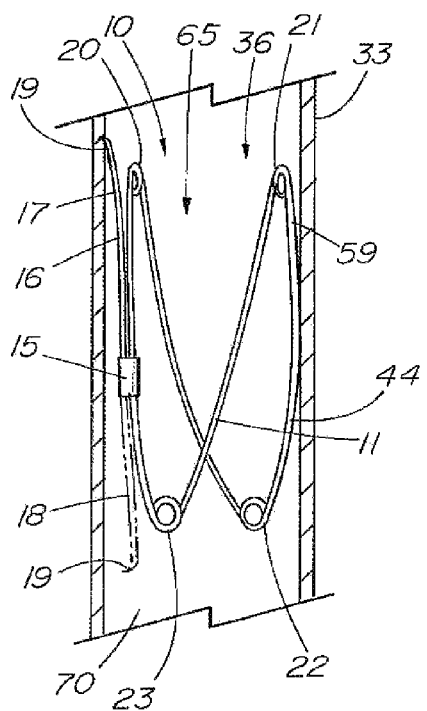
FIG. 4 depicts a side view of the embodiment of FIG. 3 deployed in a vessel.
Figure 5:
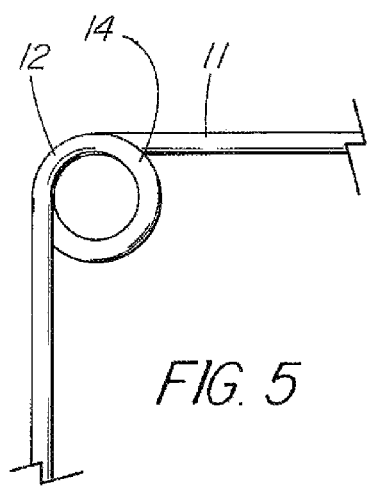
FIG. 5 depicts a enlarged partial view of the embodiment of FIG. 1.

Optionally, the tip of the distal end 19 can be ground to a sharpened point for better tissue penetration. To add a third and fourth barb as shown, a double ended barb 39 comprising barbs 71 and 72 is attached to the opposite side 13 as defined by bends 21 and 22. Unlike barb combination 38, the double barb 39, as shown in detail view B of FIG. 3, comprises a piece of wire, usually the length of barb combination 38, that is separate from the single piece 59 comprising the main frame 11. It is secured to the frame by attachment mechanism 15 using the methods described for FIG. 1. FIG. 4 depicts barb 17 (and 18) engaging the vessel wall 70 while the device 10 is in the second, deployed configuration 36. While this embodiment describes up to a four barb system, more than four can be used.

Figure 7:
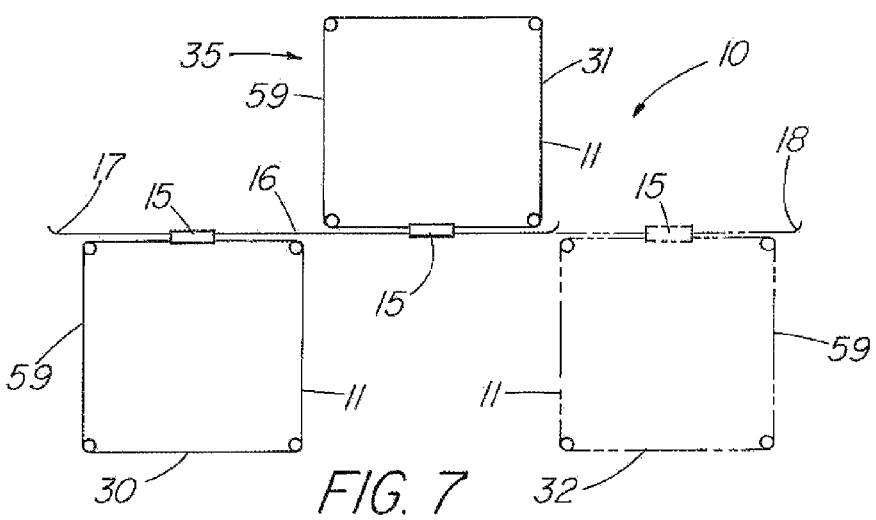
FIG. 7 depicts a top view of a third embodiment of the present invention.
Figure 8:
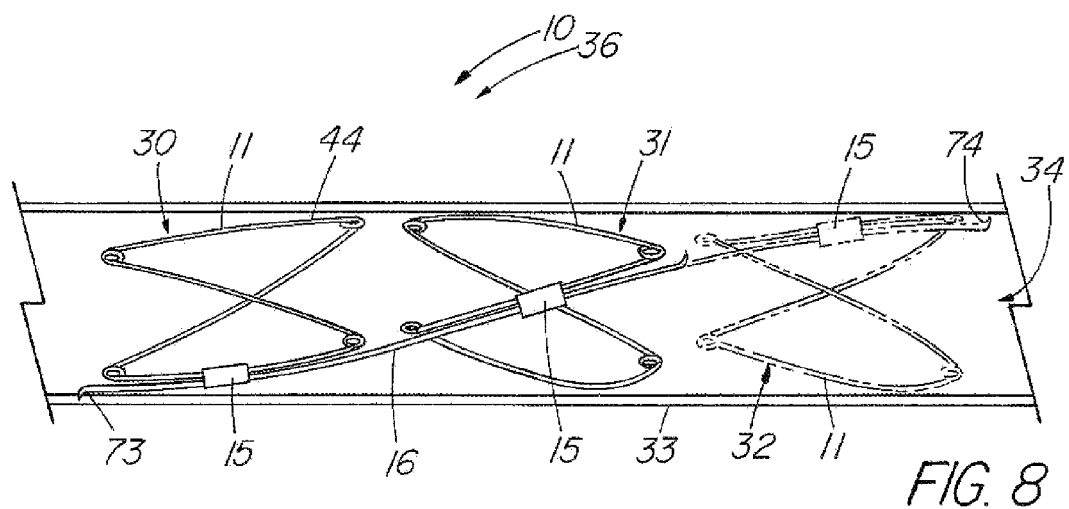
FIG. 8 depicts a side view of the embodiment of FIG. 7 deployed in a vessel.

FIG. 7 depicts a top view of a third embodiment of the present invention in the first configuration 35 that includes a plurality of frames 11 attached in series. In the illustrative embodiment, a first frame 30 and second frame 31 are attached by a barb 16 that is secured to each frame by their respective attachment mechanisms 15. The barb 16 can be a double-ended barb 39 as shown in FIG. 3 (and detail view B) that is separate from the single pieces 59 comprising frames 30 and 31, or the barb may represent a long extended end of the one of the single pieces 59 as shown in detail view A of FIG. 3. Further frames, such as third frame 32 shown in dashed lines, can be added by merely extending the length of the barb 16. FIG. 8 depicts a side view of the embodiment of FIG. 7 in the second configuration 36 as deployed in a vessel 33.

FIGS. 12-18 depict embodiments of the present invention in which a covering 45 comprising a sheet of fabric, collagen (such as small intestinal submucosa), or other flexible material is attached to the frame 11 by means of sutures 50, adhesive, heat sealing, "weaving" together, crosslinking, or other known means. FIG. 12 depicts a top view of a fourth embodiment of the present invention while in the first configuration 35, in which the covering 45 is a partial covering 58, triangular in shape, that extends over approximately half of the aperture 56 of the frame 11. When formed into the second configuration 36 as shown in FIGS. 13-14, the device 10 can act as an artificial valve 43 such as the type used to correct valvular incompetence. FIG. 13 depicts the valve 43 in the open configuration 48. In this state, the partial covering 58 has been displaced toward the vessel wall 70 due to positive fluid pressure or flow in a first direction 46, e.g., normal venous blood flow, thereby opening a passageway 65 through the frame 11 and the lumen 34 of the vessel 33. As the muscles relax, producing flow in a second, opposite direction 47, e.g., retrograde blood flow 47, as shown in FIG. 14, the partial covering 58 acts as a normal valve by catching the backward flowing blood and closing the lumen 34 of the vessel. In the case of the artificial valve 43, the partial covering 58 is forced against the vessel wall to seal off the passageway 65, unlike a normal venous valve which has two leaflets, which are forced together during retrograde flow. Both the artificial valve 43 of the illustrative embodiment and the normal venous valve, have a curved structure or cusp that facilitates the capture of the blood and subsequent closure. In addition to the triangular covering, other possible configurations of the partial covering 58 that result in the cupping or trapping of fluid in one direction can be used. Selecting the correct size of valve for the vessel ensures that the partial covering 58 properly seals against the vessel wall 70. If the lumen 34 of the vessel is too large for the device 10, there will be retrograde leakage around the partial covering 58.

FIG. 15 depicts a top view of a fifth embodiment of the present invention in the first configuration 35, whereby there is a full covering 57 that generally covers the entire aperture 56 of the frame 11. When the device 10 is formed into the second configuration 36, as depicted in FIG. 16, it becomes useful as an occlusion device 51 to occlude a duct or vessel, close a shunt, repair a defect, or other application where complete or substantially complete prevention of flow is desired. As an intravascular device, studies in swine have shown occlusion to occur almost immediately when deployed in an artery or the aorta with autopsy specimens showing that thrombus and fibrin which had filled the space around the device. The design of the present invention permits it to be used successfully in large vessels such as the aorta. Generally, the occlusion device should have side 13 lengths that are at least around 50% or larger than the vessel diameter in which they are to be implanted.

FIGS. 17-18 depict two embodiments of the present invention in which the device 10 functions as a stent graft 75 to repair a damaged or diseased vessel, such as due to formation of an aneurysm. FIG. 17 shows a stent graft 75 having a tubular graft prosthesis 54 that is held in place by a pair of frames 11 that function as stent adaptors 52,53. Each stent adaptor 52,53 has a covering attached to each of the frame sides 13 which includes a central opening 55 through which the graft prosthesis 54 is placed and held in place by friction or attachment to prevent migration. One method of preventing migration is placement of a stent adaptor 52,53 according to the present invention at each end and suturing the graft prosthesis 54 to the covering of the stent adaptors 52,53. The stent adaptors 52,53 provide a means to seal blood flow while centering the graft prosthesis in the vessel. A long double-ended barb 39 connects to each stent adaptor 52,53 and assists to further anchor the stent graft 75. In the embodiment depicted in FIG. 18, the covering 45 comprises a outer sleeve 64 that is held in place by first and second 30,31 frames that function as stents 44 to hold and seal the sleeve 64 against a vessel wall and maintain an open passageway 65. In the illustrative embodiment, the stents 44 are secured to the graft sleeve 64 by sutures 50 that are optionally anchored to the coils 14 of the bends 12. If the embodiment of FIG. 18 is used in smaller vessels, a single frame 11 can be used at each end of the stent graft 75. Another stent graft 75 embodiment is depicted in FIG. 32 for repairing a vessel defect 97, such as an aneurysm in a bifurcated vessel. The stent adaptor 52 of the present invention is placed in the common vessel 96 such as the abdominal aorta. Two tubular grafts 54 are secured within an aperture 55 in the covering 45 of the frame 11 by one or more internal stent adapters 102, or another type of self-expanding stent, that bias the opening of the grafts 54 against the surrounding covering 45 to provide an adequate seal. Each leg 98,99 of the stent graft prosthesis 75 transverses the vessel defect 97 and feeds into their respective vessel branches 100, 101 such the right and left common iliac arteries. As with the embodiment of FIG. 17, a second stent adapter 53 can be used to anchor the other end of the tubular graft 54 in each vessel branch 100,101.

FIGS. 20-27 and 35-41 depict embodiments of present inventions in which the device 10 comprises an implantable valve having multiple leaflets 25 that act together to regulate and augment the flow of fluid through a duct or vessel 33, or within the heart to treat patients with damaged or diseased heart valves. The covering 45 of each of these embodiments includes one or a series of partial coverings 58 that form the leaflets 25 of the valve. As with the other embodiments, the covering 45 may comprise a biomaterial or a synthetic material. While DACRON, expanded polytetrafluoroethylene (ePTFE), or other synthetic biocompatible materials can be used to fabricate the covering 45, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater. SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (Nov. 1999); Cook et al., WIPO Publication WO 98/22158, dated 28 May 1998, which is the published application of PCT/US97/14855. Irrespective of the origin of the valve material (synthetic versus naturally occurring), the valve material can be made thicker by making multilaminate constructs, for example SIS constructs as described in U.S. Pat. Nos. 5,968,096; 5,955,110; 5,885,619; and 5,711,969. Animal data show that the SIS used in venous valves of the present invention can be replaced by native tissue in as little as a month's time. In addition to xenogenic biomaterials, such as SIS, autologous tissue can be harvested as well, for use in forming the leaflets of the valve. Additionally Elastin or Elastin Like Polypetides (ELPs) and the like offer potential as a material to fabricate the covering or frame to form a device with exceptional biocompatibility. Another alternative would be to used allographs such as harvested native valve tissue. Such tissue is commercially available in a cryopreserved state.

To more completely discuss and understand the multi-leaflet valve 43 embodiments of FIGS. 20-27,35-41, it is useful to now add certain supplemental terminology which in some instances, could be applied to the embodiments depicted in the earlier figures. In the illustrative multi-leaflet embodiments, the valve 43 is divided into a plurality of legs 113, each of which further comprises a leaflet 25. To anchor, support, and provide the proper orientation of the leaflets 25, a separate or integral frame 11 is included, such as the wire frame 11 depicted in FIG. 1. Ideally, the wire used to construct the frame is made of a resilient material such as 302,304 stainless steel; however, a wide variety of other metals, polymers, or other materials are possible. It is possible for the frame to be made of the same material as the leaflets 25. One other example of a suitable frame material would be a super-elastic alloy such as nitinol (NiTi). Resiliency of the frame 11, which provides radial expandability to the valve 43 when in the second configuration 36 for deployment, is not necessarily an essential property of the frame. For example, optional barbs 16 can provide the means to anchor the valve 43 after delivery, even if the valve 43 lacks sufficient expansile force to anchor itself against the vessel wall. Additionally, the frame can comprise a ductile material with the device 10 being designed to be balloon expandable within the vessel.

Typically, when used as a valve to correct venous insufficiency in the lower extremities, the valve 43 in situ comprises a plurality of bends 12 of the frame, that provide the majority of the outward radial force that helps anchor the device to vessel wall 70, as depicted in FIGS. 22-27. When deployed, the frame assumes the undulating or serpentine configuration characteristic of the invention with a first series of bends 115 of the first or proximal end alternating with a second series of bends 116 of the second or distal end, with the second or distal bends 116 being located at the bottom of the valve distal to the heart and the first or proximal bends 115 being located at the top of the valve proximal to the heart. It should be understood that the valve can assume other orientations, depending on the particular clinical use, and thus, any directional labels used herein ('distal', 'top', etc.) are merely for reference purposes. The leaflet 25, which generally covers the valve leg 113 and therefore, assumes the same roughly triangular 'U' or 'V' shape of that portion of the frame 11 perimeter, includes an resilient arcuate outer edge 112 that conforms to and/or seals with the contours of the vessel wall 70, and an inner edge 111 that traverses the vessel lumen 34. The central portion or body 156 of the leaflet 25 extends inward from the vessel wall 70 and outer edge 112 in an oblique direction toward the first end 68 of the valve 43 where it terminates at the inner edge 111 thereof. The valve leaflets that come in contact with the vessel wall carry the supporting frame along the outer edge to better conform to and directly seal with the vessel wall. The leaflets 25 assume a curvilinear shape when in the deployed configuration 36. The portion of the body 156 proximate the inner edge 111 is sufficiently flexible such that is can move in and out of contact with the inner edge 111 the opposite or other leaflets 25; however, the remainder of the body 156, particular that near the outer edge 112 or second end 69 of the device 10, can be made less flexible or even rigid in some instances, essentially functioning more for support, similar to the function of the frame 11, rather than to cooperate with other leaflet(s) 25.

Figure 20:
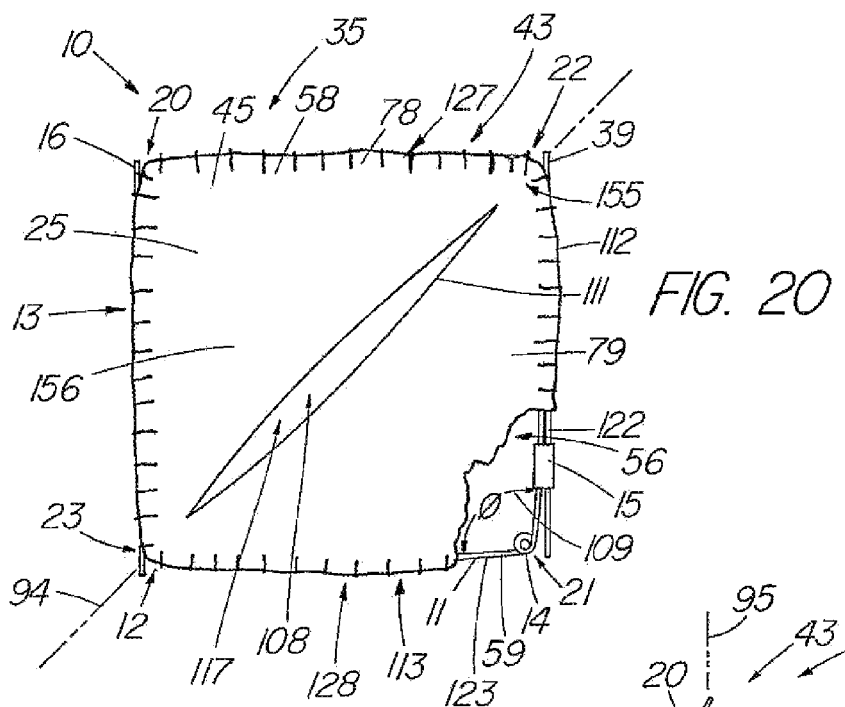
FIG. 20 depicts a top view of a first embodiment of a multi-leaflet intraluminal valve of the present invention.

FIGS. 20-27 depict the present invention as an implantable, intraluminal, vascular adapted for use as a implantable multi-leaflet valve 43 including a stent 44 or frame 11 with at least a partial covering 58. The covering comprises a first and a second valve leaflets 78,79 that at least partially seal the aperture 56 within the frame 11 while the valve 43 is in the deployed configuration 36 and forms the opening 117 or valve orifice which regulates the flow of fluid 46,47 through the valve. FIG. 20 shows the device 10 in the first, generally planar configuration 35 where the frame 11 is generally rectangular or in particular square in shape. The partial covering 58 forming the leaflets 78,79 generally extends across the entire frame 11 with the aperture 56 comprising a slit 108 that extends across the first axis 94 of the frame 11, the first axis being defined as traversing diagonally opposite bends (22 and 23 in this example) that are in line with the valve orifice 117 that forms the valve 43. The covering 45 is therefore divided into at least first and second portions (making it a partial covering 58) which define the first and second valve leaflets 78,79. To form the leaflets 78,79, a complete covering 45 can be slit open along the axis after it is affixed to the frame, or at least first and second adjacent triangular portions (partial coverings 58) can be separately attached, eliminating the need for mechanically forming a slit 108. In the embodiment of FIG. 20, the slit 108 is made in the covering 45 such that the slit terminates a few millimeters from each of the corner bends 22,23, creating a pair of corner gaps 155, thereby eliminating two of the most likely sources of leakage around the valve 43. In the illustrative embodiments, the outer edge 112 of the partial covering 58 that comprises the leaflet 25 is stretched over the frame 11 comprising the valve leg 113 and sutured or otherwise attached as disclosed herein. The leaflet 25 is secured in place such that the material is fairly taut, such that when the valve 43 is situated in the vessel 33 and its diameter constrained to slightly less than the valve width 146, the leaflet 25 assumes a relatively loose configuration that gives it the ability to flex and invert its shape, depending on the direction of fluid flow. The inner edge 111 of the leaflet 25 is generally free and unattached to the frame and generally extends between the bends 22 and 23 (the bends 115 of the first end) of the valve leg 113. The inner edge 111 may be reinforced by some means, such as additional material or thin wire, that still would allow it to be sufficiently pliable to be able to seal against another leaflet 25 when retrograde flow 47 forces the leaflets 78,79 together. The leaflet 25 is sized and shaped such that the inner edge 111 of one leaflet 78 can meet or overlap with the inner edge 111 of the opposing leaflet 79 (or leaflets, e.g., 119,120), except when degree of normal, positive flow 46 is sufficient to force the leaflets 25 open to permit fluid passage therethrough.

Figure 21A:
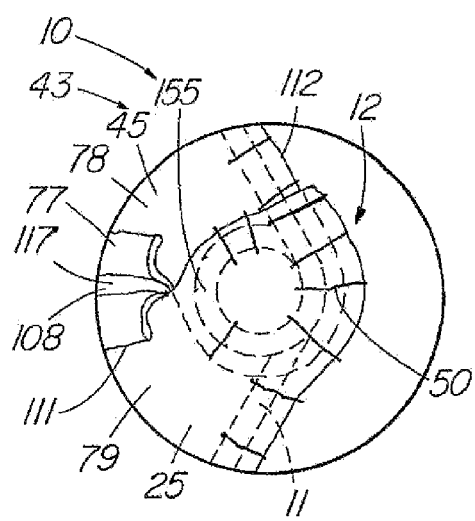
FIG. 21A depicts a partial top view of another embodiment of leaflets of the present invention.
Figure 21:
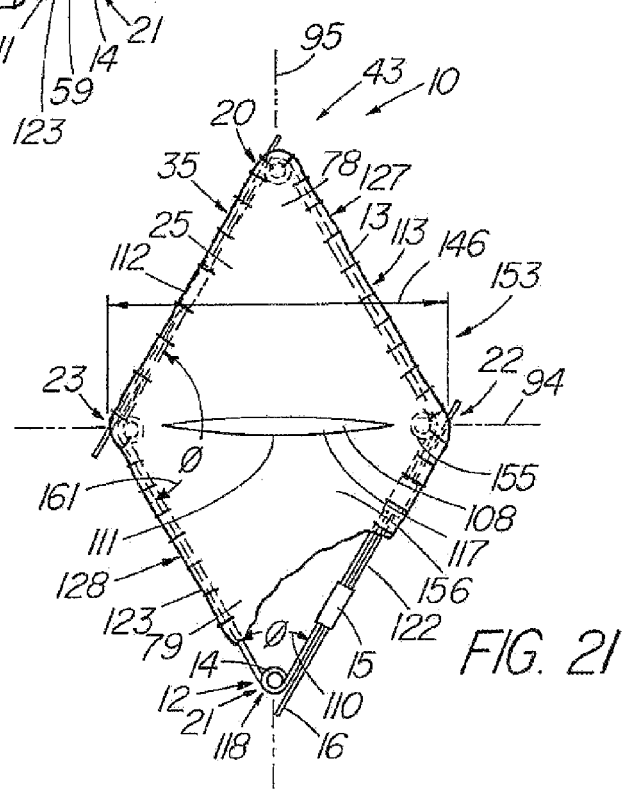
FIG. 21 depicts a top view of a second embodiment of a multi-leaflet intraluminal valve.
Figure 22:
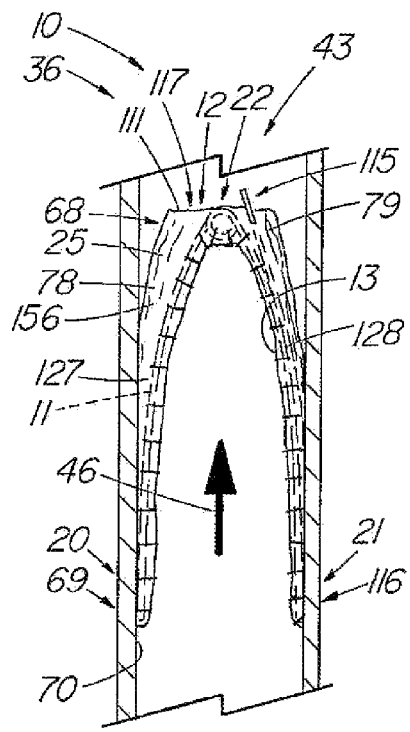
FIG. 22 depicts a side view of the embodiment of FIG. 21 when deployed in a vessel.

The embodiments of FIGS. 21-27 are configured into an elongated diamond shape 153 in the planar configuration 35 with the distance between the two bends 22,23 aligned with the valve orifice 117 and first axis 94 being less than the distance between bends 20 and 21 along the second, perpendicular axis 95. This diamond configuration 153 can be accomplished by forming the frame 11 into that particular shape, or constraining a square frame into a diamond shape 153, which will be discussed later. By configuring the valve 43 into the diamond shape 153, the valve legs 127,128 become more elongated in shape, which can help add stability when positioning the device 10 during deployment, provides more surface area to receive retrograde flow, and more closely mimics a natural venous valve. In the deployed configuration 36 of the embodiment of FIG. 21, which is shown in FIGS. 22-25, the valve leaflets 78,79 are forced apart by the normal pulsatile blood flow 46 (FIGS. 22,24). The respective valve leaflets 78,79 naturally move back into closer proximity following the pulse of blood. Retrograde blood flow 47 forces the valve leaflets 78,79 against one another, as depicted in FIGS. 23 and 25 thereby closing off the lumen 34 of the vessel 33 and the valve orifice 117.

Figure 21B:
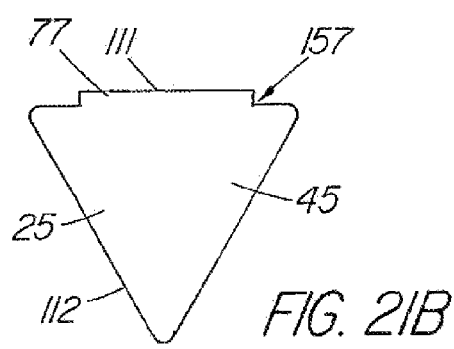
FIG. 21B depicts a top view of another embodiment of leaflet of the present invention.

FIGS. 21A-21B depict embodiments of the valve 43 in which each leaflet 78,79 includes a flap 77 of overhanging material along the slit edge 111 to provide advantageous sealing dynamics when the valve 43 is in the deployed configuration 36 as depicted in FIGS. 22-25. The flaps 77 are typically formed by suturing two separate pieces of covering 45 material to the frame such that the inner edge 111 is extendable over the slit 108 and inner edge 111 of the adjacent leaflet 25. By overlapping with an adjacent flap 77 or leaflet 25, the flap 77 can provide additional means to help seal the valve orifice 117. Two embodiments of leaflets 25 with flaps 77 are shown. In FIG. 21A, the inner edge 111 is basically straight and extends over the first axis 94 of the frame 11. The flaps 77 can be cut to create a corner gap 155 that covers and seals the corner region around the bend 22,23. In the embodiment of FIG. 21B, the flap 77 is cut such that there is a notch 157 in the leaflet where the leaflet meets the corner bends 22,23. While these flaps 77 may provide benefit in certain embodiments, the optional flaps 77 shown in FIG. 21 are not necessary to provide a good seal against backflow 47 if the valve 43 and leaflets 25 are properly sized and configured.

Figure 26A:
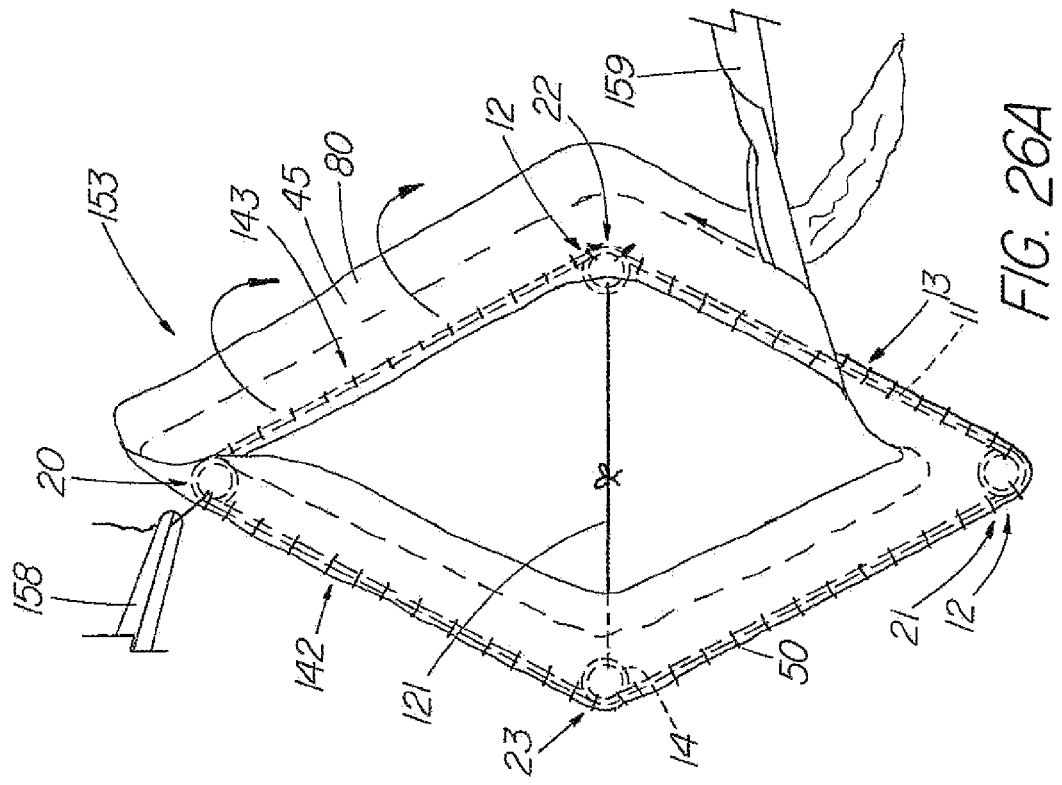
FIG. 26A depicts the method of attaching the covering to the embodiment of FIG. 21.
Figure 26:
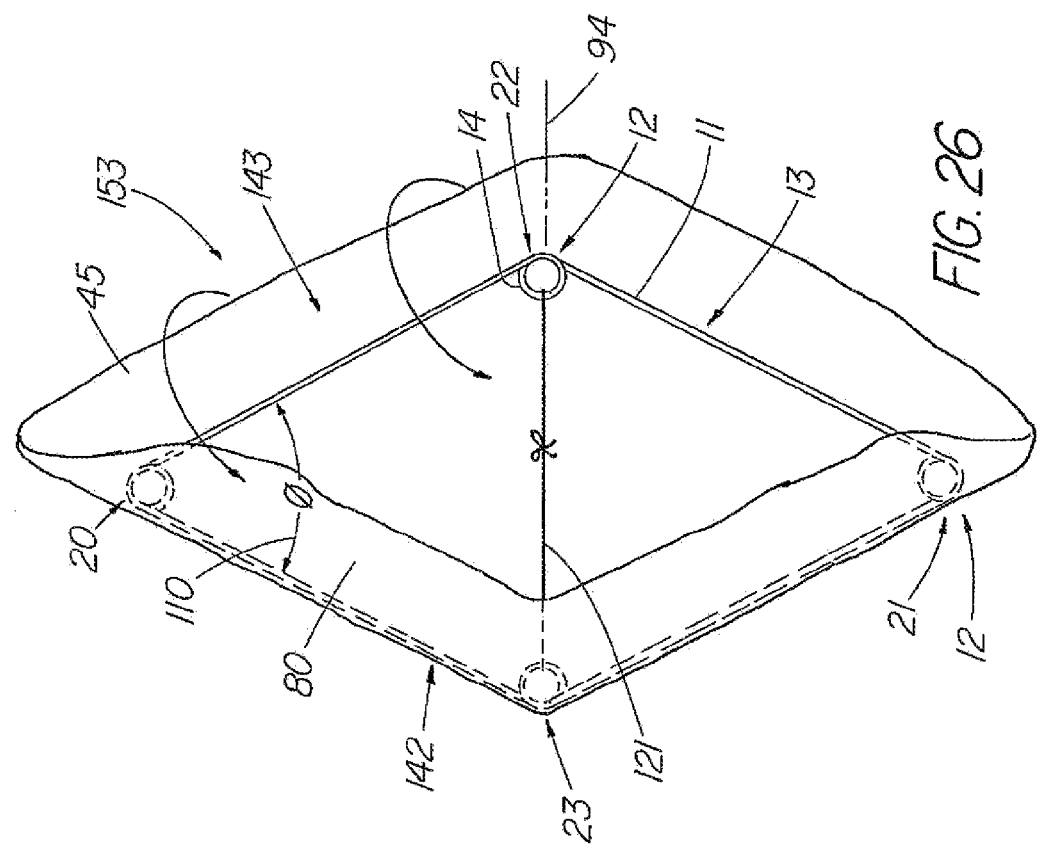
FIG. 26 depicts the method of attaching the covering to the embodiment of FIG. 21.

FIGS. 26-26A depict one method of affixing a covering 45 comprising a biomaterial, such as SIS, to the frame 11 which has been constrained using a temporary constraining mechanism 121, such as a suture, to achieve the desired frame configuration. As shown in FIG. 26, the covering 45 is cut larger than the frame 11 such that there is an overhang 80 of material therearound, e.g., 5-10 mm. The frame 11 is centered over the covering 45 and the overhang 80 is then folded over from one long side 142, with the other long side 143 subsequently being folded over the first. As shown in FIG. 26A, the covering 45 is sutured to the frame along one side 142, typically using forceps 158 and needle, thereby enclosing the frame 11 and the coiled eyelet 14 with the overhang 80 along side 142. The covering 45 is sutured to the frame with resorbable or non-resorbable sutures 50 or some other suitable method of attaching two layers of biomaterials can be used. In the case of SIS, a single ply sheet, usually about 0.1 mm thick, is used in the hydrated condition. In the illustrative embodiments, 7-0 Prolene suture is used, forming a knot at one bend (e.g., bend 20), then continuing to the next bend (e.g., 22) with a running suture 50, penetrating the layers of SIS around the frame at about 1-2 mm intervals with loops formed to hold the suture 50 in place. When the next coil turn 14 is reached, several knots are formed therethrough, and the running suture 50 continues to the next coil turn 14. If barbs are present, such as shown in the embodiment of FIG. 21, the suture 50 is kept inside of the barbs 16 located about each coil turn 14. In the illustrative example, the covering 45 is affixed to the frame 11 such that one side of the overhang 80 is not sutured over the other side in order to maintain the free edge of the overhang 80, although the alternative condition would be an acceptable embodiment. Alternative attachment methods include, but are not limited to, use of a biological adhesive, a cross-linking agent, heat welding, crimping, and pressure welding. For synthetic coverings, other similar methods of joining or attaching materials are available which are known in the medical arts. The covering 45, whether made from a biomaterial or synthetic material, can be altered in ways that improve its function, for example, by applying a coating of pharmacologically active materials such as heparin or cytokines, providing a thin external cellular layer, e.g., endothelial cells, or adding a hydrophilic material or other treatment to change the surface properties.

Once the covering 45 has been sutured into place or otherwise attached to the frame, the overhang 80 is folded back away from the frame, as shown on the second side 143 of the frame of FIG. 26A, and part of the excess overhang 80 is trimmed away with a scalpel 159 or other cutting instrument to leave a 2-4 mm skirt around the frame 11. The overhang 80 or skirt provides a free edge of SIS (or material with similar remodeling properties) to help encourage more rapid cell ingrowth from the vessel wall, such that the SIS replaces native tissue as quickly as possible. An unattached edge of the overhang 80 can also form a corner flap 81 or pocket as depicted in FIG. 27. This corner flap 81 can serve to catch retrograde blood flow 47 to provide a better seal between the device 10 and the vessel wall 70 as well as providing an improved substrate for ingrowth of native intimal tissue from the vessel 33, if made of SIS or another material with remodeling properties.

Figure 29:
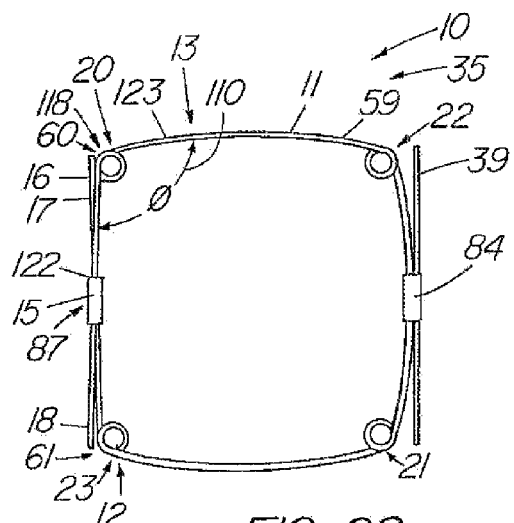
FIG. 29 depicts a top view of an embodiment of the present invention, made using the method shown in FIG. 28.
Figure 30:
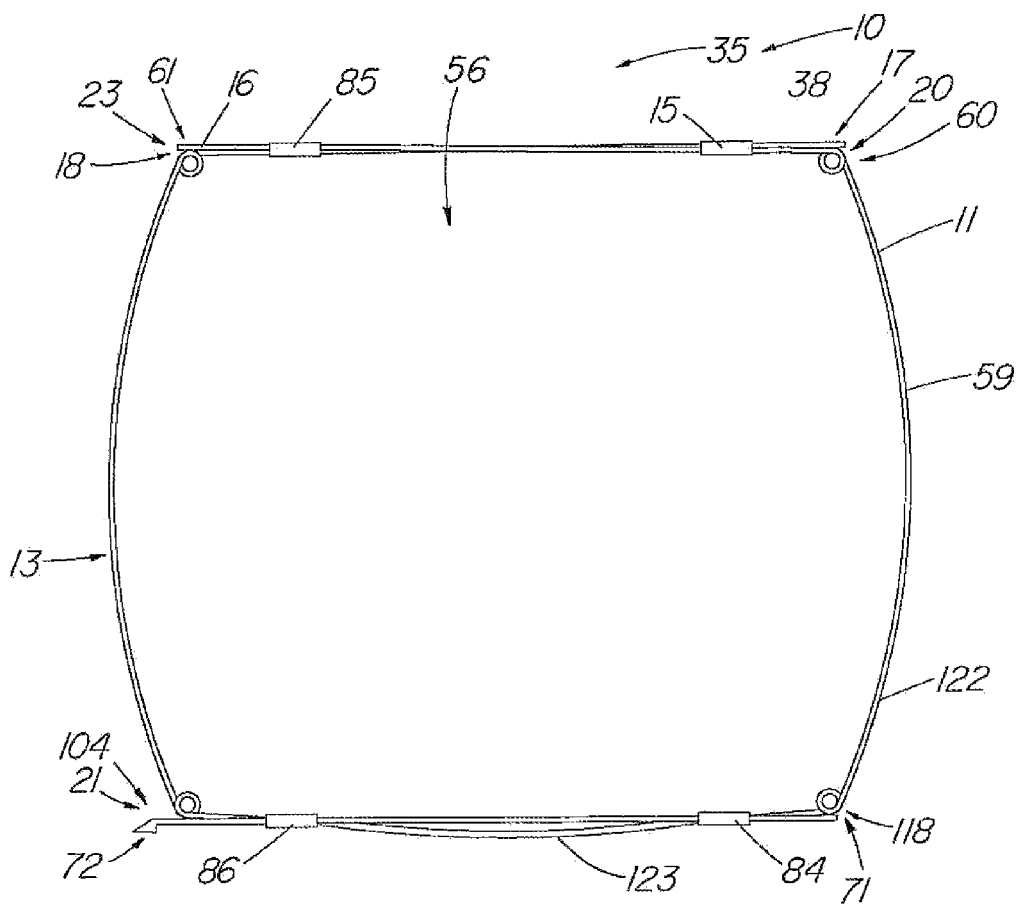
FIG. 30 depicts a top view of an embodiment of the present invention, made using the method shown in FIG. 28.

Referring now to FIGS. 28-31, the frame 11 used to form the valve 43 embodiments, e.g., FIGS. 20-27, that are placed in the legs or other deep veins as replacement for incompetent venous valves, is sized according to the size of the target vessel. For example, a typical venous valve might be made of 0.0075" 304 stainless steel mandril wire with an attachment mechanism 15 comprising 23 to 24 gauge thin-wall stainless steel cannula or other tubing. Larger wire (e.g., 0.01") and attachment cannula 15 are typically used for valves 43 of the larger diameter (greater than 15 mm). Selection of the attachment cannula 15 depends on competing factors. For example, use of larger gauge attachment cannula 15 results in a slightly increased device 10 profile, yet it includes additional room for flux when the attachment mechanism 15 is soldered over the continuous wire 59 comprising the frame 11. FIG. 30 best depicts an uncovered frame 11 used to form a venous valve 43, wherein the length of the sides 13 typically range from about 15 to 25 mm. For larger frames, heavier gauge wire is typically used. For example, 25 mm frames might use 0.01" wire, with larger diameter embodiments such as stent occluders used for femoral bypass or stent adaptors, such as shown in FIGS. 17 and 32, requiring an even heavier gauge. The appropriate gauge or thickness of the frame wire also depends on the type of alloy or material used. As previously disclosed, the frame is typically formed in a generally flat configuration and then manipulated into its characteristic serpentine configuration and loaded into a delivery system. Therefore, the frame usually will tend to reassume the first or generally flat configuration if the restraint of the delivery system or vessel is removed. Deformation of the frame 11 can occur after it has been manipulated into the second configuration, however, such that it no longer will lie completely flat, as depicted in FIG. 34. This angle of deformation 129, which varies depending on the frame thickness and material used, generally does not compromise the function of the device 10, which can be reconfigured into the serpentine configuration (of the second, deployed configurations) without loss of function.

Figure 41A:
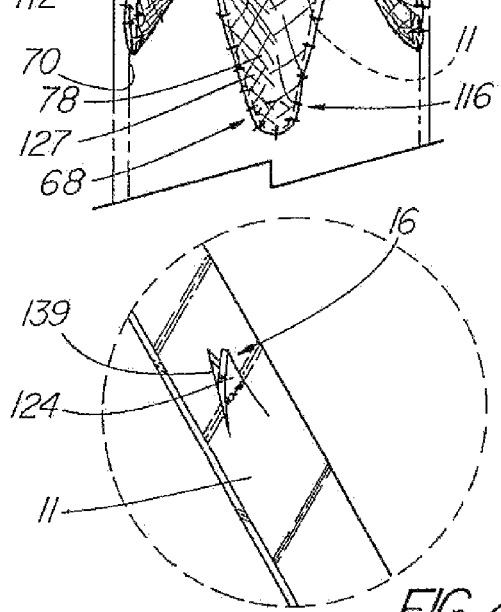
FIG. 41A depicts a detail view of the embodiment of FIG. 41.
Figure 41:
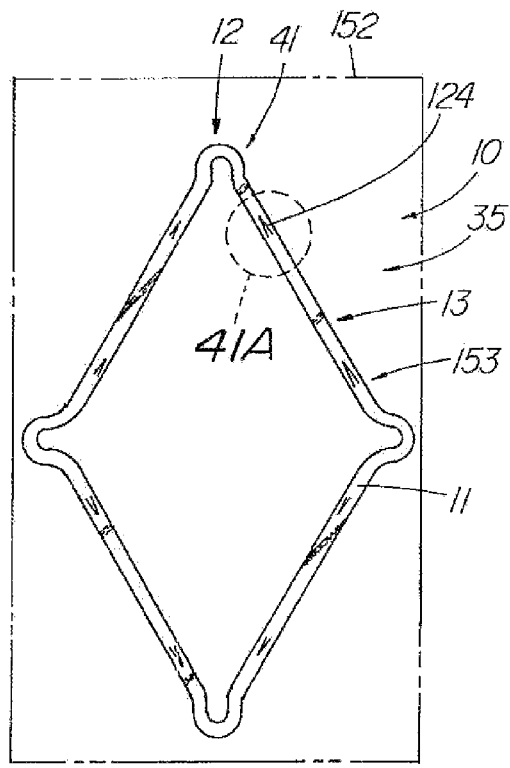
FIG. 41 depicts a top view of a frame formed from a sheet of material.

The frame 11 of the present invention can be made either by forming a series of bends in a length of straight wire and attaching the wire to itself, as previously discussed, to form a closed configuration, or the frame 11 can be formed in the deployment (second) configuration 35 as depicted in FIGS. 41-41A by cutting it out of a flat sheet 152 of material, e.g., stainless steel or nitinol. Further finishing procedures can then be performed after it has been cut or formed, such as polishing, eliminating sharp edges, adding surface treatments or coatings, etc. In addition to metal, the frame 11 can comprise one or more polymers, composite materials, or other non-metallic materials such as collagen with the frame either being cut from a thin sheet of the material, or molded into the deployment configuration 36 as depicted in FIG. 43. Unlike the majority of the depicted embodiments, the frame 11 of FIG. 43 does not naturally assume a flattened configuration 35 when the device 10 is unconstrained by the vessel or delivery system.

The illustrative embodiments of FIGS. 41-41A and 43 include integral barbs 124 that extend from the frame 11, which being formed as a closed frame, does not have free ends 60,61 that can be used to serve as barbs 16 as depicted in FIG. 3 and other embodiments. FIGS. 41-41A depict a series of integral barbs 124 comprising V-shaped cuts 139 transversing the thickness of the flat metal frame 11, which are bent outward to form the barb 16. In the embodiment of FIG. 43, the integral barbs 124 are formed along with the frame 11 with two extending from the frame at either side of each bend 12. These integral barbs 124 can be designed into the mold if the frame 11 is formed out of a polymer material. The number, arrangement, and configuration of the integral barbs 124 is generally not critical and can vary according to design preference and the clinical use of the device. The barbs 16 may or may not penetrate the covering, depending on their design and other factors, including the thickness and type of covering used.

While the frame embodiment of FIG. 43 can be formed from a variety of medical grade polymers having properties that permit the frame to function as a supporting structure for the valve leaflets 78,79, it should be noted that for some uses, it may be desirable to form the frame 11 from a material that can be degraded and adsorbed by the body over time to advantageously eliminate a frame structure can would remain in the vessel as a foreign body and that could possibly fracture and/or cause perforation of the vessel wall. A number of bioabsorbable homopolymers, copolymers, or blends of bioabsorbable polymers are known in the medical arts. These include, but are not necessarily limited to, poly-alpha hydroxy acids such as polyactic acid, polylactide, polyglycolic acid, or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived bioabsorbable polymers that may be suitable, including modified polysaccharides such as cellulose, chitin, and dextran or modified proteins such as fibrin and casein.

FIGS. 44-46 depicts two exemplary embodiments in which the frame 11 is integral with the covering 45. In the embodiment of FIG. 44, the valve 43 is formed as a single piece of material, such as a flexible polymeric or collagen-based material, whereby there is a thin, compliant central portion comprising the covering 45 or leaflets 78,79, and a thickened edge 141 portion that comprises the frame 11. The valve 43, shown in the generally flat configuration 35, can be also formed into the deployment configuration 36 (see FIG. 43). Optionally, the material of the frame 11 portion can be subjected to treatments or processes that add rigidity or other desired characteristics that permit the frame to better support the covering 45 portion or anchor the device 10 to the vessel wall. As with the embodiment of FIG. 43, optional integral barbs 124 can be included along the frame 11. In addition to forming a thickened edge 141 to serve as the frame 11, other layers of different materials can be laminated to or blended with the edge portion to provide the desired properties. As another alternative to the thickened edge 141 portion of FIGS. 44-45, the outside edge 112 of the covering 45 can be folded over itself to form a rolled edge 140 (FIG. 46) that adds rigidity to serve as a frame 11. The rolled edge 140 can be held in placed with a glue, resin, or similar bonding agent 144. For example, the covering 45 and rolled edge 140 can comprise a sheet of SIS with a bonding agent 144 such as collagen glue or other bioabsorbable material used to secure the rolled portion and after hardening, to add the necessary degree of rigidity for the valve 43 (or occluder, filter, stent adaptor, etc.) to assume the deployment configuration within the vessel. Excess of the bonding agent 144 can be fashioned to structural elements that can serve to help anchor the device 10 within the vessel. It is also within the scope of the invention to eliminate a discernable frame 11 by changing the material or material properties along the outer edge 112 of the leaflets, by adding or incorporating one or more different material or agents along the outer edge 112 of covering 45 such that the stiffness and/or resiliency increased, thereby allowing the frame to hold a desired shape during deployment, while still allowing the adjacent covering material to be sufficiently flexible to function as a leaflet 25. If the illustrative valve 43 lacks the radial expandability to anchor itself to the vessel wall, it may be mounted on a balloon to expand the valve 43 and anchor the barbs, if present, into the vessel wall.

The illustrative embodiments of the present invention generally include a closed frame 11 to give the device 10 its form. FIG. 47 depicts an example in which the frame 11 portion is not a closed structure. Rather, a portion of the covering 45 used to span a gap 145 in the frame such that a portion of the outside edge 112 (of leaflet 79 in this example) is unsupported therealong. The length of the gaps 145 and their distribution can vary as long as the frame 11 is still able to fulfill its role to support and define the shape of the valve 43 or device 10.

FIGS. 21-31 depict various embodiments in which the bends 20,21,22,23 are placed in a resiliently tensioned or stressed state after being initially formed such that the bends were not under tension. The term 'tension', as used herein, is meant to describe generally a forced applied to a resilient material or structure against the natural tendency of the material or structure, whether or not the force is in fact tensile, compression, or torsional. Further incremental forces applied will generally encounter greater resistance than would otherwise be exhibited by the material or structure, such as a compression spring, which exerts a force (resilience) resisting compression proportional to the distance the spring has already been compressed. The addition of tension to one or more bends 12 of the device frame 11 can alter the properties of the frame 11 and result in improved sealing characteristics or the ability of the device 10 to impinge upon the vessel wall 70 to prevent migration or shifting. In the illustrative embodiments, the coil turn 14 is formed as previously disclosed whereby each bend 12 is in a untensioned state with the adjacent sides 13 having an initial angle after formation of the bend 12. For example, in the embodiment of FIG. 20, the initial angle 109 after the bends are formed and the final angle 110 after the frame 11 is assembled are both approximately 90°. Therefore, the bends 12 of the embodiment of FIG. 20 are not placed under any significant degree of tension. In the embodiments of FIGS. 21-31, the frame is restrained to permanently place the bends 12 under tension such that the angle between the sides 122,123 adjacent to the bend 12 is increased or decreased by some method of manipulation to produce a resiliently tensioned bend 118 (FIGS. 26 and 29) having a final angle 110 different than the initial angle 109 (e.g., FIG. 28).

Referring particularly to FIGS. 21-28, the covering 45 (including a full or a partial covering 58) can be attached to the frame 11 of the valve 43 or other embodiment of the present invention, to constrain a generally untensioned square frame 11 (such as in FIG. 1) and subsequently form an altered shape 82, such as a diamond 153, in which the distance between bends 20 and 21 is lengthened and the distance between bends 22 and 23 is shortened. By way of example, and using FIG. 21 as reference, the angle 110 measured between the adjacent sides 13 from bends 20 and 21 might decrease to 70-80° with a increase in the corresponding angles 161 measured at bends 22 and 23 to 100-110°. This manipulation of the frame 11 shape serves to add tension in each of the bends, which allows better positioning of the device 10 against the vessel wall 70 while in the deployed configuration, as shown in FIGS. 22-25. Additionally, constraining the frame 11 along the first axis 94 of the slit 108 allows that distance 146 to be adjusted to provide the optimum size for the vessel 33 into which the valve 43 is to be implanted. Assuming a resilient frame 11 is being used that makes the valve 43 radially expandable, it would normally be preferential to slightly oversize the valve 43 along at the width 146 of the frame 11 (along first axis 94) when the valve 43 is in the generally flattened configuration 35, thereby causing the leaflets 78,79 to relax slightly when the valve 43 is in the deployed configuration 36 and being constrained slightly by the vessel 33. The proper length of the constrained frame 11 as measured diagonally between bends 22 and 23 is calculated such that the leaflets 78,79 open by an effective amount in the presence of blood flow 46 that most closely mimics that found in a normal functioning valve.

Dog studies by Karino and Motomiya (*Thrombosis Research* 36: 245-257) have demonstrated that there is about a 60 to 70% constriction of blood flow through the natural valve. In the valve 43 of the present invention, the leaflets 25 should ideally span about 30-60% of the vessel 33 diameter across. If it is much less than 30%, blood flow 46 may be impeded to an unacceptable degree, while if the leaflets 78,79 are allowed to fully open, they can adhere to the vessel wall 70 and therefore, not close properly in the presence of retrograde flow 47. The frame 11 can be formed or constrained such that the distance 146 between points 22,23 lies between $\pi r$, which would allow the valve to open to the full extent that the vessel allows, and $2r$ in which the valve 43 is stretched tight across the frame 11 and is very limited in the amount of blood that will allow to pass through. To give the leaflets the flexibility and compliance to open to permit flow and then close to seal against backflow, the slit axis distance 146 of the valve 43 should be oversized with respect to the diameter of the vessel into which it is to be placed. Constraining the valve 43 along the first axis 94 such that it sized a few mm larger than the lower extreme ($2r$) or a few mm larger than the upper extreme ($\pi r$), not only allows the leaflets to function in a more optimal manner, but also allows the valve 43 to safely and effectively impinge on the vessel wall to seal and reduce the possibility of migration. The ideal amount of oversize is largely dependent on the size and diameter of the frame 11 prior to resizing. FIG. 50 depicts a schematic top view of the valve of FIG. 22 showing the length 147 of the orifice, the width 148 of the orifice, the portion 154 of the vessel occluded by a leaflet 25, and the corner gaps 155 than exist between each lateral edge 156 of the valve orifice 117 and the outer edge 112 of the leaflet 25 (or the frame 11). The following formula can be to approximate the elliptic circumference (C) of the valve orifice 117, where a=one half the length 147 of the orifice, and b=one half the width 148 of the orifice 117:

Assuming that we wish to size the valve 43 to produce an orifice 117 that opens approximately 30-60% of the vessel lumen 34 (with the occluded portions 154 comprising 40-70% of the same), the preceding formula can be used to determine the amount of oversize that produces the desired characteristics. The amount of oversize (valve width 146 in the flat configuration minus the diameter of the vessel lumen 34) would generally range from 1-2 mm for smaller valves (those placed in 8-9 mm vessels) up to 3-4 mm for valves intended for larger vessels (17-21 mm). For example, a valve intended for a 14 mm vessel should ideally have a 2-3 mm oversize if the range of 30-60% opening is to be maintained. If the frame 11 of a valve 43 having 20 mm sides is constrained such that the distance between bends 22 and 23 is adjusted to approximately 16 mm, the valve 43 opens approximately 43%, which is well within the most desired range. If constrained to 17 mm, the valve 43 is able to open up to approximately 55% of the vessel diameter. In contrast, oversizing the valve 43 by 6 mm, produces a large orifice 117 of 83% which lies outside the target range, although it would certainly produce a valve 43 capable of opening and closing in response to fluid flow 46,47. To produce a valve 43 in which the valve width in the generally flattened configuration 35 is 17-18 mm, which would be a valve 43 sized to accommodate a 14-15 mm vessel, the 20 mm frame 11 should be constrained such that the distance between bends 22 and 23 is 15 mm prior to addition of the covering 45, if a compliant material such as SIS is used. As depicted in FIG. 26, the frame 11 is constrained across the first axis 94 using a temporary constraining mechanism 121, such as by tying a suture through the coil turns 14 of bends 22 and 23 to pull them toward one another until a distance of 15 mm is reached. After the covering 45 has been attached, such as by the method previously disclosed, the temporary constraining suture 121 is cut, which results in a slight expansion in the width of the frame 11 as the SIS stretches under the tension of the constrained frame, resulting in the desired final width of 17-18 mm. The amount of expansion varies with the compliance of the particular covering 45 as well as the resiliency of the frame 11. Although the desired final width 146 of the constrained frame 11 can result from a relatively wide range of initial frame 11 sizes, depending on how much the frame is constrained, generally, larger sized frames (e.g., sides measuring about 25 mm) are most suitable for larger vessels (e.g., 16-21 mm in diameter), while smaller frames (e.g., 15 mm) are most suitable for smaller diameter vessels (e.g., 8-9 mm). While this range represents the most common sizes used for correcting venous valve insufficiency in the lower legs, valves 43 of the present invention can be made in a much larger range of sizes to treat veins or other vessels elsewhere in the body.

Figure 28:
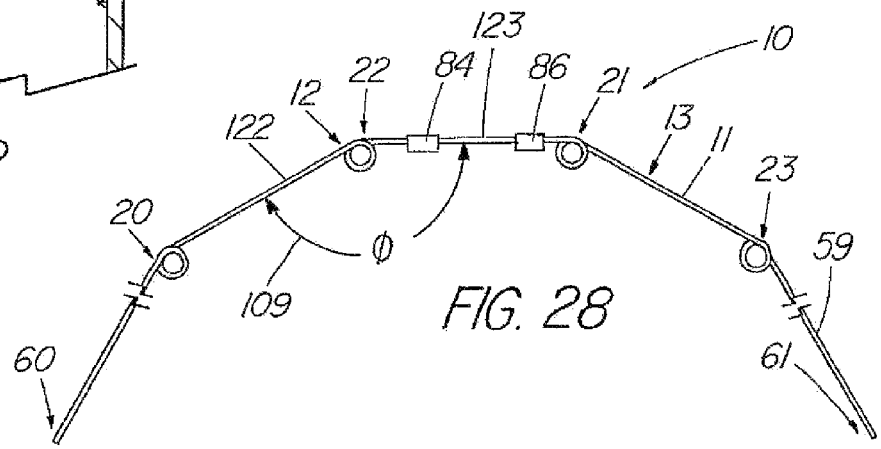
FIG. 28 depicts a top view of an embodiment of the present invention, made using the method shown in FIG. 28.
Figure 31:
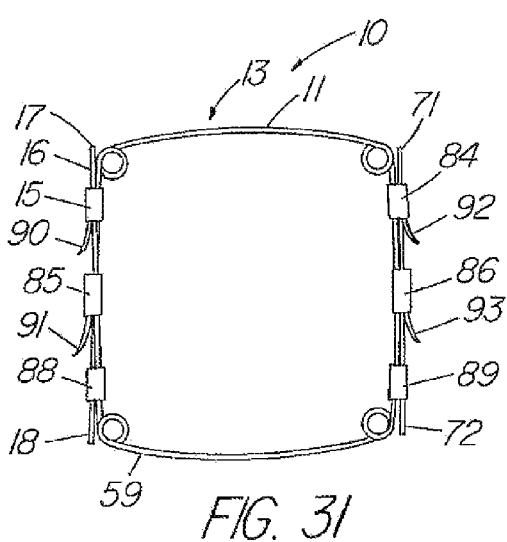
FIG. 31 depicts a top view of an embodiment of the present invention, made using the method shown in FIG. 28.
Figure 32:
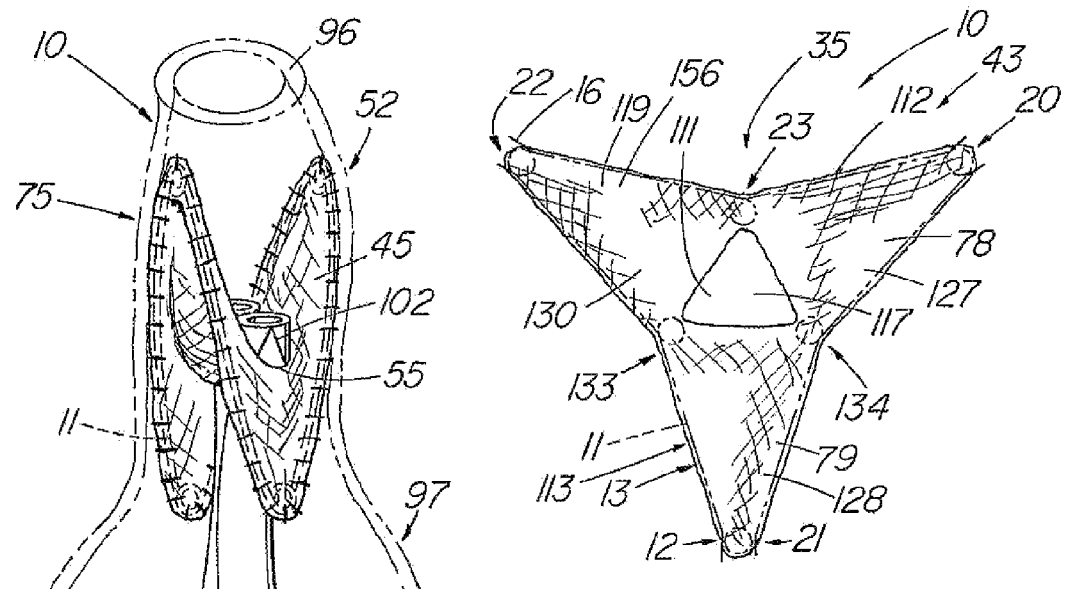
FIG. 32 depicts a pictorial view of an embodiment of a stent graft that includes stent adaptors of the present invention.

FIGS. 28-31 depict another embodiment of the present invention in which a open frame 11, such as depicted in FIG. 28, is assembled into a square frame (FIGS. 29-31) such the bends 12 are put under tension. The resiliently tensioned bends 118 in the assembled device (as shown in FIGS. 29-31) result from the initial angle 109 formed in wire frame 11 before being assembled into a closed circumference 62 (FIG. 28), being greater than the final angle 110. To form the embodiment of FIG. 1, for example, the wire is wrapped around a pin to form the coil turns 14 with the sides 13 generally lying about 90° with respect to one another. The attachment mechanism 15 then secures and closes the frame 11 to form the final square shape. In the embodiments of FIGS. 28-31, the first angle 109 is made approximately 150°, rather than 90°, which is the desired final angle 110. While the wire is not under stress after the bends 12 are initially formed, the bends 12 and sides 13 are stressed when the device 10 is constrained during assembly to form the four-sided, generally square shape. In particular reference to FIG. 30, the sides 122,123 adjacent to a resiliently tensioned bend 118 becomes somewhat deformed when the bend 12 is put under stress, generally assuming a bowed shape between the adjacent bends. By creating this 'rounded square' with tensioned or stressed bends 118, the sides 13 of the frame 11 are able to better conform to the rounded vessel wall 70 than would a side 13 that is initially straight prior to deployment. Additionally, by rounding the distal bends 116 of the valve legs 113, it may also reduce the potential for the valve legs 113 to cause trauma to the vessel 33 as they continue to exert force thereupon.

An additional method of constraining the valve 43, or similar type device 10 (e.g., occluder, filter, stent, stent adaptor), is depicted in FIG. 48 in which a circumferentially constraining mechanism (or circumferential member), 125, is added to at least partially encircle the frame 11 while it is in both the delivery configuration 37 (FIG. 6) and the deployed configuration 36 such that the device 10 is limited in its ability to radially expand. Once the device reaches its maximal radial expansion, the outward force the device 10 places on the vessel wall 70 is eliminated, thereby reducing potential damage thereto (e.g., from an improperly sized valve), such as tissue erosion possibly resulting in eventual perforation of the vessel 33. In the illustrative embodiment, the circumferentially constraining mechanism 125 comprises a suture that is affixed to and completely encircles the frame 11 to limit the outward expansion of the valve legs 127,128. The sides 13 of the valve legs 127,128 include an intermediate coil turn 126, also illustrated in FIG. 39 fulfilling a different function, that provides an effective attachment point through which to feed and/or affix the suture restraint 125. In the illustrative embodiment, the suture restraint 125 is in a relaxed state when the device 10 is loaded in the delivery system. Then, as the device 10 is deployed, it expands within the vessel 33 until it is constrained by the suture restraint 125 if the device 10 has been properly sized such that vessel 33 does not provide constraining forces sufficient to prevent the device 10 from fully expanding to its predetermined maximum diameter. If the device is undersized for the diameter of the vessel, it may be subject to migration due to insufficient expansion. The illustrative embodiment is merely exemplary of the numerous available circumferentially constraining mechanisms 125. It is not necessary that the circumferentially constraining mechanism 125 completely encircle the device 10. For example, short pieces of suture or another type of tethering mechanism, such as a section of webbing or other material, can be affixed between the sides of the valve legs to limit their expansion, or the frame can include an integral circumferentially constraining mechanism 125, such as an expandable strut formed as part of the frame, line 125 of the illustrative embodiment being also representative of a expanded strut attached to the sides of the frame. The strut would unfold as the frame radially expands and limits how far the sides of the valve leg to which is attached, can spread apart relative to each other, thereby limiting the outward radial force from the device against the vessel wall.

Another possibility is for circumferentially constraining mechanism 125 to comprise a sleeve 162 of flexible material, such as SIS around the valve 43, as depicted in FIG. 49, which is of a diameter appropriate for deployment within the target vessel 33 (typically, being slightly larger than the target vessel diameter) that allows the valve to anchor thereto. The sleeve 162 could be affixed to the frame 11 with sutures 50 or by some other means as the valve 43 is held in a collapsed condition prior to loading the device 10, including the sleeve 162, into a delivery system. The sleeve 162 enclosed the length of the valve 43, or the bends 12 and barbs 16 can be left uncovered, as shown. To reduce resiliency of the sleeve 162, tethers and other types of circumferentially constraining mechanism 125 can be used in combination with the sleeve 162 to limit radial expandability of the valve 43. It should be noted that if the circumferentially constraining mechanism 125 itself is a resilient member, it will only serve to reduce the outward force of the device 10 against the vessel wall 70 until maximum expansion is reached.

FIGS. 30-31 depict alternative methods of forming the frame 11 and attaching barbs thereto. In the embodiment shown in FIG. 30, attachment mechanisms 15,85 and 84,86, per side rather than a single cannula as shown in previous embodiments, such as FIG. 29. Rather than placing the attachment mechanisms 15 at the point 87 where the respective ends 60,61 of the wire frame 11 cross to form the square shape, two attachment mechanisms 15,85 are placed on either side of the cross point 87. Having an additional attachment mechanism 84,85,86 on a side 13 provides better fixation of the frame with little additional metal and helps prevent twisting of the frame 11. On the opposite side which contains the double ended barb 39, the double attachment mechanisms

84,86 arrangement provides a similar function. In the embodiment of FIG. 31, three attachment mechanisms 15,85, 88 and 84,86,89, are used per side which provide better fixation of the frame 11 as well as serving as attachment points for including supplemental barbs 90,91,92,93 to provide a more secure anchoring of the device 10 to the vessel wall 70. The illustrative barbs 16 are typically configured such that they extend only a short distance (less than 1-2 mm) beyond the bends 12; however, the barbs 16 can be made virtually any practical length, such as extending them more than 1 cm beyond the bends 12 to aid in stabilizing the device 10 upon deployment such that it does not shift laterally and end up being cockeyed within the vessel. To assist in this function, the barbs can be shaped accordingly, rather than be limited to a substantially straight configuration.

Figure 35:
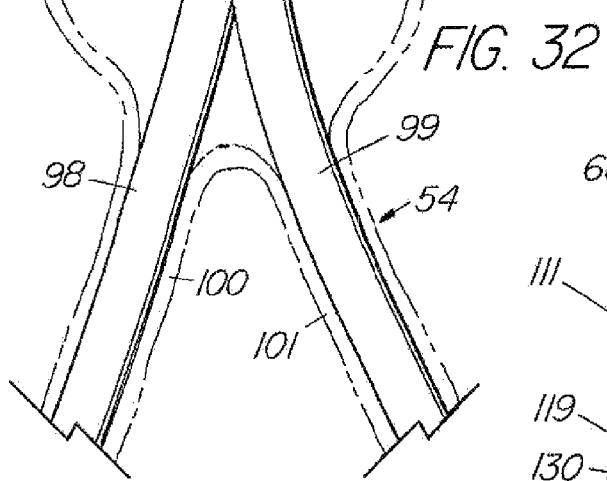
FIG. 35 depicts a top view of a three-leg valve embodiment of the present invention, before and after being constrained.

The present invention is not limited to a two-leaflet valve 43 (or two-leg occluder or stent adaptor, etc.). FIGS. 35-40 depict multi-leaflet valves 43 having three or four valve legs 113 and leaflets 25. The addition of additional leaflets reduces the load produced by the fluid column upon each individual leaflet 25. This in turn, puts less stress upon the sutures or attachment points of the covering 45, thereby allowing the valve 43 to function under higher pressures than would otherwise be possible. For example, these valves 43 could prove advantageous for use on the arterial side, such as to augment pulmonary valves, or within the heart itself, where pressures exerted on the leaflets can be significantly higher than normally found on the venous side. FIG. 35 depicts a valve 43 which in the generally flattened configuration 35, has a three legs 127,128,130 that lie approximately 120° with respect to one another. The respective leaflets are arranged such that the inner edges 111 thereof, define a triangular-shaped valve orifice 117. When the illustrative valve 43 is placed in the vessel 33 for which it has been properly sized, as depicted in FIG. 37, the leaflets 78,79,119 are able to close against one another to seal the valve. The concept of adding additional legs 113 to distribute the load over a larger number of attachment points 50 (e.g., sutures) and add positional stability to the device 10, can be applied to occluders and stent adaptors as well.

Figure 36:
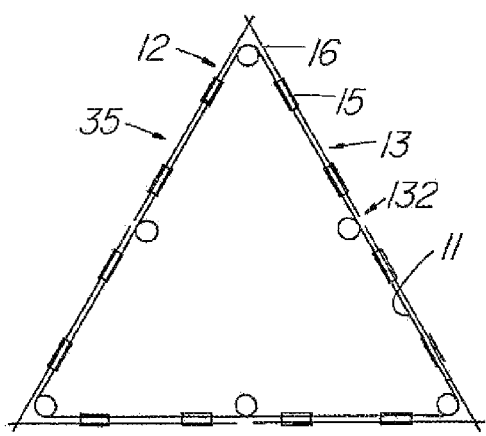
FIG. 36 depicts a top view of a three-leg valve embodiment of the present invention, before and after being constrained.
Figure 37:
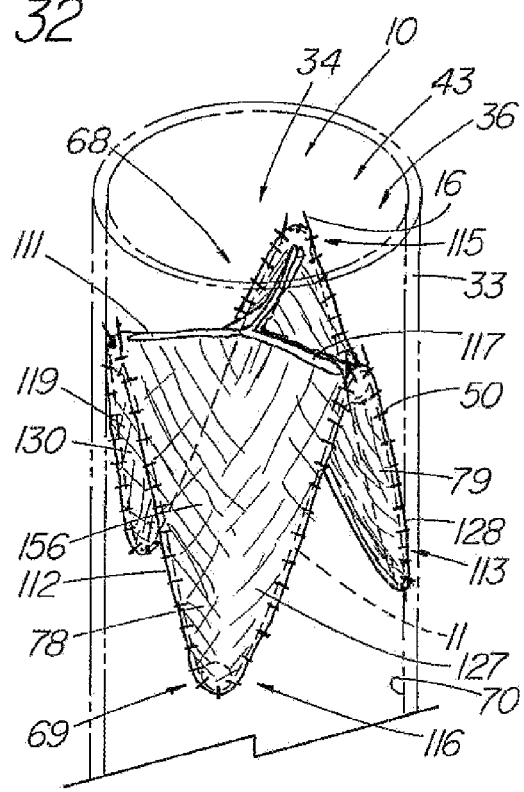
FIG. 37 depicts a pictorial view of the embodiment of FIG. 35 in the deployed configuration.
Figure 38:
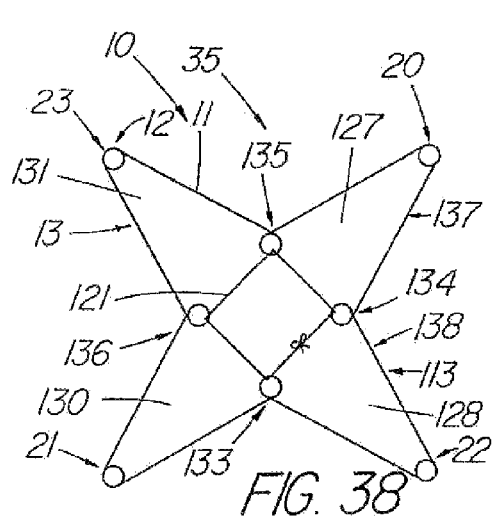
FIG. 38 depicts a top view of a four-leg valve embodiment of the present invention, before and after being constrained.

One method of forming the embodiment of FIG. 35, involves constructing a triangular-shaped frame 11, as shown in FIG. 36, that includes an intermediate coiled eyelet 132 formed at the midpoint of each of the three sides 13. A temporary constraining suture 121, such as that shown in FIG. 38, is threaded through each of the intermediate eyelets 132, drawing them inward to form three additional bends 133,134, 135 forming three legs 127,128,130 of a desired shape (FIG. 35), depending how tightly the constraining suture 121 is drawn. At this point, the covering 45 is attached to the frame 11, either as three separate leaflets 78,79,119, or a single piece through which the triangular-shaped valve orifice 117 is formed. After the covering 45 has been secured to the frame 11, the constraining suture 121 is cut and removed. As depicted, the barbs 16 are affixed to the triangular shaped frame of FIG. 36, two per side, such that they terminate on either side of intermediate eyelet 132. Thus, when the intermediate eyelets 132 are drawn inward to create six sides 13, each includes a barb 16.

Figure 39:
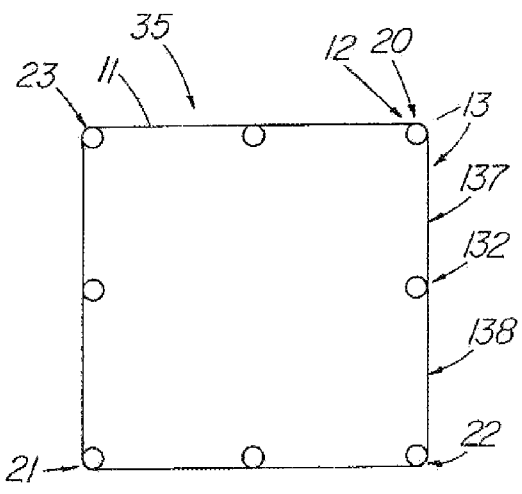
FIG. 39 depicts a top view of a four-leg valve embodiment of the present invention, before and after being constrained.
Figure 40:
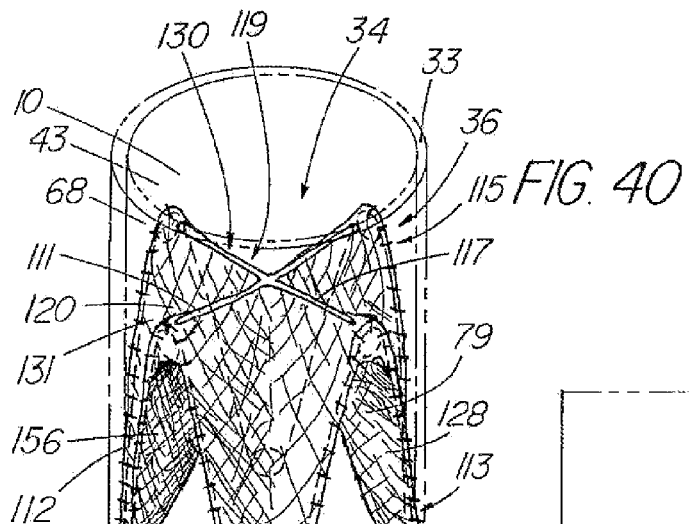
FIG. 40 depicts a pictorial view of the embodiment of FIG. 38 in the deployed configuration.

The embodiment of FIGS. 38-40, which includes four legs 127,128,130,131, is formed in a similar manner to that of the embodiment of FIGS. 35-37. The frame 11 is initially formed in a square configuration (FIG. 39) with intermediately placed coiled eyelets 132 at the midpoint of each side 13, dividing the side into a first and second side portion 137,138. As depicted in FIG. 38, the temporary constraining suture 121 is used to draw the eyelets inward where they form the four additional bends 133,134,135,136 such that four valve legs 127,128,130,131 are formed with the first and second sides portions 137,138 becoming sides 13 of adjacent valve legs 127,128. A square-shaped valve orifice 117 is created when the four leaflets 78,79,119,120 are attached to the legs 127, 128,130,131 of frame 11. One should appreciate that valves with more than four legs would be made in a similar manner to the embodiments above with a five-sided valve being formed from a pentagon, a six-sided valve being formed from a hexagon, etc.

Figure 33:
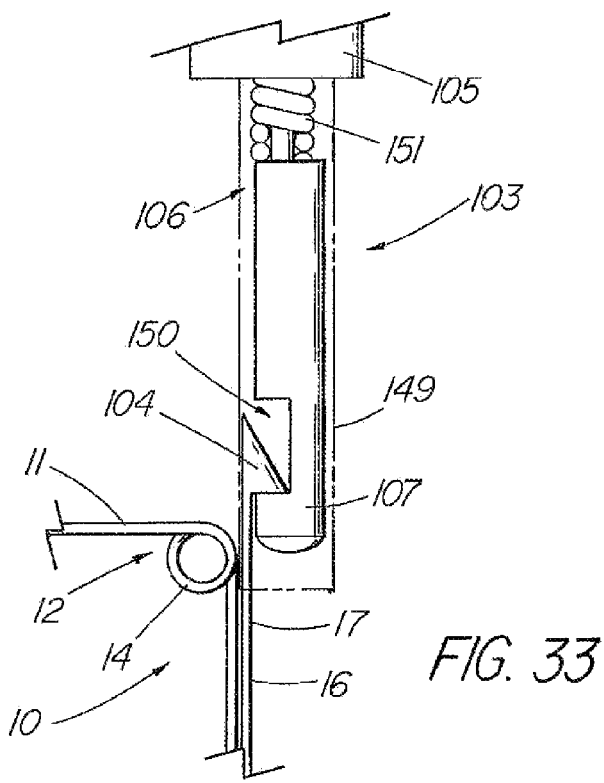
FIG. 33 depicts a delivery system for deploying an embodiment of the present invention.

Delivery of the device 10 of the present invention can be accomplished in a variety of ways. One method, depicted in FIG. 33, involves the use of a delivery system 103 similar to that used to deliver embolization coils. The delivery system 103 comprises an outer member 105, such as a cannula or catheter, and an coaxial inner member 105 that includes a tethering tip 107, such as a notched cannula, adapted to receive a barb 17 extending from the frame 11. The tip 104 of the barb is configured such that it can positively engage with the tethering tip 107. This can be accomplished by adding a projection, such as a secondary barb, hook, spine, etc. to the tip 104, or otherwise enlarging the diameter thereof such that it can be releasably secured by the tethering tip 107 until deployment. The coaxial inner member 106 also includes an outer sheath 149 that retains and the locks the barb tip 104 within the tethering tip 107 until it is advanced or retracted by manipulation of a proximal handle (not shown) to expose the notch 150 in the tethering tip, which releases the barb 17 and deploys the device 10. The device 10 is preloaded within the outer member 105. The coaxial inner member 106 and attached device 10 are then advanced together from the outer member 106 at the target site. Further manipulation of the proximal handle, advances the tethering tip 107, which in this particular embodiment, includes a coiled spring 151, relative to the outer sheath 149. After the device 10 has been released from the tethering tip 107, the spring-activated handle is released and the outer sheath 149 slides back over the tethering tip 107. The coaxial inner member 106 is withdrawn into the outer member 105 and the entire delivery system 103 is removed from the patient. As shown in FIG. 33, the barb tip 104 extends just beyond the coil turn 14 of the frame 11 so as to have sufficient room to engage with the coaxial inner member 106. The barb tip 104 must be positioned to account for whether the device 10 is to be placed using a femoral approach or a superior approach.

The illustrative delivery system 103 represents only one of many possibilities. For example, the device 10 can be attached to a delivery device using screws, clips, magnets, or some other tethering mechanism, or can be deployed by applying electrical current, heat, or some other means to cause detachment with a carrying mechanism. As previously disclosed, rather than making the device 10 self-expanding, where it is pushed from some sort tubular device, it can be formed from a ductile material, mounted over a balloon or other inflatable or expandable delivery mechanism, and deployed by expanding the device in that manner.

Figure 52:
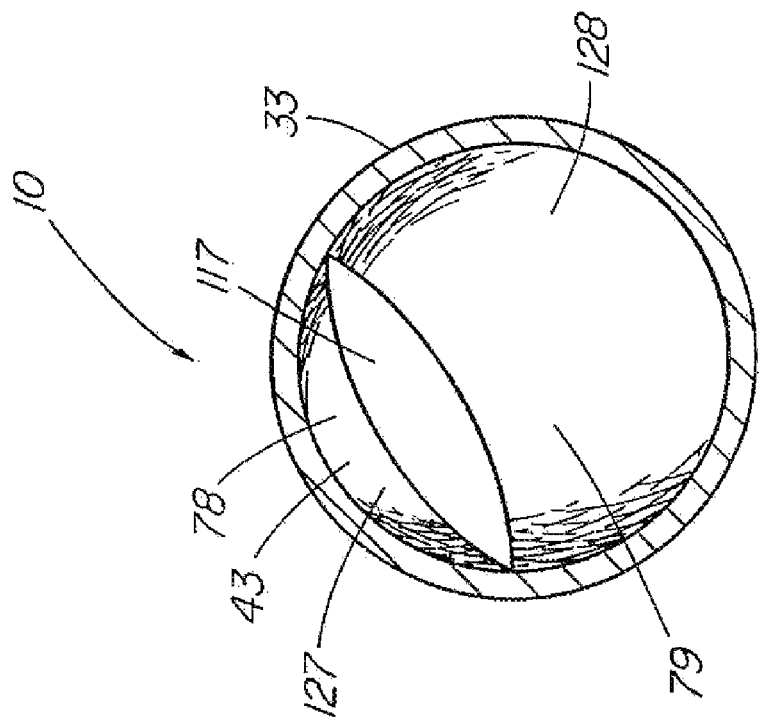
FIG. 52 depicts a top view of the valve in FIG. 51.
Figure 51:
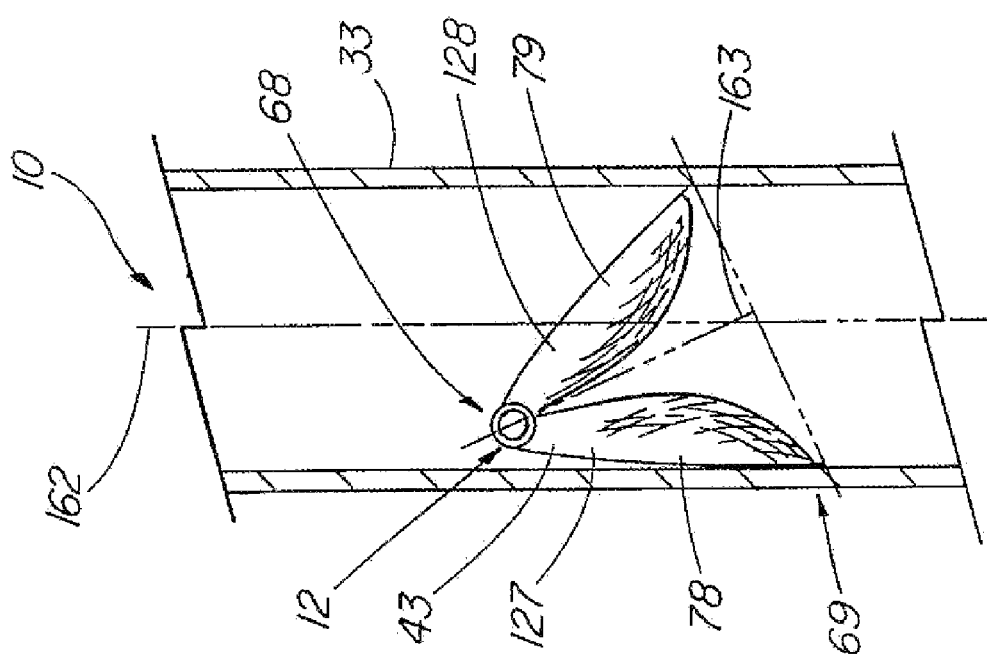
FIG. 51 depicts the embodiment of FIG. 22 having titled following deployment within a vessel.

The illustrative valve embodiments having a simple four-bend serpentine frame, such as the one depicted in FIG. 21, advantageously limit the amount of metal being placed into the vessel. This is thought to help reduce the risk of thrombus formation, as well as allow the device to assume a smaller profile in the delivery system. Because this configuration lacks some of the longitudinal stability of a frame having additional points of contact with the vessel wall (e.g., at least 4-6 at each end), there is a greater risk of the valve being deployed off-center, such as depicted in FIGS. 51 and 52, wherein the longitudinal axis of the valve does not coincide with the longitudinal axis of the vessel. Titling is often the result of particular bend exerts more force than others, causing the bends to become pivot points that cause longitudinal shifting of the valve prosthesis. This, of course, results in the opening 117 of the valve being located off-center with respect to the vessel 33, which may result in the function of the leaflets 78,79 being impaired such that the valve will not properly open and close in response to blood flow and/or blood may pool excessively (not clear itself) in certain locations along the base of the leaflets, leading to thrombus formation. When the leaflets comprise remodelable biomaterials, such as SIS and other ECM materials, off-center deployment can result in one or more leaflets broadly contacting the vessel wall, which could result in tissue ingrowth affecting the ability of the leaflet(s) to function and coapt with other leaflets. Thus, a centered orifice (e.g., the point along which the leaflets coapt or otherwise contact or seal against one another) is generally considered the optimum configuration in a multi-leaflet valve. Even six bend stent designs (three bends oriented at each end) have been shown to be longitudinally unstable. Generally, longitudinally stability becomes less of an issue once there are four bends or more oriented at a particular end of the stent frame so that tilting is less likely to occur, although it is not necessarily desirable to have a four legged valve to address the tilting problem.

One method of addressing the problem is in the design of the delivery system, while another involves modification of the valve that have additional structure attached to the legs of the valve to FIGS. 53-71 depict various embodiments of the present invention in which the valve 43 includes a centering support element 164 configured to contact the vessel wall in a manner to support and help properly align with the vessel, the basic valve portion 43 which in these particular embodiments, comprises a generally saddle-shaped, serpentine configuration that includes a pair of co-aptable leaflets 78,79 that define an opening between two bends 20,21 comprising the first end 68 of the valve 43, the outer edges 112 of the leaflets comprising a frame 11 or resilient portion that allows the valve portion to form a seal around the entire circumference of the vessel, such that the leaflet material, preferably an ECM such as SIS, is in direct contact with the vessel wall. The centering support structure 164 is defined as a single element or plurality of elements attached to, or integral with, the valve portion 43 and which include one or more contact points 167 that engage the vessel walls such that upon deployment, the valve portion 43 is largely prevented from tilting relative to the longitudinal axis 162 of the vessel, as depicted in FIGS. 50-51, so that the opening 117 of the valve is generally centered thereinside.

The centering support structure 164 of the present invention falls into two general categories. Devices 10 of the first group include support structure 164, such as second and/or third frames 31,32, an adjoining stent 219 or other expandable or inflatable elements, that are connected to, or integral with, the basic valve portion 43, and that are either attached to the proximal end, distal end, or both ends thereof. Such supporting structure 164 functions by either expanding or deploying within the vessel in advance of the valve portion such that the valve portion is less likely to tilt off-center when it fully expands, or by trailing or following the valve portion 43 out of the delivery system so that as the valve portion deploys, the centering support structure 164 remains within or attached to the delivery system to help longitudinally align the valve portion within the vessel until the support structure 164 deploys as well, as well as to prevent the valve from 'jumping' from the delivery system.

An example of a device 10 having the first type of centering support structure 164 is depicted in FIG. 53, in which the centering support is provided by a second frame 31, of the same type of the valve portion 43, attached to the valve portion by an attachment mechanism 171 such as sutures, where points 169 and 170 of the second frame 31 to bends 22 and 23, respectively. When the device 10 is deployed from the delivery system such that the second frame 31 is allowed to expand within vessel 33, the two arms 165,166 comprising the second frame expands to contact the vessel walls 70 at points 167 and 168 located at the proximal ends of respective arms 165,166 and the first or proximal end 68 of the device 10, the lateral arms basically providing a structure mirror of the two legs 127,128 of the valve. In the illustrative embodiment, the centering support structure 164 includes a pair of barbs 172 extending from each of the arms 165,166 to further secure the device and prevent migration.

Following deployment of the leading second frame 31, the valve portion 43 is still within or secured by the delivery system, helping to maintain the second frame 31 in a longitudinally stable position. When the valve portion is deployed 43, the second frame 31, already secured in the vessel 33, provides an anchor to prevent the valve portion 43 from tilting off center as the latter expands and lodges within the vessel.

Figure 55:
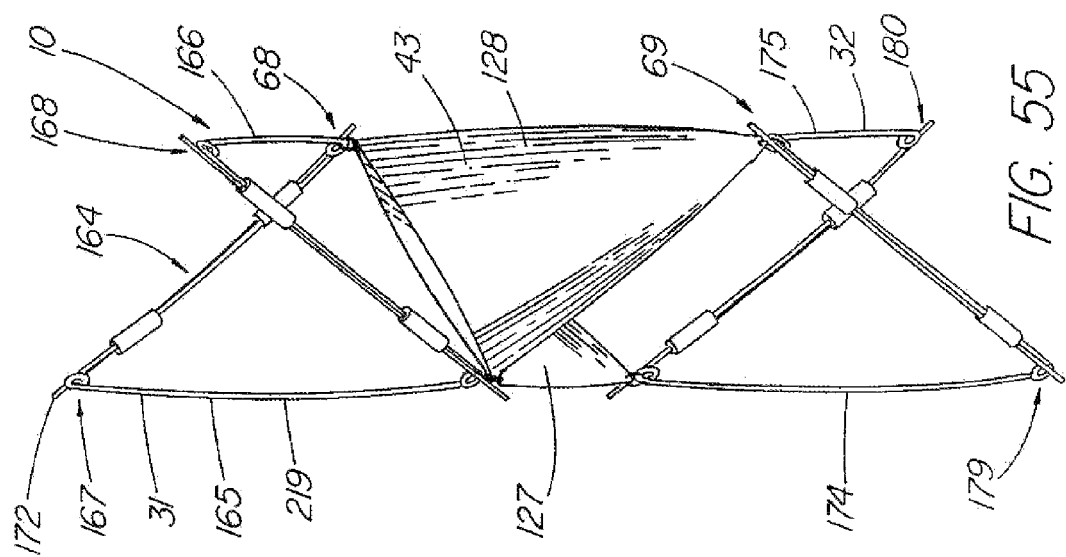
FIG. 55 depicts a pictorial view of an embodiment of the present invention that includes centering support structure comprising one or more adjoining frames or stents.

FIG. 54 depicts an embodiment in which the valve portion 43 and second frame 31 are reversed with points 170 and 171 of the second frame being attached to bends 20 and 21, respectively, at the second or distal end of the valve portion. As the valve portion 43 is deployed, the second frame 31 remains within or affixed to the delivery system, thus reducing the likelihood of the valve portion 43 being deployed off-center with respect to the longitudinal axis of the vessel. Once the second frame 31, the remainder of the device 10, is deployed, the valve portion 43 is already positioned in the vessel, being anchored and maintained longitudinally stable by the second frame until it too is deployed, wherein the valve portion 43 in turn, provides anchoring support of the second frame to prevent it from tilting. FIG. 55 depicts an embodiment that includes both a second frame 31 attached to the first end 68 of the valve portion 43 and a third frame 32 attached to the second end 69 thereof. Thus, the device 10 receives the centering and stabilization benefits of both centering support structure 164 components.

Figure 56:
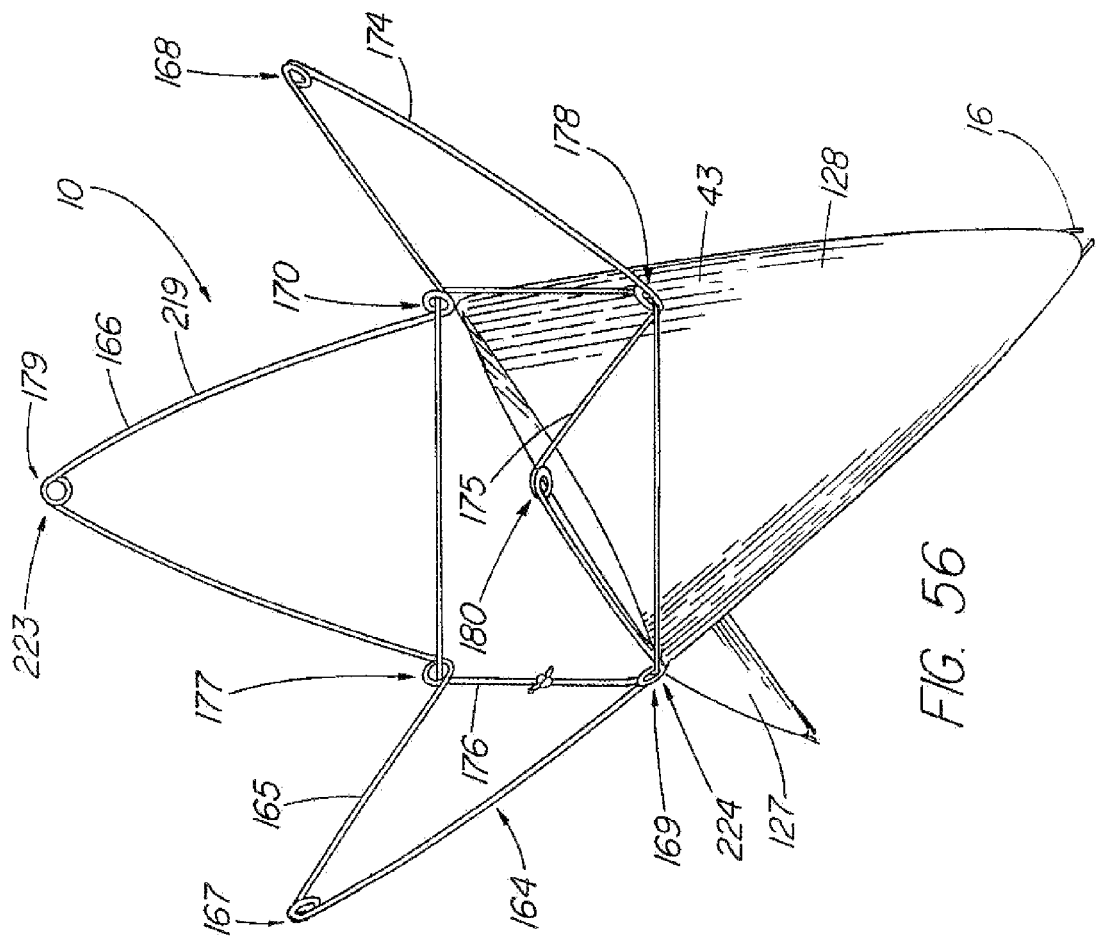
FIG. 56 depicts a pictorial view of an embodiment of the present invention that includes centering support structure comprising one or more adjoining frames or stents.
Figure 57:
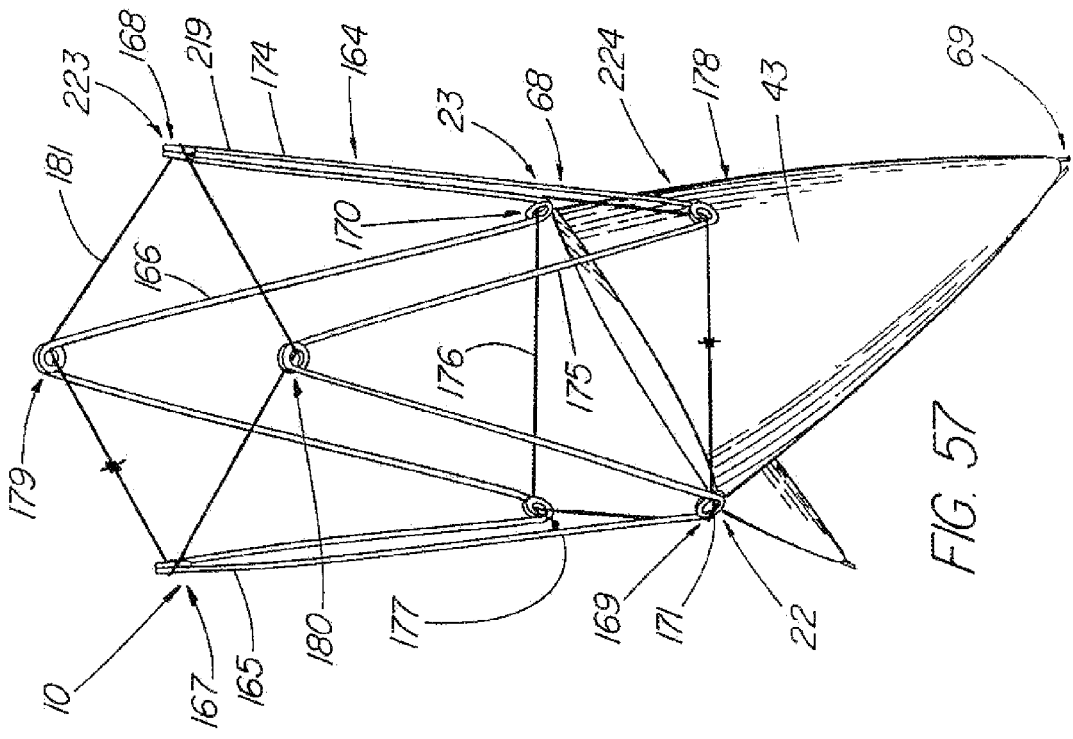
FIG. 57 depicts a pictorial view of an embodiment of the present invention that includes centering support structure comprising one or more adjoining frames or stents.

Besides having the centering support structure 164 comprise second and third frames 31,32 of the same basic four-bend serpentine design, FIGS. 56-57,66-67, and 71-75 depict alternative structure that can be affixed to, or extend from, one or both ends 68,69 of the valve portion 43. FIGS. 56-57 depict an adjoining serpentine or zig-zag stent 219, such as a Gianturco Z-STENT™ (Cook Incorporated) that is attached with suture 171 to the bends 22,23 located at the first end 68 of the stent. As with each of the embodiments, alternative attachment 171 methods can be used, such as ring fasteners, plastic bands, struts, etc. The illustrative adjoining stents 219 include a first radial constraint 176 (which is optional), such as the illustrative suture, at the second end 224 of the adjoining stent 219 to constrain contact points 177 and 178 by threading the suture 176 therethrough, along with the attachment points 169,170 of the adjoining stent 219 which are connected to bends 22 and 23 of the valve portion 43, then drawing the points inward. In the embodiment of FIG. 57, and second radial constraint 181 is included at the first end 223 of the adjoining stent 219 which constrains the four contact points 167,168,179,180 located at that end. The illustrative zig-zag stent 219 includes four points at each end; however, any number of points or configuration that allows attachment to the valve portion 43 may be used.

Figure 83:
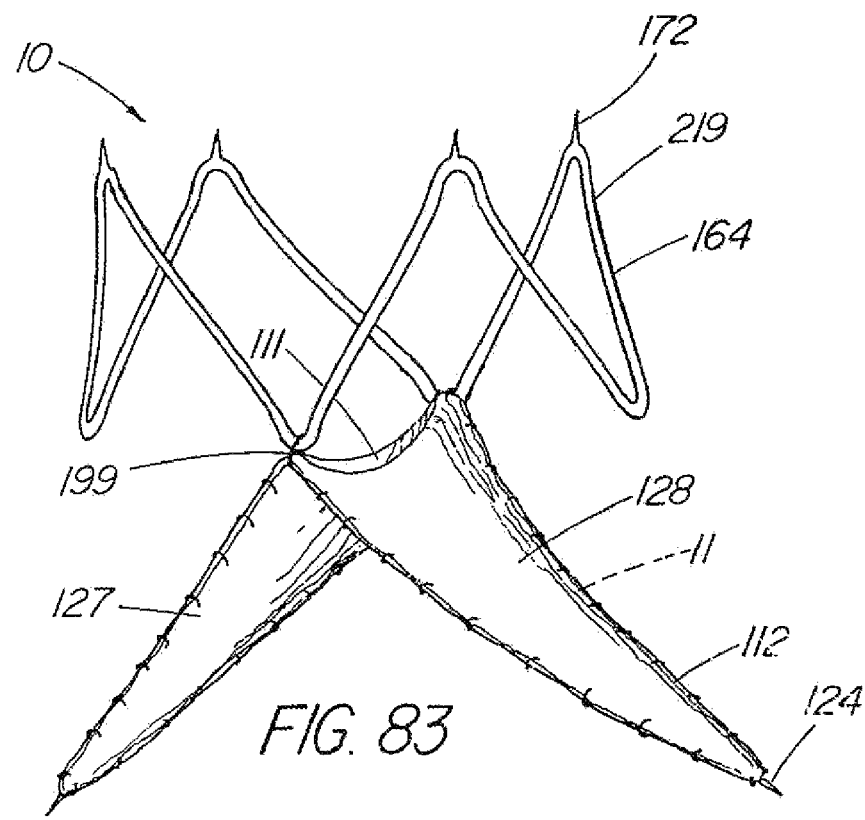
FIG. 83 depicts a side view of an embodiment similar to that of FIG. x formed out of a cannula.

An alternative method of manufacturing the same basic configurations of the embodiments of FIGS. 53-57 is to cut or otherwise form both the valve portion frame 11 and the centering support structure 164 out of a single piece of cannula, such as nitinol, stainless steel, or another suitable stent material. FIG. 83 depicts a cannula-formed embodiment of a valve prosthesis 10 that is similar to the wire-formed version depicted in FIGS. 56-57, which include one or more constraining devices 176,181, not present in the embodiment of FIG. 83, to constrain one or both ends of the adjoining Z-stent portion 219. The illustrative embodiment of FIG. 83 is cut from a nitinol cannula of thickness such that electropolishing result in a strut width of 0.009". The exemplary strut widths for 14.0 mm and 16.5 mm diameter valve prostheses 10 is also about 0.009" width. The valve portion frame 11 and the Z-stent portion 219 are interconnected by a pair of 0.0144" thick struts extending from the opposing proximal/top bends of the valve portion Integral barbs 172 extend from the proximal bends of the centering support structure 164/adjoining frame 210. Integral barbs 124 also extend from the distal/bottom bends of legs 127,128.

Figure 72:
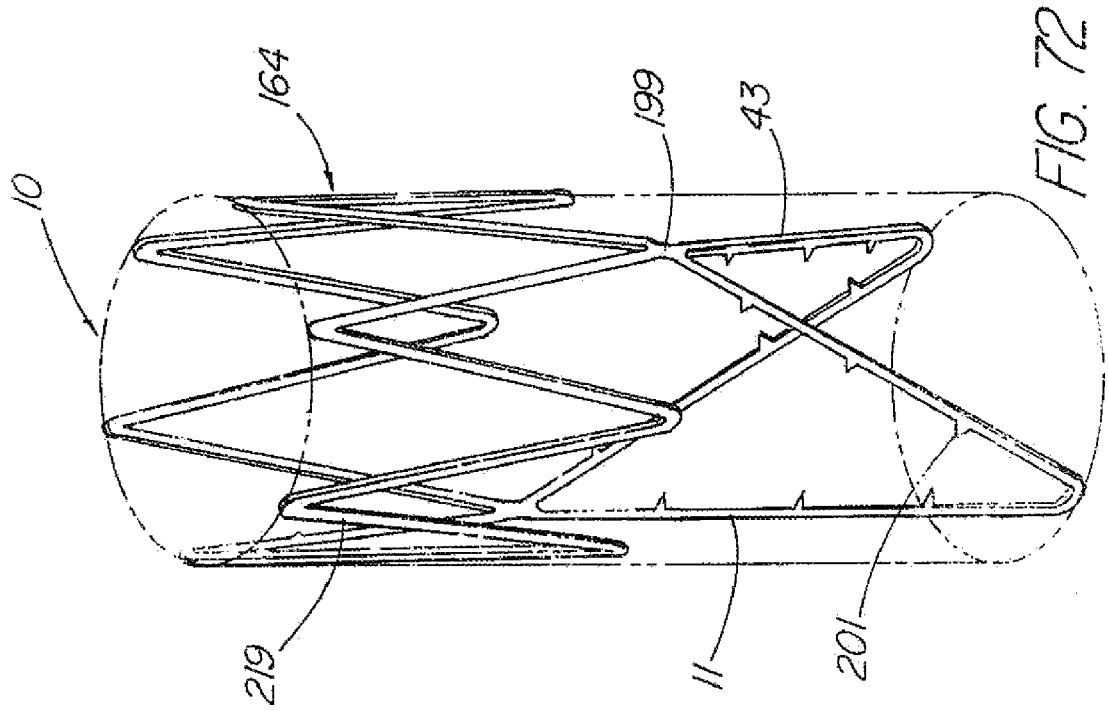
FIG. 72 depicts a pictorial view of an embodiment of the present invention wherein the centering support structure includes an adjoining zig-zag stent.

Another related embodiment is depicted in FIG. 66 in which the adjoining stent 219 comprising the centering support structure 164 is a cannula stent such as the illustrative PALMAZ® Balloon Expandable Stent (Cordis Corp., Miami Lakes, Fla.) that is integrally attached to the first end 68 of the stent portion 43 via a short strut 199. Both the frame 11 of the valve portion 43 and the centering support structure 164 are cut or formed from a single piece of cannula using any well-know method of forming a pattern into a cannula (e.g., laser). FIG. 67 depicts an illustrative embodiment wherein the centering support structure 164 basically mirrors that of the stent portion frame 11, with the attachment 199 therebetween also being a short strut. Integral barb 172 are located on the centering support structure to help anchor the prosthesis in the vessel. FIG. 72 depicts still another embodiment in which the both the stent portion frame 11 and the centering support structure 164 are formed from the same piece of cannula; however, the support structure 164 comprises an adjoining zig-zag stent 219. An optional feature of the embodiment of FIG. 72 are covering attachment tabs or barbs 201 distributed along the frame 11 of the stent portion, which each comprise an integral sharp projection extending from the frame 11 to help secure the covering or leaflets (not depicted) there. These tabs 201 represent an alternative or additional means of fixation to sutures.

Figure 71:
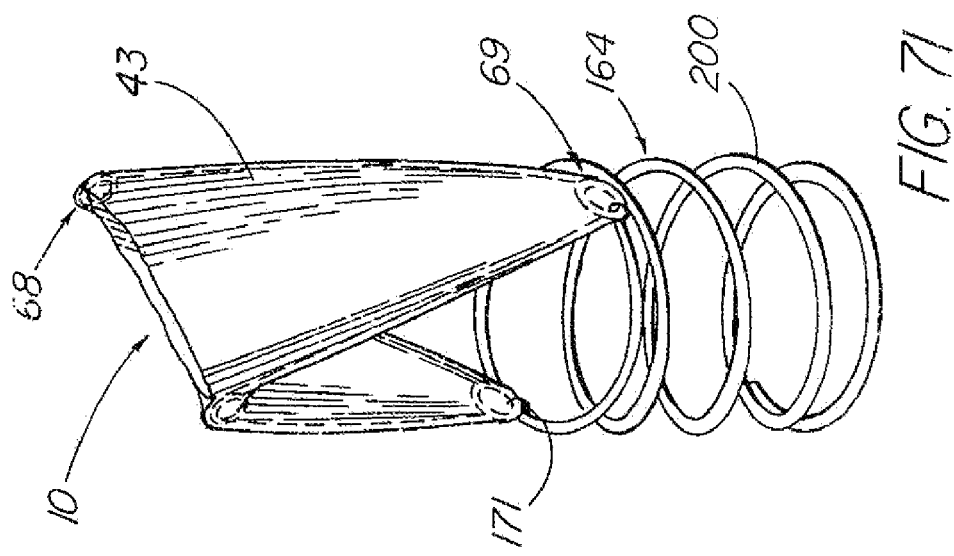
FIG. 71 depicts a pictorial view of an embodiment of the present invention wherein the centering support structure includes a helical configuration.
Figure 74:
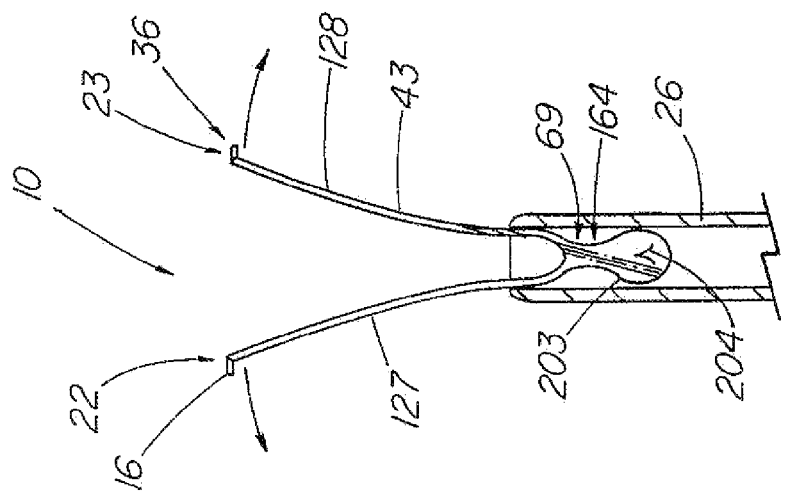
FIG. 74 depicts a side view of an embodiment of the present invention wherein the centering support structure includes a distal projection.
Figure 73:
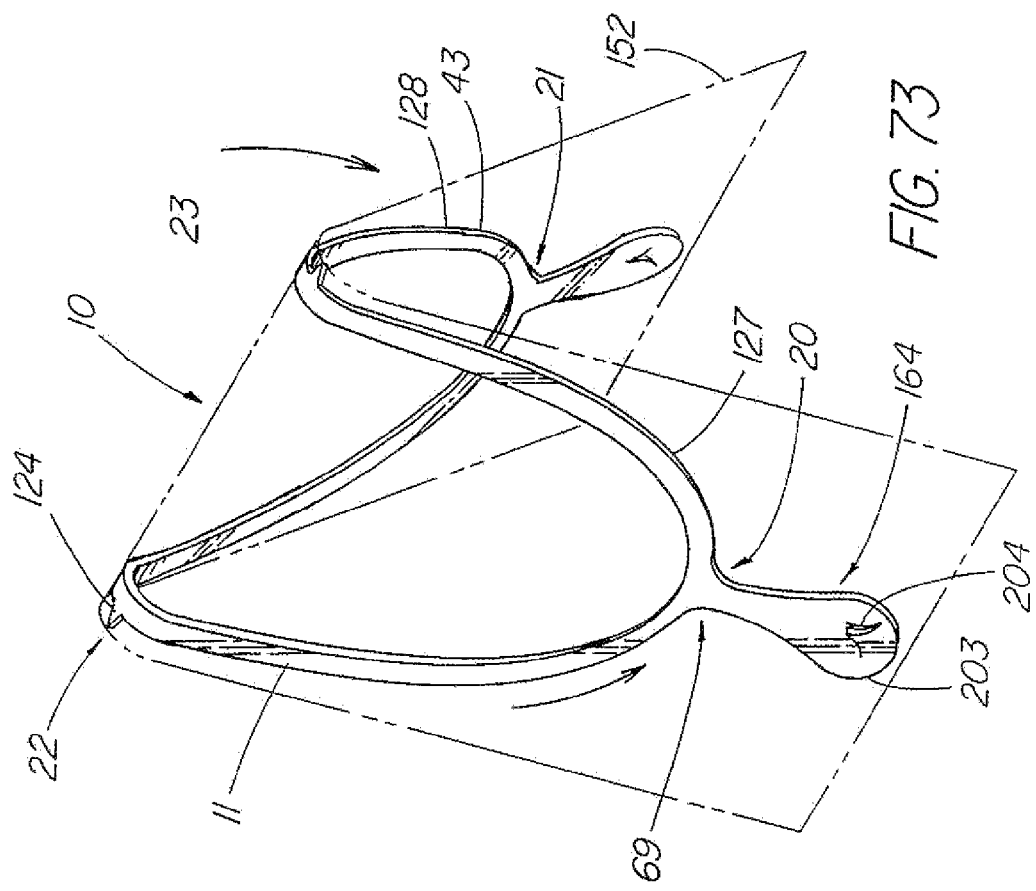
FIG. 73 depicts a pictorial view of an embodiment of the present invention wherein the centering support structure includes a distal projection.

FIG. 71 depicts yet another alternative embodiment of centering support structure 164 comprising an expandable helical structure 200 or spring that extends from the second end 69 of the valve portion 43. The helical structure 200 functions much like the aforementioned second frame or adjoining stent to remain coupled with the delivery system to help center the valve portion 43 within the vessel and/or prevent jumping of the valve. A further example of centering support structure 164 extending from the second end 69 of the valve portion is depicted in FIGS. 73-74 wherein the valve portion 43, which is cut, etched, or otherwise formed from a sheet of metals stock 152 (FIG. 73). When the frame 11 is formed into the second configuration 36, as shown in FIG. 74, the distal projections 203 are brought into close proximity to one another and become the last portion of the device 10 to be deployed from the delivery catheter 26. This allows the valve portion 43 to expand upon deployment, while still tethered to the delivery catheter or sheath 26 (FIG. 74), until the distal projections 203 exits the passageway of the delivery catheter 26, thus helping to maintain the longitudinal alignment of the valve portion 43 as it engages the vessel wall. In the illustrative embodiment, a pair of integral barbs 124 extend from bends 22 and 23 for anchoring the valve portion 43, while the elongate projection 203 also includes an optional barb 204 for both securing the device within the vessel and providing resistance against the inner wall of the delivery system 26 to control the tendency of the device 10 to prematurely deploy when the majority of the valve portion 43 has exited the passageway. It should be noted that where the centering support structure 164 of the exemplary embodiments is shown extending from a particular end or another of the valve portion 43, in most instances, the support structure 164 could be easily adapted to extend from the opposite end as well.

FIG. 75 depicts an embodiment of the present invention that includes both an adjoining stent 219 to provide centering support, such as the illustrative zig-zag stent, as well as an outer proximal sleeve 229 that extends proximally (or upward) from the valve portion 43 and provides the attachment means 199 to the adjoining stent 219, which in the illustrative example is sewn to the first end 231 of the proximal sleeve 229 such that the stent and valve portion frames 11 do not have metal to metal contact. The second end 232 of the sleeve 229 is then attached to the valve potion 43 using sutures 50 or another well-known means. The proximal sleeve 229, which in the illustrative embodiment has the possible advantage of not covering the vessel wall in the region between the two legs 127,128 of the valve portion 43, could optionally comprise a complete cylindrical sleeve, such as the embodiment of FIG. 49. Optionally, the adjoining stent 219, or a second adjoining stent, could be attached to the second end 232 of the sleeve 219 if so configured. The proximal outer sleeve is preferably made of a low or non-thrombogenic biomaterial, such as SIS or another ECM. The number, configuration, and arrangement of anchoring barbs 16 can vary according to use and device configuration. In the illustrative embodiment, a series of barbs 230 are attached to the struts of the adjoining zig-zag stent 219, with the valve portion 43 including another series of barbs 17,18,71,72, as well.

Figure 58:
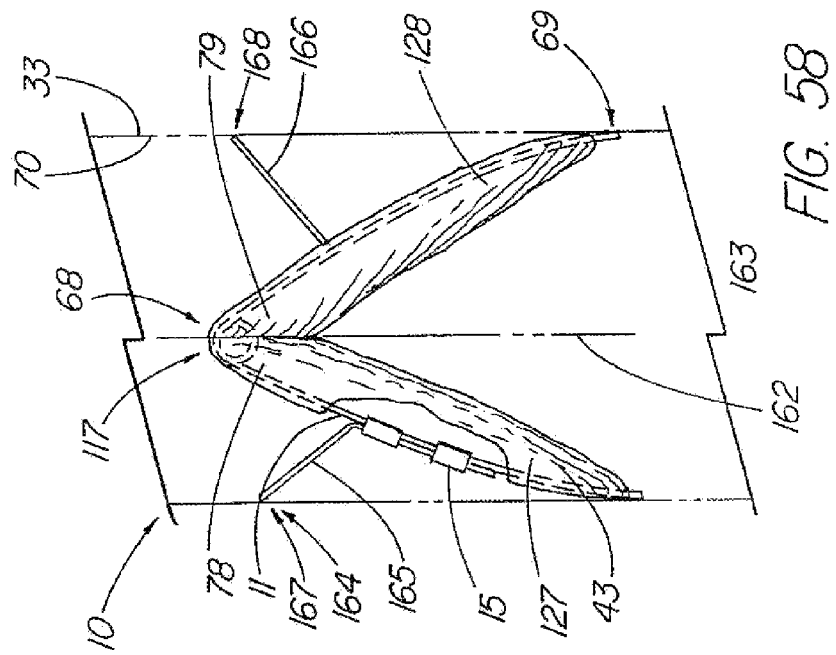
FIG. 58 depicts a side view of an embodiments of the present invention that includes centering support structure comprising a pair of lateral arms.

A second strategy for providing better longitudinal centering support for the valve portion 43 involves the placement of the centering support structure 164, such that it extends laterally from the valve portion frame 11, rather than extending from one or both ends thereof. FIG. 58 depicts a side view of a device 10 that includes a pair of lateral arms or wings 165,166, comprising struts attached to the frame 11 of the valve portion 43. The arms 165,166, typically similar in configuration to the legs 127,128 of the valve 43, extend laterally, following deployment, to provide two supplemental contact points 167,168 that help provide longitudinal support and reduce the likelihood that the valve portion 43 would tilt off center longitudinally during or following deployment. The lateral arms 165,166 advantageously lie between the leaflets 78,79 and the adjacent vessel wall, thereby offering protection from the leaflets possibly adhering to the vessel wall 70, which could lead to failure of the valve leaflets to close or coapt properly during retrograde flow. This problem may be even more likely to occur when the valve is not properly sized (e.g., oversizing) with respect to the vessel. The use of remodelable biomaterials, such as SIS, can further lead to permanent adherence of the leaflets to the vessel wall if the valve is not configured or sized properly for the vessel, thus the lateral elements can be especially advantageous in these particular embodiments.

The basic embodiment of FIG. 58 can be formed in a number of different ways, with selected examples depicted in FIGS. 59-61. The frame 11 of the embodiment of FIG. 59 comprises four components. The lateral arms 165,166 each comprise part of a closed diamond-shape component 182, 183. For example, lateral arm 166 includes four bends 168, 186,187,188, with bend 168 comprising the contact point of the lateral arm 166 and bend 186 forming the bend 20 of the valve leg 128. To permit the arm 166 to extend outward from the valve portion 43 (shown without leaflets) so that it is able to help in centering, bends 187 and 188 deformed in a different plane, such that the closed frame 182 is bent along an axis 189 intersecting both bends. The angle of the bend should be such that the contact point 167,168 exert a safe, but effective pressure against the vessel wall when the valve is in the deployed configuration 36, such that the valve 43 is unlikely to tilt. Each closed section 182,183 is attached to a pair of V-shaped sections 184,185 which each include a bend 22,23 that together, comprise, the first end 68 of the valve portion 43. It should be noted that the term 'V-shaped' also includes the concept of a rounded 'V' or 'U-shaped' section as well. The components 182,183,184,185 can be joined by soldered cannulae, laser or spot welding, or some other well-known means of joining a metal frame. Once assembled into a closed frame 11 having lateral arms 165,166 comprising the centering support structure 164, the ends of the V-shaped sections can serve as anchoring barbs 16 to secure the valve 43 following deployment.

FIG. 60 depicts an alternative assembly of the basic embodiment of FIG. 58. Like the embodiment of FIG. 59, the device 10 includes two V-shaped section 184,185, which in the illustrative embodiment comprise the two legs 127,128 of the valve portion 43. The remaining component comprises a serpentine portion 192 which comprises an eight-bend zig-zag stent in which two of the points 167,168 (those oriented toward the first end 68), and their adjacent struts, form the arms 165,166 comprising the centering support structure 164. The other two points of the serpentine portion 192, adjacent to points 167 and 168, comprise bends 22 and 23 of the valve portion 43, when the components are assembled. The ends of the V-shaped sections 184,185 form barbs 16 at the first end 68 of the device. Optionally, separate barbs can be attached to the frame 11, such as using the illustrative cannulae 15, if barbs are desired at the second end 69.

A third embodiment, similar to those of FIGS. 59 and 60, is depicted in FIG. 61. In this embodiment, the valve portion 43 is basically the same serpentine frame 11 configuration as most of the illustrative valve embodiments (excluding those of FIGS. 59 and 60). The arms 165,166 comprising the centering support structure 164 each include a pair of attachment struts 190,191 that lie parallel to the legs 127,128 and are attached to the frame 11 thereof, using cannulae (now shown), welding, or another well-known method. The open ends of the attachment struts 190,191 serve as barbs 16 extending from the first end 68 in the illustrative embodiment. It should be noted that the components of the embodiments of FIGS. 58-61 can either be made of the same material and strut thickness, or they can be formed of different materials. For example, in the embodiment of FIG. 61, the valve portion 43 frame 11 might be made of spring stainless steel, while the arms 165,166 are made of nitinol or a smaller gauge of stainless steel wire. Additionally, the arms 165,166 might be made of bioresorbable material or biomaterial which would help center the valve portion, then be resorbed or disappear after the valve has stabilized and thus, be unlikely to tilt, or if adherence of the leaflets to the vessel is not a concern.

FIG. 65 depicts an embodiment similar to that of FIG. 61 except that the arms 165,166 are configured such that they include both a first contact point 166,167 and a second contact point 179,189 that each contact the vessel wall 70 for further stability. The M-shaped arms 165,166 (the portion extending outward from the valve portion 43) further include a pair of attachment struts 190,191 that are affixed to the valve portion frame 11 and may extend outward to form anchoring barbs 16.

Figure 62A:
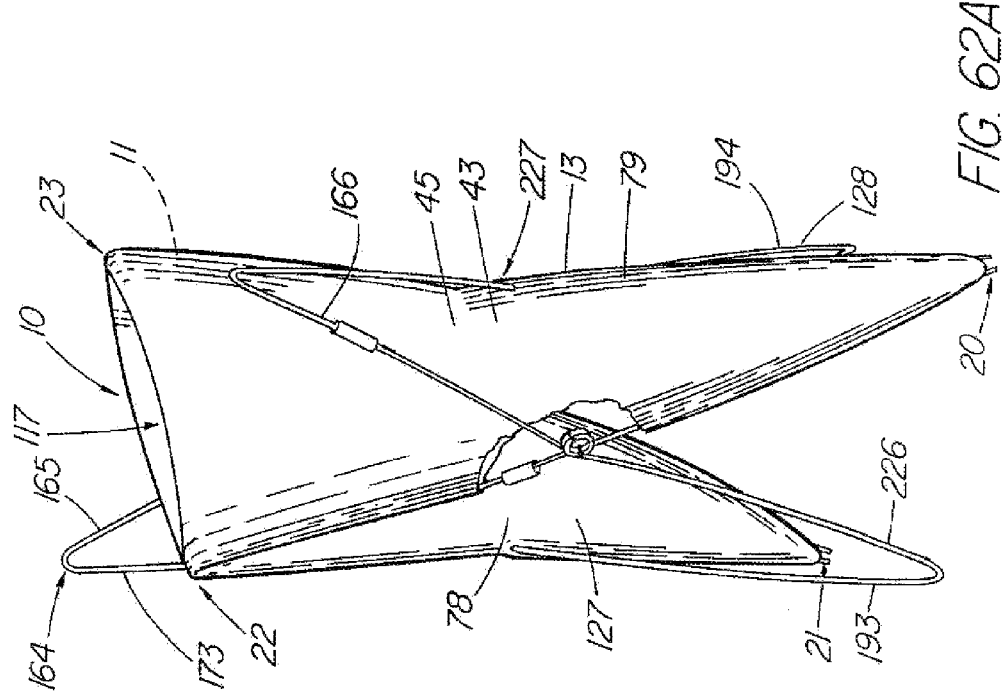
FIG. 62A depicts a pictorial view of an embodiment of the present invention that includes lateral support arms and supplemental support legs.
Figure 62:
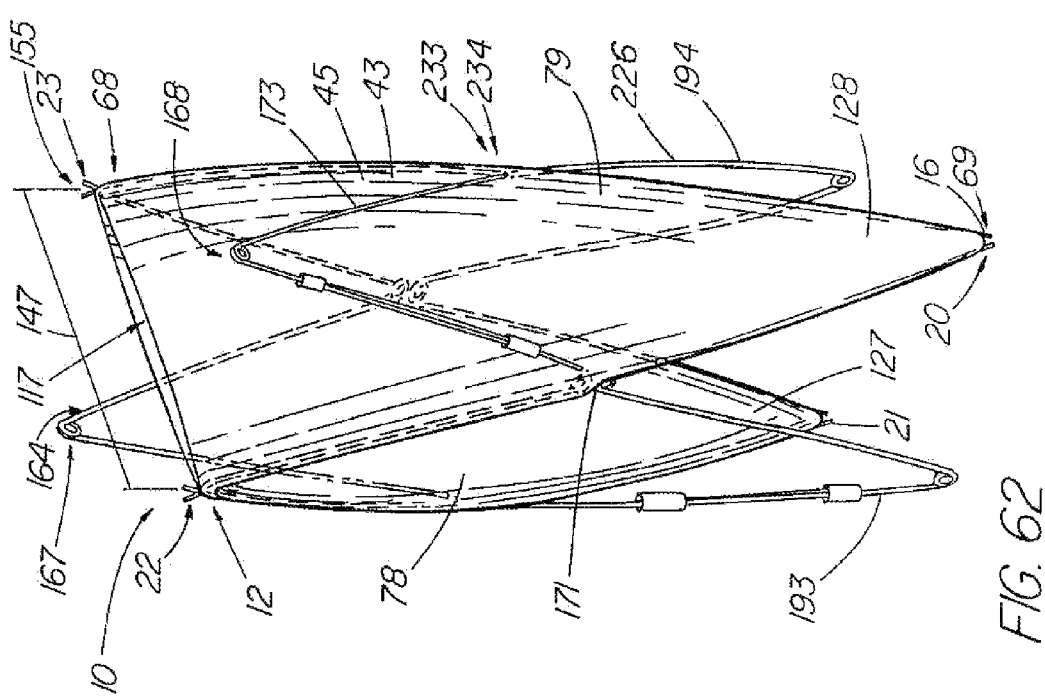
FIG. 62 depicts a pictorial view of an embodiment of the present invention that includes lateral support arms and supplemental support legs.

FIGS. 62-62A depict similar embodiments of the present invention in which the centering support structure 164 includes both a set of lateral arms 165,166 as in the previous embodiments, along with a pair of supplemental legs 193,194 for additional longitudinal support. In the embodiment of FIG. 62, the device 10 comprises a first and a second serpentine elements or zig-zag stent portions 174,226 attached end to end using an attachment mechanism 199 such as suture. The legs 127,128 then span both zig-zag portions 174,226, such that bends 22 and 23, located at the first end of the valve portion 43, are part of the first zig-zag portion 174, while bends 20 and 21, located at the second end 69 of the valve portion 43, are part of the second zig-zag portion 226. The embodiment of FIG. 62A comprises a single frame 11 which also forms the lateral arms 165,166 and the supplemental legs 193,194, as well as the legs 127,128 of the valve portion 43. The legs include a loop 227 located midway on the sides 13 that provide an attachment point to the crossing struts of lateral arms 165,166 supplemental legs 193,194, which optionally include attachment loops 227.

The embodiments of FIGS. 62-62A are but two examples of a method of forming a valve portion 43 having two lateral arms 165,166 and two supplemental legs 193,194. FIG. 80 depicts a frame 11 of yet another embodiment whereby the first and second serpentine elements 173,226 are joined by a series of elongate valve leg struts 225 that are attached to selected struts 238 of the serpentine elements 173,226 with cannulae 15 or another well-known method of bonding such that the individual serpentine sections 240 across the two serpentine elements 173,226 form the legs 127,128 of the valve 43 to which the leaflets 78,79 are attached (similar to that depicted in FIG. 62). For purposes of the present disclosure, a serpentine section 240 is defined as a bend 237 and the accompanying struts 238 that originate therefrom to assume a V-shape component, which connects to adjacent bends 245 oriented in the opposite direction to form the 'zig-zag' or 'Z' or 'S' configuration. In addition to comprising the attachment mechanism 171 that joins the two serpentine elements 173, 226, the leg struts also provide added rigidity to the legs 127,128 and frame 11 so that the weight of column of blood acting on the leaflets is less likely to cause the top bends 22,23 to be pulled inward toward one another, thereby changing the shape of the valve 43, which could affect the coaptation of the leaflets (how well they fit together or contact one another) and perhaps, lessen the radial pressure or force being applied against the vessel wall. Furthermore, the leg struts 225 may be conveniently extended beyond each of the bends 20,21,22,23 such that they form a series of eight barbs (two at each bend with four oriented in the proximal direction and four in the distal direction, to anchor the device 10 following deployment.

Unlike embodiments of the present invention in which the frame 11 can be flattened to facilitate attachment of the covering or leaflets, the covering must be attached to the tubular-shaped illustrative embodiments of FIGS. 62-62A and 80, and others, by another means. One exemplary method includes introducing a wedge or chisel-shaped mandril into the lumen of the device over which a wet, diamond-shaped piece SIS or other covering 45 is placed such that it conforms and assumes its characteristic saddle-shaped configuration. The covering is closely aligned with the frame 11 of the valve portion, then the covering 45 is attached along the axis that includes the orifice 117 by hooking the barbs 16 located at bends 22 and 23 therethrough. The covering 45 is then attached in a similar manner using the barbs 16 at ends 20 and 21. The mandril diameter is controlled to result in a deployed valve that produces the desired amount of coaptation of the leaflets and other performance characterisitics. The covering is then sutured in the manner similar to that depicted in FIGS. 26-26A. To attach the covering around that point which the lateral arms 165,166 and supplemental legs 193,194 extend from the frame 11, a slit is made a corresponding point along the covering that allows the struts to emerge, then the covering is wrapped therearound and secured in place. After the covering has dried, it is slit along the short axis to form the orifice, preferably leaving a 1-2 mm gap of covering remaining between the bend 12 and the edge of the orifice 117 to help prevent reflux at the corner bends 22,23. The mandril may be removed before or after the drying process.

Referring now to FIGS. 80 and 81, the lateral arms 165,166 and supplemental legs 193,194 that comprise the centering support structure 164 in the illustrative embodiment are made up of serpentine sections 440 comprising alternating lateral arm serpentine sections 236 and valve leg serpentine sections 235, the latter comprising a portion of the frame 11 supporting the two legs 127,128. In the illustrative embodiment, the valve leg serpentine sections 235 are longer than the lateral arms section 236 (and lateral arms 165,166). For example, the struts 238 of the lateral arm serpentine sections 236 may be 12 mm, as opposed to 15 mm for the struts 238 of the longer serpentine sections 235. Shortening the lateral arms 165,166 and supplemental legs 193,194 relative to the adjacent serpentine sections 235, helps keep the ends 167,168,241,242 thereof away from the bends 20,21,22,23 and barbs 16 of the valve portion 43 for easier loading and less chance of entanglement during deployment. Conversely, the lateral arms 165,166 and/or supplement legs 193,194 can be made longer (e.g., 20%) to also avoid having the ends becoming ensnared with barbs. A further advantage of a longer lateral arm 165,166 is that the leaflets 78,79, as they open and are folded back during valve function, cannot become caught on the contact points 167,168, which in the case of the longer arms, is well above the reach of the leaflets.

In addition to varying the length of the serpentine sections 235,236 to change the performance characteristics of the valve 43 (with leaflets not shown), the width 243 of the respective sections 235,236 can be varied, as well as the angle 239 formed by the bend 237 bend 12 (eyelet) diameters, and struts 238, to create a valve that exerts the desired radial pressure against the vessel such that it properly seals with the vessel without causing erosion of vessel wall tissue due to excess force. These dimensions can be changed to maintain a constant radial pressure across the range of different valve sizes. Furthermore, these dimensions can be manipulated to produce other desired characteristics, such as minimizing the amount of plastic deformation the frame 11 undergoes upon being loaded into the delivery system. In the illustrative artificial venous valve embodiment, the preferred range of the frame 11 wire thickness is 0.003-0.030", with a more preferred range of 0.0075-0.015" and most preferred range of 0.008-0.012". The preferred eyelet diameter at the bends 15,237 is 0.005-0.150", with a more preferred range of 0.010-0.060" and a most preferred range of 0.015-0.040". The length of the strut 238 of the valve leg serpentine section 235 is preferably 3-25 mm, with a more preferred range of 7-16 mm. The lateral arm serpentine section 236 is preferably 3-30 mm, with a more preferred range of 5-19 mm. Preferably, the struts 238 of the lateral arm serpentine section 236 should be about 80% of the valve leg serpentine section 235 or 20% longer, to give the desired amount of offset to avoid entanglement. Referring also to FIG. 62, the overall length of the illustrative device 10 (combined serpentine stents 173 and 226) should preferably be 1-2× the vein diameter, with a more preferred range of 1.5-2×. The valve covering 45 is sized so that the orifice 117 is able to open to 10-120% of the vein diameter, with a more preferred range being 60-100%. The preferred range of the amount of coaptation or contact of the leaflets 78,79 is 5-150% of the diameter of vein where the valve is implanted, with a more preferred range of 10-50%

FIG. 82 depicts a flattened portion of a first or second serpentine stent 173 in which the struts 238 are plastically deformed into a curved configuration 244 such that the serpentine sections 240 are more rounded and are able to better conform to the vessel wall. To maximize or preserve the curvature of the struts 238, the cannulae 15 attaching the valve strut 238 (as depicted in FIG. 80) can be located more toward the center of the respective struts 238 being joined. Otherwise, only the portions of the struts 238 about the bends 237 would assume the rounded or curved configuration 244 in the assembled device 10.

Figure 84:
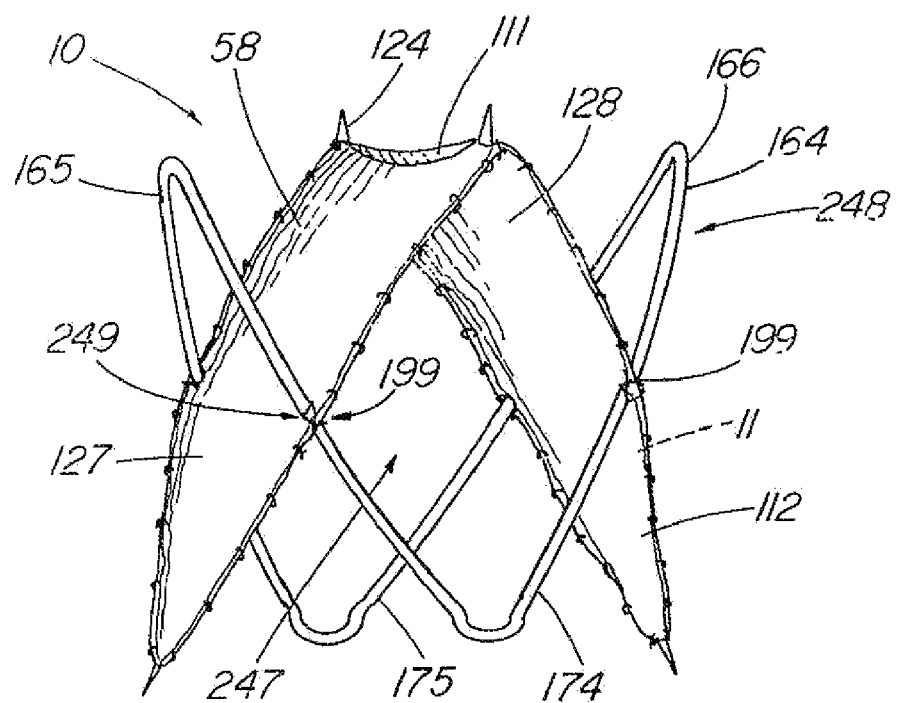
FIG. 84 depicts a side view of an embodiment similar to that of FIG. x formed out of a cannula.

FIG. 84 depicts a cannula-formed version of the general configuration of the embodiments of FIGS. 61,62A,62B, and 80. The illustrative nitinol frame 11 with centering support structure 164 comprise a pair of adjoining serpentine row sections 248 laser cut from nitinol cannula and electropolished to produce struts having a thickness and width of 0.006" (for the 14.0 and 16.5 mm diameter embodiments). The two sections 11,164 are interconnected by a short strut. The SIS material 58 is folded over and sewn to obliquely opposite struts of both adjoining serpentine row sections 248 so that each leaflet 78,79 entirely spans both sections with a notch 249 being formed in the material, whereby the material is wrapped around the strut 199 to maintain an leaflet outer edge 112 than engages the vessel wall. The optimal strut dimensions are dependent on several design factors. For example, the struts may be made thicker (e.g. 0.009") if the strut length is decreased. In the nitinol embodiment, the struts (sides 13) advantageous assume a slight serpentine configuration as the prosthesis is deployed. This produces better contact with the vessel wall than a straight wire strut, which allows for a better seal and facilitates remodeling of the ECM material. As with the similar wire-frame embodiments, two arms 165,166 extend laterally from the two legs 127,128 that carry the support frame 11 which comprises portions of both serpentine row sections 248. Similarly, two additional supplemental arms or legs 174,175 interconnect the two legs 127,128 and provide additional longitudinal stability. It should be noted that the serpentine row sections 248, although separate 'Z' stent units in this particular embodiment, can comprise any combination of struts or sections that produce a characteristic 'Z' stent configuration (of any number of bends) or an adjoining 'Z' stent configuration (e.g., FIGS. 62-62A).

Figure 85:
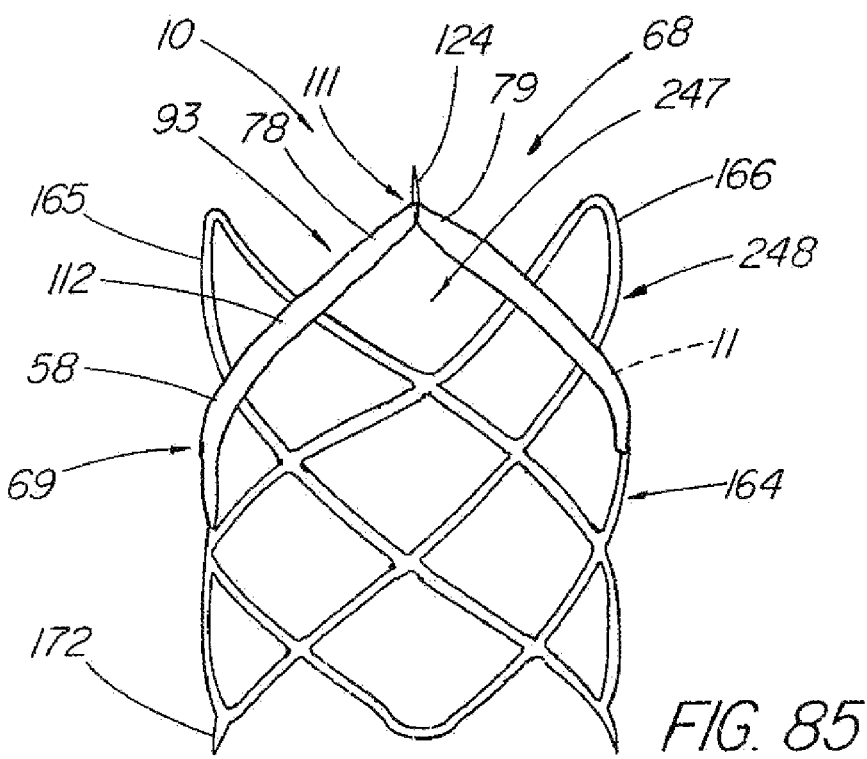
FIG. 85 depicts a side view of a valve embodiment in which the leaflets span multiple serpentine row sections of the prosthesis support frame.
Figure 86:
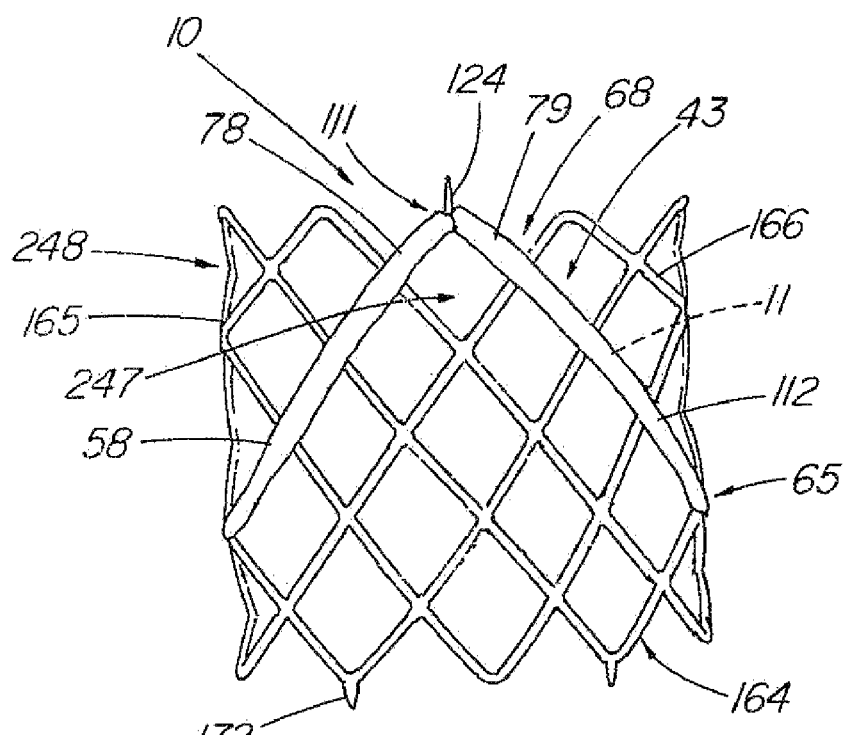
FIG. 86 depicts a side view of a valve embodiment in which the leaflets span multiple serpentine row sections of the prosthesis support frame.

Additional embodiments in which the leaflets span more than one serpentine segment 248 are depicted in FIGS. 85-86. In the embodiment FIG. 85, the leaflets 78,79 extend over the top three serpentine row sections 248 of the valve prosthesis such that struts of each collectively form the frame 11 of the valve portion 43. In the illustrative embodiment, the valve material 58 is sutured around the frame 11 so that it is able to directly engage the vessel wall. The remaining interconnecting struts and cells 247 form the centering support structure 164 with lateral arms 165,166 of the top serpentine row section 248 also serving as protection against the leaflets adhering to the vessel wall, which could cause loss of function. FIG. 86 depicts a related embodiment in which the leaflets 78,79 span four consecutive serpentine row sections 248 of the valve prosthesis support frame (the frame 11 plus centering support structure 164). The lateral arm structure 165,166 forms the same function as those in the embodiment of FIG. 85, although they include more struts and bends by virtue of the valve prosthesis support frame geometry. The number of serpentine row sections that the leaflets span can be varied to advantageously manipulate the angle that the leaflets assume relative to the longitudinal axis of the vessel. For example, the illustrative four-row leaflet embodiment of FIG. 86 includes a steeper leaflet angle than the three-row embodiment of FIG. 85. The leaflets angles may also be adjusted by manipulating the stent geometry (e.g., strut length, number of bends/points as measured circumferentially, etc.). For example, it is possible that a four-row leaflet could have a smaller (shallower) angle than certain three-row embodiments, depending on the support frame geometry. Both embodiment include integral barbs 124 at the first end 68 of the valve portion 43 and integral barbs 172 located on the centering support structure 164. It should be noted that the leaflets can be configured to span an even greater number of serpentine row sections that those embodiments illustrated. Furthermore, the leaflets can be place anywhere on the valve prosthesis support frame. For prosthesis could be formed such that there are uncovered serpentine row sections above the leaflets (or both above and below).

Figure 64:
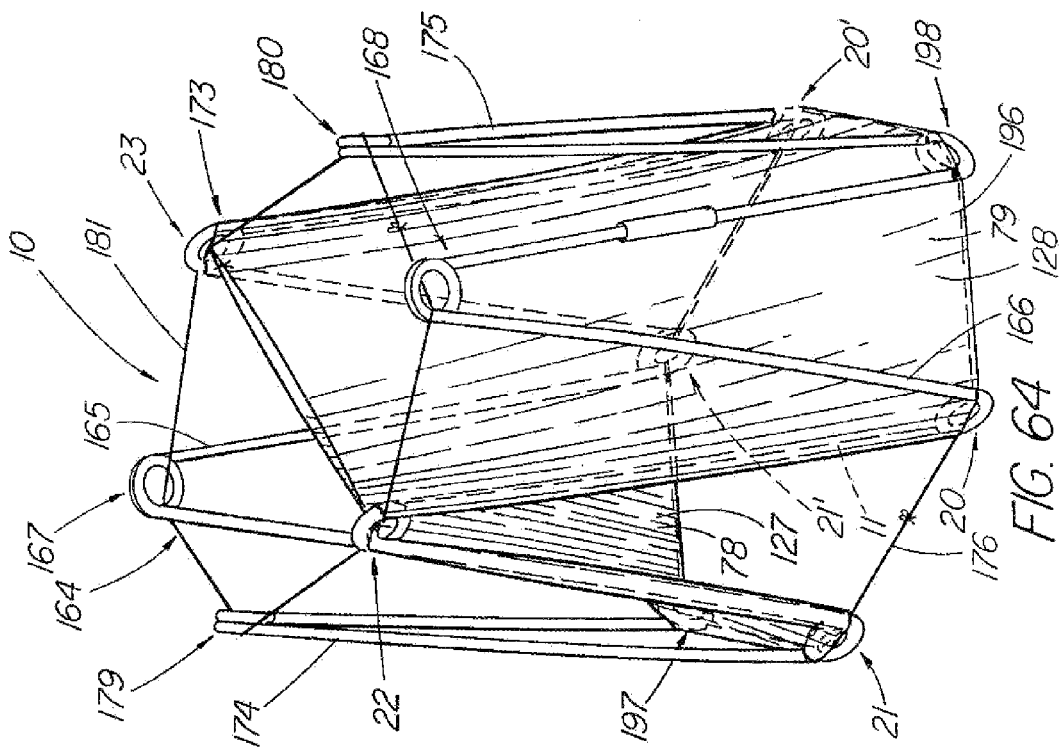
FIG. 64 depicts a pictorial view of an embodiment of the present invention wherein the frame and centering support structure comprise a serpentine stent frame.
Figure 63:
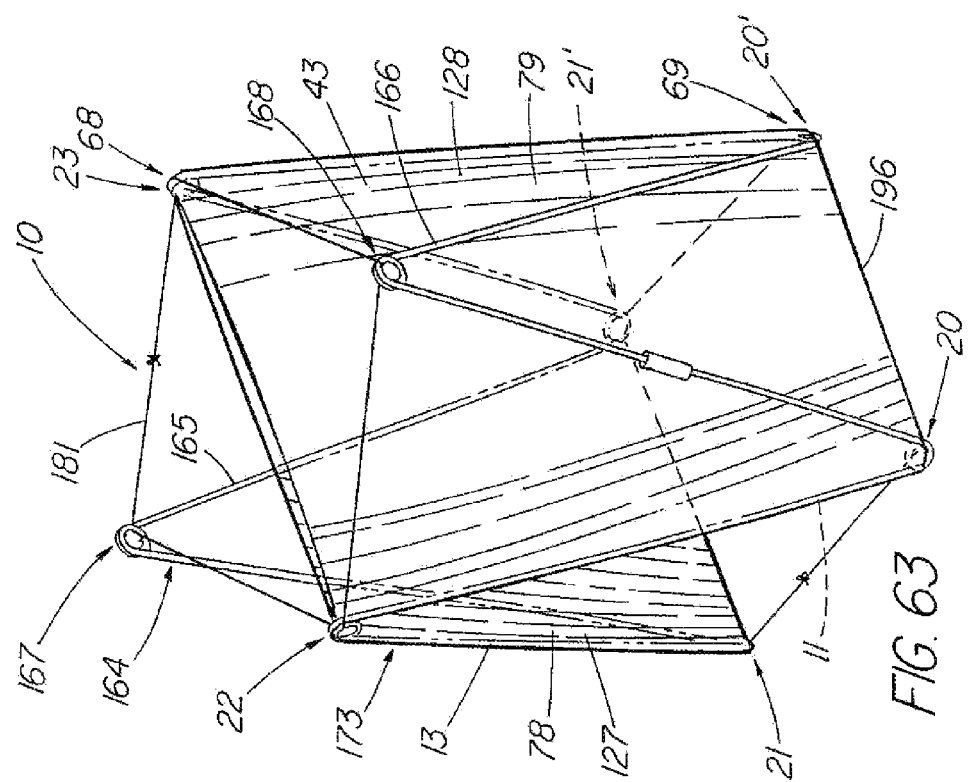
FIG. 63 depicts a pictorial view of an embodiment of the present invention wherein the frame and centering support structure comprise a serpentine stent frame.

FIGS. 63-64 depict valve embodiments in which frame 11 and centering support structure 164 are part of common structure comprising a first serpentine or zig-zag stent 173. In the embodiment of FIG. 63, the eight-point zig-zag frame includes four distal 20,20',21,21' and four proximal 22,23, 165,166 bends. The struts or sides 13 that connect points 22 and 23 provide the frame 11 support of the leaflets 78,79. Rather than supporting the entirety of each leaflet 78,79, the distal or bottom edges 196 thereof are not reinforced by the frame 11. An optional supplemental frame (not shown) may be included to reinforce the distal edges 196 and give it added resiliency for sealing against the vessel wall. FIG. 64 depicts a similar embodiment to that of FIG. 63 in which the frame 11 and centering support structure 164 are a twelve-point zig-zag stent, such that there are both first 165,166 and second 174,175 pairs of arms. The distal or bottom edge 196 of each leaflet 78,79 is attached to a distal contact point 198. As with the embodiment of FIG. 63, the distal edge 196 can be made resilient by the addition of a wire or other materials that help it provide a better seal against the vessel wall.

FIG. 68 depicts an valve embodiment that is related to that of FIG. 49 in which the valve portion 43 includes a circumferentially constraining mechanism 125. Unlike the sleeve or material depicted in FIG. 49, the circumferentially constraining mechanism 125 of FIG. 68 embodiment comprises a radially expandable or self-expanding stent, such as the illustrative ZILVER™ Stent (Cook Incorporated) which is made of a superelastic NiTi alloy. In the illustrative embodiment the circumferentially constraining mechanism 125 is particularly adapted to serve as a centering support structure 164, although even the material sleeve of FIG. 49 would offer a similar benefit, as well. The valve portion 43 can either be sized to fit within the outer stent such that it would not migrate, once deployed, or the legs 127,128 could be sutured or otherwise affixed to the legs using an attachment mechanism 171 to ensure that the valve portion 43 does not move relative to the constraining mechanism 125.

FIGS. 69-70 an embodiment of the present invention that is formed from a sheet of material 152, such as stainless steel, nitinol, etc., by laser cutting, stamping, machining, etching, or some other well-known method, wherein the design includes a valve portion 43 and integral centering support structure 164 that is folded or otherwise reshaped from the flat, first configuration 35 into the second, deployed configuration 36. In the embodiment of FIGS. 69-70, the centering support structure 164 comprises a pair of opposing arms 165,166 that extend outward when the device 10 is in the deployment configuration 36 such that they form a circular ring configured to support the valve portion 43 and prevent it from tilting within the vessel. In the illustrative embodiment, the centering support structure 164 is attached to the frame 11 of the valve portion 43 by a pair of short struts 199. One or more optional flexible zones 227, that comprise bends in the frame 11, may be incorporated thereinto to for the purpose of providing better conformity of the frame to the vessel.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27$^{th}$ edition.

What is claimed is:

1. A valve prosthesis for implantation within a vascular vessel, comprising:
    at least two leaflets; and
    a support frame having a lengthwise axis and comprising a leaflet support portion and a circumferential centering support element disposed adjacent the leaflet support portion on the lengthwise axis, the leaflet support portion comprising a self-expanding support frame having a plurality of struts interconnected by bends and configured for expansion to conform to a wall of the vascular vessel, the self-expanding support frame having a first end with only two bends and a second, opposite end with only two bends, the bends of the first end disposed on a first transverse axis and the bends of the second end disposed on a second transverse axis, the first transverse axis oriented approximately orthogonally with the second transverse axis;
    the circumferential centering support element comprising a ring-shaped frame having a plurality of struts interconnected by bends to define a zig-zag pattern with a third end and a fourth opposite end, at least two of the bends at the fourth end of the circumferential centering support element including a closed circumference; the self-expanding support frame and the ring-shaped frame being discrete;
    a first radial constraint disposed at the fourth end of the circumferential centering support element and configured to constrain the radial expansion thereof, the first radial constraint attaching two of the bends of the fourth end of the circumferential centering support element to the bends of the first end of the leaflet support portion;

the at least two leaflets attached along the struts of the leaflet support portion and forming a valve opening that extends between the two bends at the first end of the leaflet support portion and the attached two bends at the fourth end of the circumferential centering support element.

2. The valve prosthesis according to claim 1, wherein each bend at the fourth end of the circumferential centering support element includes a closed circumference.

3. The valve prosthesis according to claim 2, wherein the first radial constraint passes through at least one of the closed circumferences at the bends of the fourth end of the circumferential centering support element.

4. The valve prosthesis according to claim 2, wherein the first radial constraint passes through each of the closed circumferences at the bends of the fourth end of the circumferential centering support element.

5. The valve prosthesis according to claim 1, wherein the first radial constraint comprises one member selected from the group consisting of a suture, a ring fastener , a plastic band, and a strut.

6. The valve prosthesis according to claim 2, further comprising a second radial constraint disposed at the third end of the circumferential centering support element and configured to constraint the radial expansion thereof.

7. The valve prosthesis according to claim 6, wherein the second radial constraint comprises one member selected from the group consisting of a suture, a ring fastener, a plastic band, and a strut.

* * * * *